(12) United States Patent
Voytik-Harbin et al.

(10) Patent No.: US 12,343,450 B2
(45) Date of Patent: Jul. 1, 2025

(54) BIOLOGIC FILLER FOR RESTORING AND REGENERATING TISSUE

(71) Applicant: GENIPHYS, INC., Zionsville, IN (US)

(72) Inventors: Sherry L. Voytik-Harbin, Zionsville, IN (US); Theodore J. Puls, Carmel, IN (US)

(73) Assignee: GENIPHYS, INC., Zionsville, IN (US)

( * ) Notice: Subject to any disclaimer, the term of this patent is extended or adjusted under 35 U.S.C. 154(b) by 633 days.

(21) Appl. No.: 17/558,073

(22) Filed: Dec. 21, 2021

(65) Prior Publication Data

US 2022/0257836 A1 Aug. 18, 2022

Related U.S. Application Data

(63) Continuation of application No. PCT/US2021/015277, filed on Jan. 27, 2021.

(60) Provisional application No. 63/015,946, filed on Apr. 27, 2020, provisional application No. 62/966,398, filed on Jan. 27, 2020.

(51) Int. Cl.
| | | |
|---|---|---|
| *A61L 27/50* | (2006.01) | |
| *A61L 27/22* | (2006.01) | |
| *A61L 27/24* | (2006.01) | |
| *A61L 27/54* | (2006.01) | |

(52) U.S. Cl.
CPC ........... *A61L 27/502* (2013.01); *A61L 27/227* (2013.01); *A61L 27/24* (2013.01); *A61L 27/54* (2013.01); *A61L 2400/06* (2013.01)

(58) Field of Classification Search
None
See application file for complete search history.

(56) References Cited

U.S. PATENT DOCUMENTS

| | | |
|---|---|---|
| 3,949,073 A | 4/1976 | Daniels |
| 4,233,360 A | 11/1980 | Luck |
| 4,439,521 A | 3/1984 | Archer |
| 4,544,516 A | 10/1985 | Hughes |
| 4,582,640 A | 4/1986 | Smestad |
| 4,600,533 A | 7/1986 | Chu |
| 4,703,108 A | 10/1987 | Silver |
| 4,743,552 A | 5/1988 | Friedman |
| 4,776,853 A | 10/1988 | Klement |
| 4,789,663 A | 12/1988 | Wallace |
| 4,801,299 A | 1/1989 | Brendel |
| 4,829,000 A | 5/1989 | Kleinman |
| 4,902,508 A | 2/1990 | Badylak |
| 4,912,057 A | 3/1990 | Guirguis |
| 4,956,178 A | 9/1990 | Badylak |
| 5,032,508 A | 7/1991 | Naughton |
| 5,067,961 A | 11/1991 | Kelman |
| 5,163,955 A | 11/1992 | Love |
| 5,204,382 A | 4/1993 | Wallace |
| 5,266,480 A | 11/1993 | Naughton |
| 5,275,826 A | 1/1994 | Badylak |
| 5,281,422 A | 1/1994 | Badylak |
| 5,336,616 A | 8/1994 | Livesey |
| 5,352,463 A | 10/1994 | Badylak |
| 5,420,248 A | 5/1995 | Devictor |
| 5,460,962 A | 10/1995 | Kemp |
| 5,478,739 A | 12/1995 | Slivka |
| 5,554,389 A | 9/1996 | Badylak |
| 5,604,106 A | 2/1997 | Liotta |
| 5,641,518 A | 6/1997 | Badylak |
| 5,695,998 A | 12/1997 | Demeter |
| 5,800,812 A | 9/1998 | Eisenbach-Schwartz |
| 5,863,531 A | 1/1999 | Naughton |
| 5,885,619 A | 3/1999 | Patel |
| 5,948,429 A | 9/1999 | Bell |
| 6,020,200 A | 2/2000 | Enevold |
| 6,099,567 A | 8/2000 | Badylak |
| 6,171,344 B1 | 1/2001 | Atala |
| 6,187,039 B1 | 2/2001 | Hiles |
| 6,187,047 B1 | 2/2001 | Kwan |
| 6,206,931 B1 | 3/2001 | Cook |
| 6,241,981 B1 | 6/2001 | Cobb |
| 6,248,587 B1 | 6/2001 | Rodgers |
| 6,264,992 B1 | 7/2001 | Voytik-Harbin |
| 6,375,989 B1 | 4/2002 | Badylak |
| 6,379,710 B1 | 4/2002 | Badylak |
| 6,384,196 B1 | 5/2002 | Weis et al. |
| 6,419,920 B1 | 7/2002 | Mineau-Hanschke |
| 6,475,232 B1 | 11/2002 | Babbs |
| 6,485,723 B1 | 11/2002 | Badylak |
| 6,497,875 B1 | 12/2002 | Sorrell |
| 6,576,265 B1 | 6/2003 | Spievack |
| 6,586,493 B1 | 7/2003 | Massia |

(Continued)

FOREIGN PATENT DOCUMENTS

| | | |
|---|---|---|
| AU | 4884199 | 3/2000 |
| CN | 1100446500 | 11/2019 |

(Continued)

OTHER PUBLICATIONS

Keyes, K. et al. "An In Vitro Tumor Model: Analysis of Angiogenic Factor Expression after Chemotherapy," Cancer Research, 2002, 62, 5597-602.

Kim, "Characterization of Acid-soluble Collagen from Pacific Whiting Surimi Processing Byproducts," J. Food Science, 2004,69: C637-C642.

Kleinman, et al., "Membrane Complexes with Biological Activity," Biochemistry, 1986, 25, 312-8.

Kleinman, et al., "Preparation of Collagen Substrates for Cell Attachment: Effect of Collagen Concentration and Phosphate Buffer," Analytical Biochemistry, 1979,94, 308-12.

Knott et al., "Collagen Cross-Links in Mineralizing Tissues: A Review of Their Chemistry, Function, and Clinical Relevance," 1998,22(3): 181-187.

(Continued)

*Primary Examiner* — Nicole P Babson
(74) *Attorney, Agent, or Firm* — Barnes & Thornburg LLP

(57) ABSTRACT

Compositions and methods for filling tissue voids and defects with a self-assembling biopolymer configured to form a shape-retaining matrix are described.

19 Claims, 18 Drawing Sheets

(56) References Cited

U.S. PATENT DOCUMENTS

| | | |
|---|---|---|
| 6,592,623 B1 | 7/2003 | Bowlin |
| 6,592,794 B1 | 7/2003 | Bachrach |
| 6,666,892 B2 | 12/2003 | Hiles |
| 6,682,670 B2 | 1/2004 | Lullwitz |
| 6,893,812 B2 | 5/2005 | Woltering |
| 6,918,396 B1 | 7/2005 | Badylak |
| 6,962,814 B2 | 11/2005 | Mitchell |
| 7,029,689 B2 | 4/2006 | Berglund |
| 7,087,089 B2 | 8/2006 | Patel |
| 7,338,517 B2 | 3/2008 | Yost |
| 7,795,022 B2 | 9/2010 | Badylak |
| 7,815,686 B2 | 10/2010 | Badylak |
| 8,084,055 B2 | 12/2011 | Voytik-Harbin |
| 8,222,031 B2 | 7/2012 | Noll |
| 8,241,905 B2 | 8/2012 | Forgacs |
| 8,343,758 B2 | 1/2013 | Cheema |
| 8,431,158 B2 | 4/2013 | Shoseyov |
| 8,449,902 B2 | 5/2013 | Brown |
| 8,518,436 B2 | 8/2013 | Voytik-Harbin |
| 8,580,564 B2 | 11/2013 | Brown |
| 8,652,500 B2 | 2/2014 | Bosley, Jr. |
| 8,741,352 B2 | 6/2014 | Hodde |
| 8,785,389 B2 | 7/2014 | Brown |
| 9,101,693 B2 | 8/2015 | Brown |
| 9,205,403 B2 | 12/2015 | Dubois |
| 9,707,703 B2 | 7/2017 | Tully |
| 9,744,123 B2 | 8/2017 | Castiglione-Dodd |
| 9,757,495 B2 | 9/2017 | Murray |
| 11,739,291 B2 | 8/2023 | Voytik-Harbin |
| 2002/0000768 A1 | 1/2002 | Baek |
| 2002/0001701 A1 | 1/2002 | Matsunaga |
| 2002/0001727 A1 | 1/2002 | Robbins |
| 2002/0076816 A1 | 6/2002 | Dai |
| 2002/0170120 A1 | 11/2002 | Eckmayer |
| 2002/0172705 A1 | 11/2002 | Murphy |
| 2003/0001133 A1 | 1/2003 | Antika |
| 2003/0002168 A1 | 1/2003 | Richfield |
| 2003/0113302 A1 | 6/2003 | Revazova |
| 2004/0000063 A1 | 1/2004 | Hallee |
| 2004/0000304 A1 | 1/2004 | LeBrun |
| 2004/0000378 A1 | 1/2004 | Lee |
| 2004/0000780 A1 | 1/2004 | Li |
| 2004/0001376 A1 | 1/2004 | Breitwisch |
| 2004/0006395 A1 | 1/2004 | Badylak |
| 2004/0030404 A1 | 2/2004 | Noll |
| 2004/0037813 A1 | 2/2004 | Simpson |
| 2004/0137616 A1 | 7/2004 | Isseroff |
| 2005/0000141 A1 | 1/2005 | Cauley |
| 2005/0000194 A1 | 1/2005 | Friedmann |
| 2005/0001534 A1 | 1/2005 | Moon |
| 2005/0002020 A1 | 1/2005 | Inoue |
| 2005/0002268 A1 | 1/2005 | Otsuka |
| 2005/0002607 A1 | 1/2005 | Neuhaus |
| 2005/0002665 A1 | 1/2005 | Ito |
| 2005/0014181 A1 | 1/2005 | Galis |
| 2005/0019419 A1 | 1/2005 | Badylak |
| 2005/0142161 A1 | 6/2005 | Freeman |
| 2005/0153442 A1 | 7/2005 | Katz |
| 2005/0202058 A1 | 9/2005 | Hiles |
| 2005/0226856 A1 | 10/2005 | Ahlfors |
| 2005/0260748 A1 | 11/2005 | Chang |
| 2005/0266556 A1 | 12/2005 | Yoder |
| 2006/0000142 A1 | 1/2006 | Cui |
| 2006/0001340 A1 | 1/2006 | Pollmann-Retsch |
| 2006/0001475 A1 | 1/2006 | Price, Jr. |
| 2006/0001656 A1 | 1/2006 | LaViola, Jr. |
| 2006/0002355 A1 | 1/2006 | Baek |
| 2006/0002573 A1 | 1/2006 | Dale |
| 2006/0014284 A1 | 1/2006 | Graeve |
| 2006/0134072 A1 | 6/2006 | Pedrozo |
| 2006/0147501 A1 | 7/2006 | Hillas |
| 2006/0165667 A1 | 7/2006 | Laughlin |
| 2006/0235511 A1 | 10/2006 | Osborne |
| 2006/0257377 A1 | 11/2006 | Atala |
| 2007/0000265 A1 | 1/2007 | McEnaney |
| 2007/0000776 A1 | 1/2007 | Karube |
| 2007/0001410 A1 | 1/2007 | Thompson |
| 2007/0001906 A1 | 1/2007 | Pelzer |
| 2007/0002694 A1 | 1/2007 | Taugher |
| 2007/0026518 A1 | 2/2007 | Healy |
| 2007/0077652 A1 | 4/2007 | Peled |
| 2007/0190646 A1 | 8/2007 | Engler |
| 2007/0269476 A1 | 11/2007 | Voytik-Harbin |
| 2008/0000259 A1 | 1/2008 | Shewchuk |
| 2008/0000703 A1 | 1/2008 | Shindou |
| 2008/0000958 A1 | 1/2008 | Clarke |
| 2008/0001077 A1 | 1/2008 | Nakasugi |
| 2008/0001819 A1 | 1/2008 | Cohen |
| 2008/0001994 A1 | 1/2008 | Kaneko |
| 2008/0002205 A1 | 1/2008 | Keranen |
| 2008/0002680 A1 | 1/2008 | Skalecki |
| 2008/0095815 A1 | 4/2008 | Mao |
| 2008/0181935 A1 | 7/2008 | Bhatia |
| 2008/0199441 A1 | 8/2008 | Peled |
| 2009/0000698 A1 | 1/2009 | Beresford |
| 2009/0001759 A1 | 1/2009 | Kondo |
| 2009/0002693 A1 | 1/2009 | Engelbart |
| 2009/0002801 A1 | 1/2009 | Nakaho |
| 2009/0003246 A1 | 1/2009 | Hung |
| 2009/0069893 A1 | 3/2009 | Paukshto |
| 2009/0175922 A1 | 7/2009 | Voytik-Harbin |
| 2009/0269386 A1 | 10/2009 | Zubery |
| 2009/0280180 A1 | 11/2009 | Voytik-Harbin |
| 2010/0001195 A1 | 1/2010 | Konkle |
| 2010/0001434 A1 | 1/2010 | Atkin |
| 2010/0002726 A1 | 1/2010 | Kameyama |
| 2010/0119578 A1 | 5/2010 | To |
| 2010/0143476 A1 | 6/2010 | March |
| 2010/0272697 A1 | 10/2010 | Naji |
| 2010/0291532 A1 | 11/2010 | Ngo |
| 2011/0000277 A1 | 1/2011 | MacManus |
| 2011/0001829 A1 | 1/2011 | Lai |
| 2011/0182962 A1 | 7/2011 | McKay |
| 2012/0000943 A1 | 1/2012 | Pares Montaner |
| 2012/0001152 A1 | 1/2012 | Kim |
| 2012/0001349 A1 | 1/2012 | Harada |
| 2012/0001414 A1 | 1/2012 | Arning |
| 2012/0001717 A1 | 1/2012 | Park |
| 2012/0001895 A1 | 1/2012 | Lin |
| 2012/0002739 A1 | 1/2012 | Peron |
| 2012/0002975 A1 | 1/2012 | Nakazawa |
| 2012/0027732 A1 | 2/2012 | Voytik-Harbin |
| 2012/0115222 A1 | 5/2012 | Voytik-Harbin |
| 2012/0171768 A1 | 7/2012 | Voytik-Harbin |
| 2012/0189588 A1 | 7/2012 | Nahas |
| 2012/0273993 A1 | 11/2012 | Shoseyov |
| 2014/0000568 A1 | 1/2014 | Nishida |
| 2014/0001934 A1 | 1/2014 | Batur |
| 2014/0056865 A1 | 2/2014 | Samaniego |
| 2014/0193473 A1 | 7/2014 | Yoder |
| 2014/0193477 A1 | 7/2014 | Chaikof |
| 2015/0001053 A1 | 1/2015 | Miyamoto |
| 2015/0105323 A1 | 4/2015 | Novak |
| 2016/0001754 A1 | 1/2016 | Kim |
| 2016/0175482 A1 | 6/2016 | Quirk |
| 2018/0000501 A1 | 1/2018 | Baym |
| 2018/0050130 A1 | 2/2018 | Jiang |
| 2019/0003510 A1 | 1/2019 | Chasse |
| 2019/0351097 A1* | 11/2019 | Voytik-Harbin ..... A61K 9/0024 |
| 2020/0246507 A1 | 8/2020 | Voytik-Harbin |
| 2023/0131204 A1 | 4/2023 | Voytik-Harbin |

FOREIGN PATENT DOCUMENTS

| | | |
|---|---|---|
| DE | 20115753 | 1/2002 |
| EP | 1264878 | 12/2002 |
| EP | 1270672 A1 | 1/2003 |
| GB | 2366736 | 3/2002 |
| JP | 1247082 | 10/1989 |
| JP | 07074239 B | 8/1995 |
| JP | H0774239 | 8/1995 |
| JP | 2001511431 | 8/2001 |
| JP | 2005193055 | 7/2005 |
| JP | 2011525197 | 9/2011 |

(56) References Cited

FOREIGN PATENT DOCUMENTS

| | | |
|---|---|---|
| JP | 2013031730 | 2/2013 |
| JP | 2014198270 | 10/2014 |
| JP | 6510927 | 5/2019 |
| WO | 9215676 | 9/1992 |
| WO | 9300441 | 1/1993 |
| WO | 9403119 | 2/1994 |
| WO | 9423016 | 10/1994 |
| WO | 9717038 | 5/1997 |
| WO | 9806445 | 2/1998 |
| WO | 9852637 | 11/1998 |
| WO | 0015765 | 3/2000 |
| WO | 0047219 | 8/2000 |
| WO | 0062833 | 10/2000 |
| WO | 0110355 | 2/2001 |
| WO | 2001023529 | 4/2001 |
| WO | 2001045765 | 6/2001 |
| WO | 0148153 | 7/2001 |
| WO | 0178754 | 10/2001 |
| WO | 0207646 | 1/2002 |
| WO | 2002102237 | 1/2002 |
| WO | 0220729 | 3/2002 |
| WO | 2003068287 | 8/2003 |
| WO | 2003071991 | 9/2003 |
| WO | 03087337 | 10/2003 |
| WO | 03097694 | 11/2003 |
| WO | 2004028404 | 4/2004 |
| WO | 2004060426 | 7/2004 |
| WO | 2006125025 | 11/2006 |
| WO | 2007028079 | 3/2007 |
| WO | 2012004564 | 1/2012 |
| WO | 2017044847 | 3/2017 |
| WO | 2019023266 A1 | 1/2019 |

OTHER PUBLICATIONS

Koken, "About Collagen," Technical information, Support webpage, 2006.

Kondo et al., "Biology of Hematopoietic Stem Cells and Progenitors: Implications for Clinical Application," Annu. Rev. Immunol., 2003,21:759-806.

Kong et al., "FRET measurements of cell-traction forces and nano-scale clustering of adhesion ligands varied by substrate stiffness," PNAS, 2005; 102:4300-4305.

Korff, Thomas, and Hellmut G. Augustin. "Tensional forces in fibrillar extracellular matrices control directional capillary sprouting." Journal of cell science 112.19 (1999): 3249-3258.

Kreger et al., "Hyaluronan concentration within a 3D collagen matrix modulates matrix viscoelasticity, but not fibroblast response," Matrix Biol., 2009, 28(6):336-46.

Kreger et al., "Polymerization and matrix physical properties as important design considerations for soluble collagen formulations," 2010, Biopolymers, 93(8): 690-707.

Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.

Kubota, Y. et al., "Role of Laminin and Basement Membrane in the Morphological Differentiation of Human Endothelial Cells into Capillary-like Structures," Journal of Cell Biology, 1988, 107, 1589-98.

Kuo C.Y., et al., "Biohybrid Islet-Gland Equivalent for Transplantation," Journal of Cellular Biochemistry, Supplement 18C PZ110, Feb. 13-26, 1994.

Kuo Ching Chao et al., "A Novel Human Stem Cell Coculture System that Maintains the Survival and Function of Culture Islet-Like Cell Clusters," Cell Transplantation, Jun. 1, 2008, 657-64.

Kuo, C.Y., et al., "Formation of Pseudoislets from Human Pancreatic Cultures," Pancreas, 1992, 7(3) 320-5.

Larsson, L. et al., "Changes in the Islets of Langerhans in the Obese Zucker Rat," Lab. Invest. 1977, 36, 593-8.

Lee, et al., "Modulation of Secreted Proteins of Mouse Mammary Epithelial Cells by the Collagenous Substrata," The Journal of Cell Biology, 1984, 98, 146-55.

Lille et al., "Growth of Stratified Squamous Epithelium on Reconstituted Extracellular Matrices: Long-Term Culture," Journal of Investigative Dermatology, 1988, 90(2) 100-9.

Lin et al., "Comparison of Physical-Chemistry Properties of Type I Collagen from Different Species," Food Chemistry', 99(2): 244-251 (2005).

Liu, C. H., et al., "Effects of Salvianolic Acid-A on NIH/3T3 Fibroblast Proliferation, Collagen Synthesis and Gene Expression," World J. Gastroentero, 2000,6(3) 361-4.

Liu, D. C., Y. K. Lin, and M. T. Chen. "Optimum condition of extracting collagen from chicken feet and its characetristics." Asian-Australasian journal of animal sciences 14.11 (2001): 1638-1644.

Lynn et al., "Antigenicity and immunogenicity of collagen," J Biomed Mater Res, Part B: Appl Biomater, 2004; 7IB: 343-354.

Malvern, Introduction to the Mechanics of a Continuous Medium. Upper Saddle River, NJ: Prentice-Hall, 1969.

Marotta, M., G. Martino, "Sensitive Spectrophotometric Method for the Quantitative Estimation of Collagen", Analytical Biochemistry, vol. 150, 1985, pp. 86-90.

Maru et al., "An Oncogenic Form of the FIt-I Kinase has a Tubulogenic Potential in a Sinusoidal Endothelial Cell Line," European Journal of Cell Biology, 2000, 79, 130-43.

McBeath et al., "Cell shape, cytoskeletal tension, and RhoA regulate stem cell lineage commitment," Developmental Cell, 2004; 6:483-495.

Michalopoulos & Pitot, "Primary Culture of Parenchymal Liver Cells on Collagen Membranes," Experimental Cell Research, 1975,94,70-8.

Mienaltowski, et al. "Structure, Physiology, and Biochemistry of Collagens," Advances in Experimental Medicine and Biology, 2014, 802, 5-29.

Mikos, A.G., et al., "Islet Transplantation to Create a Bioartificial Pancreas," Biotech, and Bioengineering, 1994, 43, 673-7.

Miller et al., "Preparation and Characterization of the Different Types of Collagen," Methods in En/\mology, 82: 33-64 (1982).

Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.

Mitra, et al., "Preparation and characterization of malonic acid cross-linked chitosan and collagen 3D scaffolds: an approach on non-covalent interactions," J. Mater. Sci Mater Med, 2012, 23, 1309-21.

Mizuno et al., "Osteogenesis by bone marrow stromal cells maintained on type 1 collagen matrix gels in vivo." Bone 20:101-107(1997).

Mokonjimobe et al., "Hexosaminidase and alkaline phosphatase activities in articular chondrocytes and relationship to cell culture conditions," Experientia, 1992,48(4) 396-8.

Munakata, Hidekazu, et al. "Interaction between collagens and glycosaminoglycans investigated using a surface plasmon resonance biosensor." Glycobiology 9.10 (1999): 1023-1027.

Mund J.A et al., "Endothelial progenitor cells and cardiovascular cell-based therapies," Cylotherapy, 2009; 11(2): 103-13.

Na et al., "In Vitro Collagen Fibril Assembly in Glycerol Solution: Evidence for a Helical Cooperative Mechanism Involving Microfibrils," Biochemistry, 1986; 25: 958-966.

Na et al., "Mechanism of in Vitro Collagen Fibril Assembly," Journal of Biological Chemistry, 1986; 261(26): 12290-12299.

Na, "Monomer and Oligomer of Type I Collagen: Molecular Properties and Fibril Assembly," Biochemistry, 1989, 28 (18):7161-7167.

Narmoneva et al., "Endothelial Cells Promote Cardiac Myocyte Survival and Spatial Reorganization", Circulation, 110, 962-968, (Aug. 24, 2004).

Nerem, R., "Tissue Engineering: The Hope, The Hype and The Future," Tissue Engineering, 2006, 12(5) 1143-50.

Nguyen et al., "Comparison of the Amino Acid Composition of Two Commercial Porcine Skins (Rind)," Journal of Agricultural and Food Chemistry, 34(3): 565-572 (1986).

(56) References Cited

OTHER PUBLICATIONS

Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.
Nugent, H.M. et al. "Endothelial Implants inhibit Intimal Hyperplasia After Porcine Angioplasty," Circulation Research, Mar. 5, 1999, 84(4) pp. 384-391.
Office Action for Japanese Patent Application No. JP2022-545858, dated Dec. 3, 2024. English translation appended.
Orschell-Traycoff, Christie M., et al. "Homing and engraftment potential of Sca-1+ lin—cells fractionated on the basis of adhesion molecule expression and position in cell cycle." Blood, The Journal of the American Society of Hematology 96.4 (2000): 1380-1387.
Osborne, et al., "Investigation into the tensile properties of collagen/chondroitin-6-sulphate gels: the effect of crosslinking agents and diamines", Medical & Biological Engineering & Computing, vol. 36, 129-134, (1998).
Ozerdem, et al., "Physical Response of Collagen Gels to Tensile Strain", Journal of Biomechanical Engineering, vol. 117, 397-401, (Nov. 1995).
PCT Search Report and Written Opinion prepared for PCT Application No. PCT/US2021/015277, mailed Apr. 29, 2021.
"Artificial Blood Vessel," English translation of Japanese Patent Application Publication No. 3-12169, 1991, 16 pages.
"Basement Membrane" accessed online at httD://en.wikiDedia.ora/wiki/Basement membrane#ComDOsition on Jun. 11, 2010.
"Density" from Merriam-Webster online, accessed on Feb. 1, 2011.
"Extracellular Matrix" accessed at httD://en.wikipedia.org/wiki/Extracellular matrix on Jun. 11. 2010.
"Stem Cells and the future of Regenerative Medicine" published by National Academy of Sciences, p. 19,2002.
Abou-Neel et al. "Use of multiple unconfined compression for fine control of collagen gel scaffold and mechanical properties," Soft Matter, 2006, 2,986-92.
Asem, E.K. el al. "Basal lamina of Avian Ovarian Follicle: Influence On Morphology of Granulosa Cells In-Vitro," Comparative Biochemistry and Physiology, Part C, 125 (2000), pp. 189-201.
Asem, E.K et al. "Effect of Basal Lamina on Progesterone Production by Chicken Granulosa Cells In Vitro—Influence of Follicular Development," Comparative Biochemistry and Physiology, Part C, 125 (2000) pp. 233-244.
Backer, MP., et al. "Large Scale Production of Monoclonal Antibodies in Suspension Culture," Biotechnology and Bioengineering, 1988, 32, pp. 993-1000.
Badylak, S.T., et al. "Directed Connective Tissue Remodeling, Upon a Biologic Collagen Substrate," J. Cell Biochem. 1992, Supplement 16F, Abstract No. CE 027, p. 124.
Badylak, S.T., et at. "Endothelial Cell Adherence to Small Intestinal Submucosa: An Acellular Bioscaffold," Biomaterials, 1999, 20, pp. 2257-2263.
Bailey JL et al., "Collagen Oligomers Modulate Physical and Biological Properties of Three-Dimensional Self-Assembled Matrices," Biopolymers, 2010; 95(2): 77-93.
Bell, Brett J. et al., "Cell Density and Extracellular Matrix (ECM) Microstructure Control Mechanical Behavior of Engineered Tissue Constructs, 2005 Summer Bioengineering conference", (Jun. 22-26, 2005).
Bell, et al., "Production of a tissue-like structure by contraction of collagen lattices by human fibroblasts of different proliferative potential in vitro," Mar. 1979, Proc. Natl. Sci. USA, 76(3) pp. 1274-1278.
Bhatia, S.N. et al., "Controlling Cell Interactions by Micropatterning in Co-Cultures: Hepatocytes and 3T3 Fibroblasts," Journal of Biomedical Materials Research, 1997, 34, pp. 189-199.
Billiar, Cellular and Biomolecular Mechanics and Mechanobiology, Amit Gefen, Ed., p. 210 (2011).
Bioartificial Organs, Richard Skalak and Fred Fox, eds. Tissue Engineering, Chapter V. Transplants and Artificial Organs, pp. 209,211-39, and 241-2 (Alan R. Liss, Inc. 1988).
Bjornsson, S., "Simultaneous Preparation and Quantitation of Proteoglycans by Precipitation with Alcian Blue", Analytical Biochemistry, vol. 210, 1993, pp. 282-291.
Blay et al., "Epidermal Growth Factor Promotes the Chemotactic Migration of Cultured Rat Intestinal Epithelial Cells," J. Cell Physiology, 1985, 124(1) pp. 107-112.
Block, S., "Peroxygen Compounds," Disinfection, Sterilization and Preservation, 4th Edition 1991, pp. 167-181, phildelphia, Lea, & Febiger.
Blum, K.M., et al., "Acellular and high-density, collagen-fibril constructs with suprafibrillar organization," Biomaterials Science, The Royal Society of Chemistry, 2016, 4, 711-23.
Boder G.B. et al. "Long-Term Production of Insulin by Isolated Rabbit Pancreatic Islets in Suspension Culture," J. Cell Biol. 1968, 39(16a).
Boder G.B., et al. "Extended Production of Insulin by Isolated Rabbit Pancreatic Islets; Evidence for Biosynthesis of insulin," Proc. Soc. Exptl. Biol. Med., 1969, 131, p. 507-13.
Boder, G.B. and Hull, R.H., "Introduction to Techniques in Mammalian Cell Culture," Manual of Industrial Microbiology and Biotechnology, 1983, Ed. A.L. Demain and N.A. Solomon, pp. 248-262.
Boder, G.B., "Mammalian Cell Cultures for Genetically Engineered Products," Toxicologic Pathology, 1989, 17(4) p. 827.
Boder, G.B., et al. "Long Term Monolayer Cultures of Islet Cells from Neonatal Mice," J. Cell Biol., 1973, 59, p. 29a.
Boder, G.B., et al. "Visible Light Inhibits Growth of Chinese Hamster Ovary Cells," European J. Cell Biol., 1983, 31, pp. 132-136.
Boyd et al. Atlas and Text of Corneal Pathology and Surgery; 2011 [Document REJECTED by EXAM, because illegible].
Brandner et al., "replicating the Hematopoietic Stem Cell Niche," Purdue University, BME Graduate Student Association Research Symposium, Poster Presentation, Jul. 16, 2009.
Brasack, et al. "Biocompatibility of Modified Silica-Protein Composite Layers," Journal of Sol-Gel Science and Technology, 2000. Vol. 19, pp. 479-482.
Brennan and Davison, "Role of aldehydes in collagen fibrillogenesis in vitro," Biopolymers, vol. 19, 1980, Issue 10, p. 1861-1873.
Brightman et al., "Time-Lapse Confocal Reflection Microscopy of Collagen Fibrillogenesis and Extracellular Matrix Assembly In Vitro", Biopolymers, vol. 54, 222-234, (2000).
Brookes, S. et al., "Three-dimensional tissue-engineered skeletal muscle for laryngeal reconstruction: 3D Tissue Engineered Skeletal Muscle," The Laryngoscope, Aug. 26, 2017, 128(3) 603-9.
Brown, et al., "Ultrarapid Engineering of Biomimetic Materials and Tissues: Fabrication of Nano- and Microstructures by Plastic Compression," Advanced Functional Materials, 2005, 15, 1762-70.
Callister, W. D, Jr., Materials Science and Engineering: an Introduction, 3rd edition, New York, NY, John Wiley & Sons, Inc., 1994.
Campbell, J.H. et al. "Endothelial Cell Influences on Vascular Smooth Muscle Phenotype," Ann. Rev. Physiol., 1986, vol. 48, 384-91.
Case J et al., "Human CD34+AC133+VEGFR-2+ cells are not endothelial progenitor cells but distinct, primitive hematopoietic progenitors," Exp Hemaiol., 2007; 35(7): 1109-18.
Castano, E., et al., "Inhibition of DNA Synthesis by Aspirin in Swiss 3T3 Fibroblasts," Journal of Pharmacology and Experimental Therapeutics, 1997, 280(1) p. 366-72.
Caves, et al., "Elastin-linke protein matrix reinforced with collagen microfibers for soft tissue repair," Biomaterials, 2011,32(23)5371-9.
Chandrakasan, Gowri, Dennis A. Torchia, and Karl A. Piez. "Preparation of intact monomeric collagen from rat tail tendon and skin and the structure of the nonhelical ends in solution." Journal of Biological Chemistry 251.19 (1976): 6062-6067.
Chicatun, et al., "Osteoid-Mimicking Dense Collagen/Chitosen Hybrid Gels," BioMacromolecules, 2011, 12,2946-56.
Chor Wing Tarn et al. EWMA Journal, 2012; 12(2).
Ciovacco, Wendy A., et al. "The role of gap junctions in megakaryocyte-mediated osteoblast proliferation and differentiation." Bone 44.1 (2009): 80-86.

(56) References Cited

OTHER PUBLICATIONS

Comper, W. D., and A. Veis, "Characterization of Nuclei in in Vitro Collagen Fibril Formation", Biopolymers, vol. 16. 1977, pp. 2133-2142.
Compston, "Bone marrow and bone: a functional unit," Journal of Endocrinology, 173: 387-394, 2002.
Condell RA et al., "Analysis of Native Collagen Monomers and Oligomers by Size-Exclusion High-Performance Liquid Chromatography and its Application," Analytical Biochemistry, 1993; 212: 436-445.
Critser et al., "Collagen matrix physical properties modulate endothelial colony forming cell-derived vessels in vivo," 2010, Microvasc. Res., 80(1): 23-30.
Davis, et al., "Injectable Self-Assembling Peptide Nanofibers Create Intramyocardial Microenvironments for Endothelial Cells", Circulation, 111, 442-50, (Feb. 1, 2005).
De Luca, et al., "Evidence That Human Oral Epithelium Reconstituted In Vitro and Transplanted on Patients with Defects in the Oral Mucosa Retains Properties of the Original Donor Site," Transplantation, 1990, 50(3) p. 454-9.
Delcourt-Huard, et al., "Reconstituted Human Gingivial Epithelium: Nonsubmerged In Vitro Model," In Vitro Cellular & Developmental Biology Animal, Jan. 1997, 33(1) p. 30-6.
PCT Search Report and Written Opinion prepared for PCT Application No. PCT/US2021/024893, completed May 27, 2021.
PCT Search Report and Written Opinion prepared for PCT/US2018/016069, completed Mar. 9, 2018.
Pizzo et al., "Cell-Extracellular Matrix (ECM) Micro-Mechanical Behavior Depends on ECM Microstructure and Cell Type", 2005 Summer Bioengineering Conference, (Jun. 22-26, 2005).
Pizzo et al., "Extracellular matrix (ECM) microstructural composition regulates local cell-ECM biomechanics and fundamental fibroblast behaviour: a multidimensional perspective", J Appl Physiol, 98: 1909-1921, (2005).
Pizzo et al., "Long-term Production of Choline Acetylatransferase in the CNS After Transplantation of Fibroblasts Modified with a Regulatable Vector", Mol Brain Res, 126, 1-13 (2004).
Prater DN et al., "Working hypothesis to redefine endothelial progenitor cells," Leukemia, 2007; 21(6): 1141-9 (Epub Mar. 29, 2007).
Rehman, et al., "Secretion of Angiogenic and Antiapoptotic Factors by Human Adipose Stromal Cells", Circulation, 109: 1292-8, (Mar. 16, 2004).
Reinisch et al., "Humanized large-scale expanded endothelial colony-forming cells function in vitro and in vivo," Blood, 2009; 113:6716-6725.
Reinlib, et al., "Cell Transplantation as Future Therapy for Cardiovascular Disease?", Circulation, 101: el 82-el 87, (2000).
Roeder B. A., K. Kokini, J. E. Sturgis, J. P. Robinson, S. L. Voytik-Harbin, "Tensile Mechanical Properties of Three- Dimensional Type I Collagen Extracellular Matrices with Varied Microstructure", J. Biomech. Eng., vol. 124, 2002, pp. 214-222.
Roeder et al., "Local, Three-Dimensional Strain Measurements Within Largely Deformed Extracellular Matrix Constructs", J Biomech Eng, 126, 699-708, (2004).
Rucha Joshi: "Purdue e-Pubs Open Access Dissertations Theses and Dissertations Designer Collagen- Fibril Biograft Materials for Tunable Molecular Delivery," Jan. 1, 2016 httDs://docs.lib.Durdue.edu/ooen access dissertations/1218.
Ruszczak et al., "Effect of collagen matrices on dermal wound healing," Advanced drug Delivery Reviews, 2003, 55, 1595-611.
Saltzman et al., "Three-dimensional Cell Cultures Mimic Tissues," Ann. N.Y. Acad. Sci., 1992, 665, 259-73.
Sato et al., "Artificial Esophagus," Materials Science Forum, 1997, 250, 105-14.
Scadden, "The stem cell niche as an entity of action," Nature, 441: 1075-1079, 2006.
Schechner et al., "In vivo formation of complex microvessels lined by human endothelial cells in an immunodeficient mouse," PNAS, Aug. 1, 2000, vol. 97, No. 16,9191-9196.
Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.
Schor et al., "The Use of Three-Dimensional Collagen Gels for the Study of Tumour Cell Invasion In Vitro: Experimental Parameters Influencing Cell Migration Into the Gel Matrix," Int. J. Cancer, 1982, 29, 57-62.
Seltleman, "Tension Precedes Commitment - Even for a Stem Cell," Molecular Cell, 2004; 14:148-150.
Shepherd, et al., "Effect of fiber crosslinking on collage-fiber reinforced collagen-chondroitin-6-sulfate materials for regenerating load-bearing soft tissues," Journal of Biomedical Materials Research, 2012, 101(1) 176-84.
Shields et al., Invasion of Collagen Gels by Mouse Lympoid Cells, Immunology, 1984, 51, 259-68.
Shimizu, "Fabrication of pulsatile cardiac tissue grafts using a novel 3-dimensional cell sheet manipulation technique and temperature-responsive cell culture surfaces," Circ Res., 2002, 90:e40-48.
Shiozawa et al., "The bone marrow niche: habitat to hematopoietic and mesenchymal stem cells, and unwitting host to molecular parasites," Leukemia, 22(5): 941-950, 2008.
Shoulders, et al., "Collagen Structure and Stability," Annu. Rev. Biochem., 2009, 78,929-58.
Sieminski, A. L., Robert P. Hebbel, and Keith J. Gooch. "The relative magnitudes of endothelial force generation and matrix stiffness modulate capillary morphogenesis in vitro." Experimental cell research 297.2 (2004): 574-584.
Silver et al., "Collagen self-assembly and the development of tendon mechanical properties," Journal of Biomechanics, 2003;36:1529-1553.
Silver et al., "Type I Collagen in Solution," The Journal of Biological Chemistry, 1980, 19(10) 9427-33.
Spradling, Allan, Daniela Drummond-Barbosa, and Toshie Kai. "Stem cells find their niche." Nature 414.6859 (2001): 98-104.
Stem Cell Differentiation (science and global issues/biology, cell biology), 2013.
Stephens, et al., "Oligomeric collagen as an encapsulation material for islet/beta-ceil replacement: effect of islet source, dose, implant site, and administration format," Am. J. Physiol. Endocrinol. Metab., 2020, vol. 319, pp. E388-E400.
Strang, et al., Linear Algebra and Its Applications. 3rd edition. San Diego, CA: Academic Press, 1988.
Sweeney, et al. "Defining the domains of type I collagen involved in heparin-binding and endothelial tube formation," Proceedings of the National Academy of Science, USA 1998, 95, 275-80.
Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.
Taichman et al., "Human Osteoblasts Support Hematopoiesis through the Production of Granulocyte Colony- stimulating Factor," Journal of Experimental Medicine, 1994; 179:1677-1682.
Takahashi, et al., "Compressive force promotes Sox9, type II collagen and aggrecan and inhibits IL-ip expression resulting in chondrogenesis in mouse embryonic limb bud mesenchymal cells," Journal of Cell Science, 1998, 111(14) 2067-76.
Taqvi et al., "Influence of scaffold physical properties and stromal cell coculture on hematopoietic differentiation of mouse embryonic stem cells," Biomaterials, 2006; 24:6024-6031.
Tebmar et al., "Hydrogels for tissue engineering," Fundamentals of Tissue Engineering and Regenerative Medicine, 2009; p. 495-517.
Timmermans F et al., "Endothelial progenitor cells: identify defined?", J Cell Mol Med, 2009; 13(1): 87-102.
Vasiliev and Gelfand, Neoplastic and Normal Cells in Culture, Cambring University Press, p. 19, 1981.
Veis, Arthur, et al., "Fundamentals of Interstitial; Collagen Self-Assembly", 1994, Extracellular Matrix Assembly and Structure, Academic Press, pp. 15-45.
Vescoi et al., "In vivo-like drug responses of human tumors growing in three-dimensional gel-supported primary culture," Proc. Natl. Acad. Sci. USA, 1987, 84, 5029-33.

(56) References Cited

OTHER PUBLICATIONS

Volpi et al. "On adaptive structures of the collagen fibrils of bone and cartilage," J. Biomech, 24 (Suppl 1), 1991, 67-77, abstract only.
Voytik-Harbin et al., "Application and Evaluation of the Alamarblue Assay For Cell Growth and Survival of Fibroblasts", In Vitro CetlDev BiolAnim, 34, 239-246, (1998).
Voytik-Harbin et al., "Identification of Extractable Growth Factors from Small Intestine Submucosa," J Cell. Biochemistry, 1997; 67: 478-491.
Voytik-Harbin et al., "Simultaneous Mechanical Loading and Confocal Reflection Microscopy for Three-Dimensional Microbiomechanical Analysis of Biomaterials and Tissue Constructs", Microsc Microanal, 9, 74-85, (2003).
Voytik-Harbin et al., Small Intestinal Submucosal A Tissue-Derived Extracellular Matrix That Promotes Tissue-Specific Growth and Differentiation of Cells in Vitro, Tissue Engineering, 4, 2, 157-174, (1998).
Voytik-Harbin et al., "Three-Dimensional Imaging of Extracellular Matrix and Extracellular Matrix-Cell Interactions", Methods In Cell Biology, 63, 583-597, (2001).
Wakitani et al., "Mesenchymal Cell-Based Repair of Large, Full Thickness Defects of Articular Cartilage," J. Bone Joint Surg. Am., Abstract, 1994, 76(4) 579-92.
Wang et al., Sheng Li Xue Bao, 2005, 57(2): 259-269; Astract Only.
Wess, Collagen fibrillar structure and hierarchies in P. Fratzl (ed.), Collagen: Structure and Mechanics, Springer Science + Business Media, LLC, New York, 2008,53-60.
Whittington et al., "Collagen oligomers modulate physical and cell-instructive properties of polymerizabte collagen matrices," Biomaterials Day Society for Biomaterials, Nov. 6, 2010 (PowerPoint presentation and poster).
Whittington, C, et al., "Oligomers Modulate Interfibril Branching and Mass Transport Properties of Collagen Matrices," Microsc Microanal, Oct. 2013, 19(5) 20 pages.
Whittington, C.F., et al., "Collagen-Polymer Guidance of Vessel Network Formation and Stabilization by Endothelial Colony Forming Cells In Vitro," Macrornolecular Bioscience, 2013, 13, 1135-49.
Wikipedia, "Oligomer," Sep. 25, 2015, retrieved on Jun. 22, 2018, from https://en.wikipedia.Org/w/index.php?til! e+Oligomer&oldid=682674890.
Williams et al., 1978, Joum Biol Chem, 253: 6578-6585.
Wilson, et al. "A fibril-reinforced poroviseoelastic swelling model for articular cartilage," Journal of biomechanics, 2005, 38(6) pp. 1195-1204.
Wu et al., "Bioprinting three-dimensional cell-laden tissue constructs with controllable degradation," Scientific Reports, 6:24474, Apr. 19, 2016.
Xi, et al. "Pore size and pore-size distribution control of porous silica," Sensors and Actuators, 1995, vol. B 24-25, pp. 347-352.
Yang, E.K. et al., "Tissue Engineered Artificial Skin Composed of Dermis and Epidermis," International Society for Artificial Organs, 2000, 24(1) 7-17.
Yang, et al., "The application of recombinant human collagen in tissue engineering." Biodrugs 18:103-119 (2004).
Yoder et al., "Redefining endothelial progenitor cells via clonal analysis and hematopoietic stem/progenitor cell principals," BLOOD, 2007, 109:1801-1809.
Young et al., "Use of meschymal stem cells in a collagen matrix for Achilles tendon repair. J. Ortopaedic Res. 16"406-413(1998).
Young, et al., "Adult Stem Cells." Anat. Record Pt. A: Disc. Mol. Cell. Evol. Biol. 276A:75-102 (2004).
Zhu et al., "Designed composites for mimicking compressive mechanical properties of articular cartilage matrix," Journal of the Mechanical Behavior of Biomedical Materials, 2014, 36, 32-46.
Zorlutuna et al., "Nanopatterning of Collagen Scaffolds Improve the Mechanical Properties of Tissue Engineered Vascular Graft," Biomacromolecules, 2009, 10, 814-21.
Denton, G.W., "Chlorhexidine," Disinfection, Sterilization and Preservation, 4th Edition 1991, Philadelphia, Lea, & febiger, p. 274-89.

Elsdale and Bard, "Collagen Substrata for Studies on Cell Behavior," The Journal of Cell Biology, 1972, 54, p. 626-37.
Emerman et al., "Maintenance and Induction of Morphological Differentiation in Dissociated Mammary Epithelium on floating Collagen Membranes," In Vitro, 1977, 13(5) pp. 316-328.
Engler et al., "Matrix elasticity directs stem cell lineage specification," Cell, 2006; 126:677-689.
Engler et al., "Myotubes differentiate optimally on substrates with tissue-like stiffness: pathological implications for soft or stiff microenvironments," Journal of Cell Biology, 2004; 165:877-887.
Engler et al., "Substrate elasticity directs adult mesenchymal stern cell differentiation," Abstract 783, The 37th Middle Atlantic Regional Meeting, May 2005.
Extended European Search Report for EP patent application No. 21747781.9, dated 23-Jan. 2024.
Fischbach, et al., "Three-dimensional in vitro model of adipogenesis: coparison of culture conditions." Tissue Engineering 10:215-229 (2004).
Foglia, et al. A new method lor the preparation of biocompatible silica coated-collagen hydrogels, J. Mater. Chem. B., 2013, vol. 1, pp. 1283-1290.
Francis, et al. "Endothelial cell-matrix interactions in neovascularization," Tissue Engineering Part B: Reviews, 2008, 14(1) 19-32.
Freed et al., "Joint Resurfacing Using Allograft Chondrocytes and Synthetic Biodegradable Polymer Scaffolds," J. Biomedical Materials Res., 1994, 28, p. 891-9.
Freeman et al., "In vivo-like growth of human tumors in vitro," Proc. Natl. Acad. Sci. USA, Apr. 1986, 83, 2694-8.
Freshney, R.I., "Culture of Animal Cells: A Manual of Basic Technique," Chapters 12 and 13, Alan R. Liss, Inc., New York (1994) p. 119-43.
Friess, "Collagen-biomaterial for drug delivery," European Journal of Pharmaceutics and Biopharmaceutics, 1998, 45 (2) 113-36.
Fulzele, S. V., P. M. Satturwar, A. K. Dorle, "Study of the Biodegradation and in Vivo Biocompatibility of Novel Biomaterials", European Journal of Pharmaceutical Sciences, vol. 20,2003, pp. 53-61.
Gallop, p. M., and S. Seifter, "Preparation and Properties of Soluble Collagens", Soluble Collagens, 1963, pp. 635-641.
Gelman et al., "Collagen Fibril Formation in Vitro," J. Biol. Chem., 1979, 254(22): 11741-11745.
Gelman et al., "Collagen Fibril Formation," J. Biol. Chem., 1979, 254(1): 180-186.
Girasole et al., "17-p Estradiol Inhibits IL-6 Production by Bone Marrow-Derived Stromal Cells and osteoblasts In Vitro: A Potential Mechanism for the Antiosteoporotic Effects of Estrogens," The Journal of Clinical Investigation, Inc. 1992, 89,-. 883-91.
Glowacki, J. and Mizuno, S. "Collagen Scaffolds for Tissue Engineering," Biopolymers, 2007, 89, 338-44.
Griffey, S., N. D. Schwade, C. G. Wright, "Particulate Dermal Matrix as an Injectable Soft Tissue Replacement Material", J. Biomed. Mater. Res. Vol. 58,2001, pp. 10-15.
Grinnel, "Cell-Collagen Interactions: Overview," Methods in Enzymology, 1982, 82, 499-5.
Grover, et al., "Crosslinking and composition influence the surface properties, mechanical stiffness and cell reactivity of collagen-based films," Acta Biomater, 2012, 8(8) 3080-90.
Hambli et al., "Physically based 3D finite element model of a single mineralized collagen microfibril," Journal of Theoretical Biology, 2012, 301, 28-41.
Hayashi, "The effect of three-dimensional structure of extracellular matrix on cellular functions including response to growth factors," Biophysics, 1992, 32(4) p. 211-5.
Hirschi KK et al., "Assessing identify, phenotype, and fate of endothelial progenitor cells," Arterioscler Thromb Vase Biol, 2008; 28(9): 1584-95 (Epub Jul. 31, 2008).
Hirschi, K.K. et al. "PDGF, TGF-p. and Heterotypic Cell-Cell Interactions Mediate Endothelial Cell-Induced Recruitment of 10T1/2 Cells and Their Differentiation to a Smooth Muscle Fate," The Journal of Cell Biology, 1998, 141(3) pp. 805-814.
Ho et al., "Characterization of Collagen Isolation and Application of Collagen Gel as a Drug Carrier", J. of Controlled Release, vol. 44, pp. 103-112 (1997).

(56) References Cited

OTHER PUBLICATIONS

Ho, M., et al., "Identification of Endothelial Cell Genes by Combined Database Mining and Microarray Analysis," Physiol. Genomics, 2003, 13, 249-62.
Hou, et al., "Radiolabeled Cell Distribution After Intramyocardial, Intracoronary, and Interstitial Retrograde Coronary Venous Delivery", Circulation, 112, 150-6, (Aug. 30, 2005).
Huang et al., 2005, Mechanisms and Dynamics of Mechanical Strengthening in Ligament-Equivalent Fibroblast- Populated Collagen Matrices, Annals of Biomedical Engineering, 21: 289-305.
Hunt, T. K., P. Twomey, B. Zederfeldt, and J. E. Dunphy, "Respiratory Gas Tensions and PH In Healing Wounds", American Journal of Surgery, vol. 114, 1967, pp. 302-307.
Ibrahiem, E.I.H., et al. "Orthotopic Implantation of Primary N-[4-(5-Nitro-2-furyl)-2-thiazolyl]formamide-induced Bladder Cancer in Bladder Submucosa: An Animal Model for Bladder Cancer Study," Cancer Research, 1983, 43, 617-20.
Ingram D et al., "Unresolved questions, changing definitions, and novel paradigms for defining endothelial progenitor cells via clonal analysis and hematopoietic stem/progenitor cell principals," Blood, 2007; 109(5): 1801-9 (Epub Oct. 19, 2006).
Ingram D et al., "Vessel wall-derived endothelial cells rapidly proliferate because they contain a complete hierarchy of endothelial progenitor cells," Blood, 2005; 105(7):2783-6 (Epub Dec. 7, 2004).
Ingram, D. A., et al., "Identification of a Novel Hierarchy of Endothelial Progenitor Cells Using Human Peripheral and Umbilical Cord Blood", Blood, 104, 2752-2760, (2004).
International Preliminary Report on Patentability and Written Report for PCT/US2006/018998; 9 pages.
International Preliminary Report on Patentability and Written Report for PCT/US2006/019130; 8 pages.
International Search Report and Written Opinion for PCT/US2008/086232, Jan. 16, 2009, 12 pages.
International Search Report and Written Opinion for PCT/US2010/042290; 13 pages.
International Search Report and Written Opinion for PCT/US2012/040737; 6 pages.
International Search Report and Written Opinion for PCT/US2015/047176; 12 pages.
International Search Report for International Application No. PCT/US07/020463, Feb. 21, 2008, 6 pgs.
International Search Report/Written Opinion for PCT/US2007/011681 completed Nov. 6, 2007.
Ji et al., "Mechanics of electrospun collagen and hydroxyapatite/collagen nanofibers," Journal of the Mechanical behavior of Biomedical Materials, 2012, 13, 185-93.
JPK Instruments, "Collagen: levels of structure and alignment," pp. 1-6, retrieved from the internet 127/2022, https://www.jpk.coni/app=technotes-img/A.EM/pdl7jpk-app-coilagen.14-1.pdf (Year: 2022).
Junnosuke, "Tissue culture-Basics and Applications-," Asakura Publishing Co., Ltd., 1965, p. 31.
Kacena et al., J. of Histotechnology, 2004, 27:119-130.
Kashtan, H et al., "Intra-rectal injection of tumor cells: a novel animal model of rectal cancer," Surgical Oncology, 1992, 1,251-6.
Ciovacco et al., Bone, 2009, 44(1): 80-86.
International Search Report and Written Opinion issued by the ISA/US Commissioner for Patents, dated Jul. 6, 2018, for International Application No. PCT/US2018/029473.
Korff et al., Jour. of Cell Science, vol. 112: 3249-3258 (1999).
Lee et al.Journal of Anatomy (2019) 234, pp. 252-262 (Year: 2019).
Liu, Asian-Aust J. Anim. Sci, 2001; 14(11): 1638-1644.
Merriam-Webster, Engineer definition, retrieved from the internet Jan. 27, 2022: https://www.merriam-webster.com/dictionary/engineer (Year: 2022).
Merriam-Webster: definition of "synthesis", retrieved from the internet, Sep. 1, 2022: https://www.merriam-webster.com/dictionary/synthetic (Year: 2022).
Munakata, et al., Glycobiology, vol. 9, 1023-1027 (1999).
Novak et al. "Mechanisms and Microenvironment Investigation of Cellularized High Density Gradient Collagen Matrices via Densification" Adv Funct Mater. Apr. 25, 2016; 26(16): 2617-2628.
Office Action for Chinese patent application No. 202180025637.4, dated Jan. 20, 2025. Translation Appended.
Orschell-Traycoff et al., Blood, 2000, 96:1380-1387.
Sakai et al., Biomaterials 27 (2006) pp. 335-345 (Year: 2006).
Spradling et al., "Stem Cells Find Their Niche," Nature, 414: 98-104, 2001.
Supplementary European Search Report for EP 18791439.5, completed Dec. 10, 2020.
Whittington, Catherine F., et al. "Oligomers modulate interfibril branching and mass transport properties of collagen matrices." Microscopy and Microanalysis 19.5 (2013): 1323-1333. (Year: 2013).

* cited by examiner

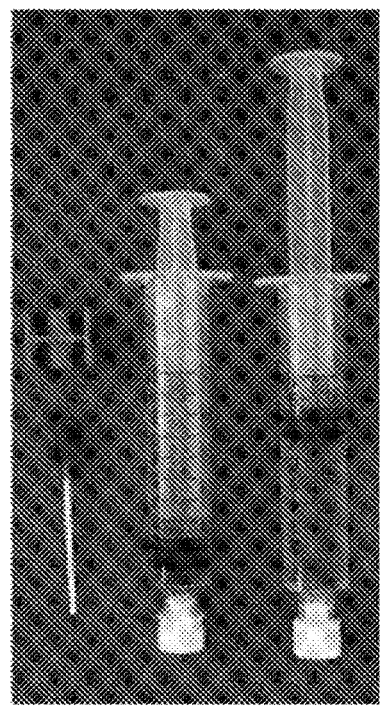
FIG. 1A
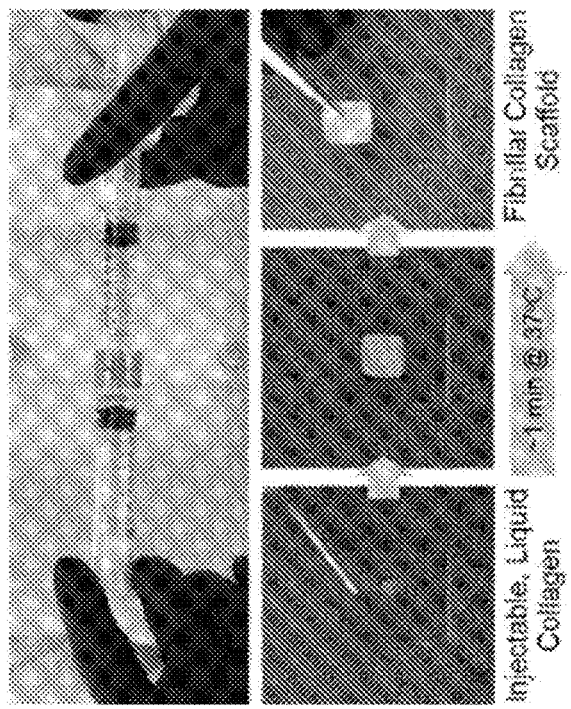
FIG. 1B
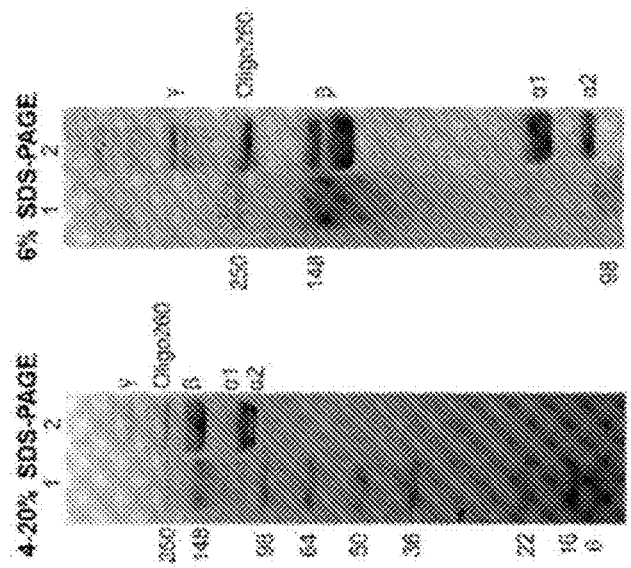
FIG. 1C
| Property | Mean ± SD |
|---|---|
| Polymerization Time (minutes) | 0.75 ± 0.05 |
| Collagen Concentration (mg/mL) | 7.73 ± 0.21 |
| Shear Storage Modulus (kPa) | 3.16 ± 0.16 |
| Shear Loss Modulus (kPa) | 0.40 ± 0.02 |
| Compression Modulus (kPa) | 7.67 ± 0.42 |
FIG. 1D

FIG. 2A
FIG. 2C
FIG. 2B
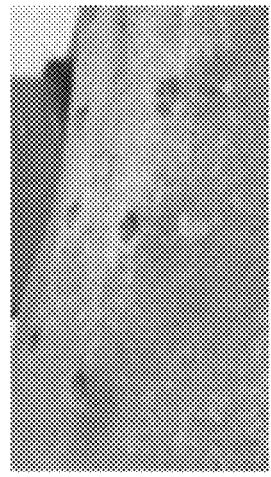
FIG. 2D
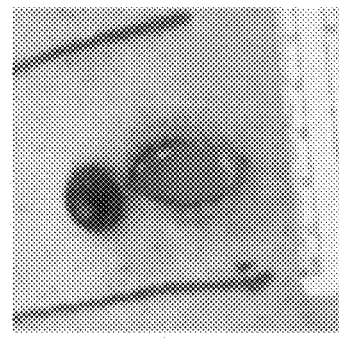
FIG. 2F
FIG. 2E
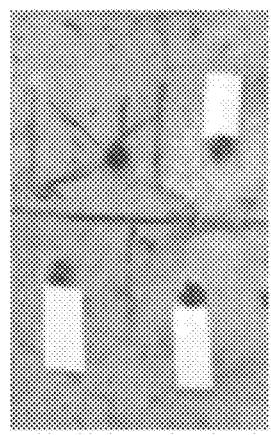
FIG. 2G
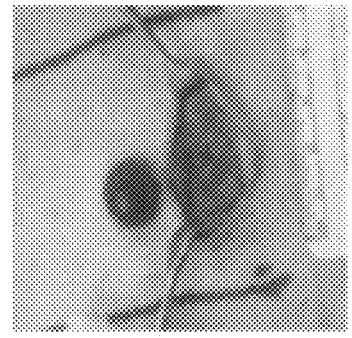
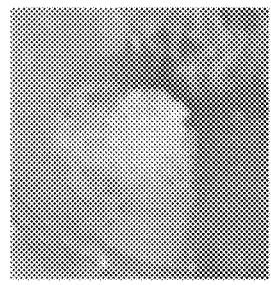

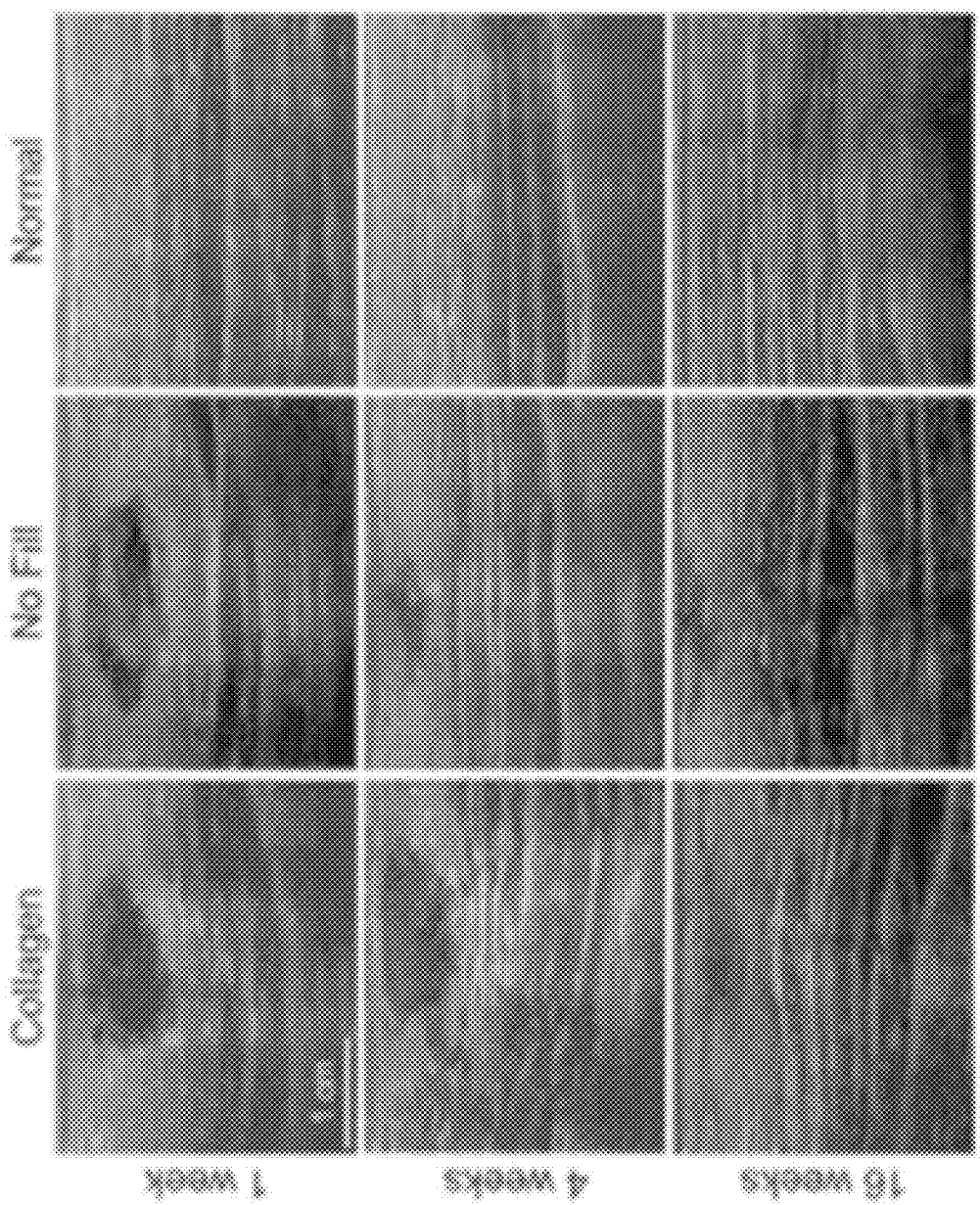

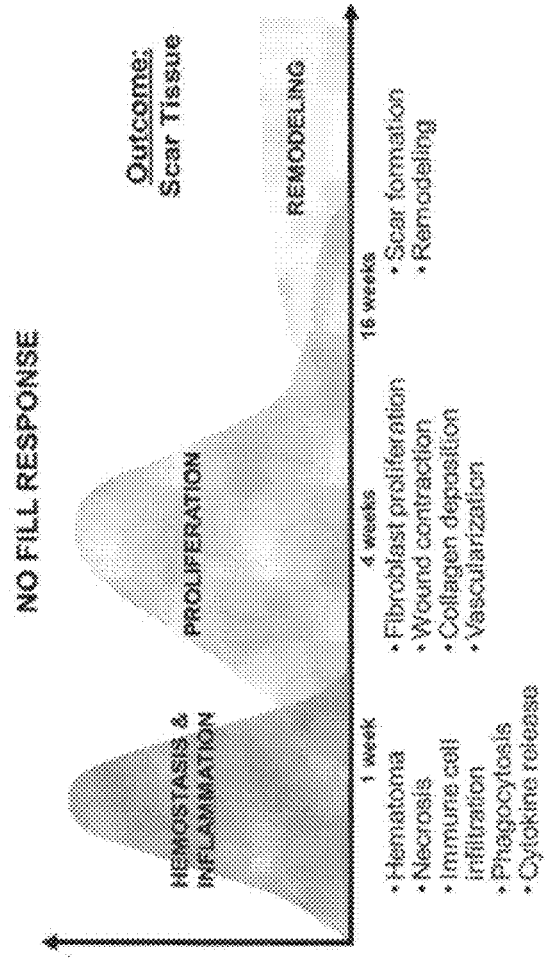
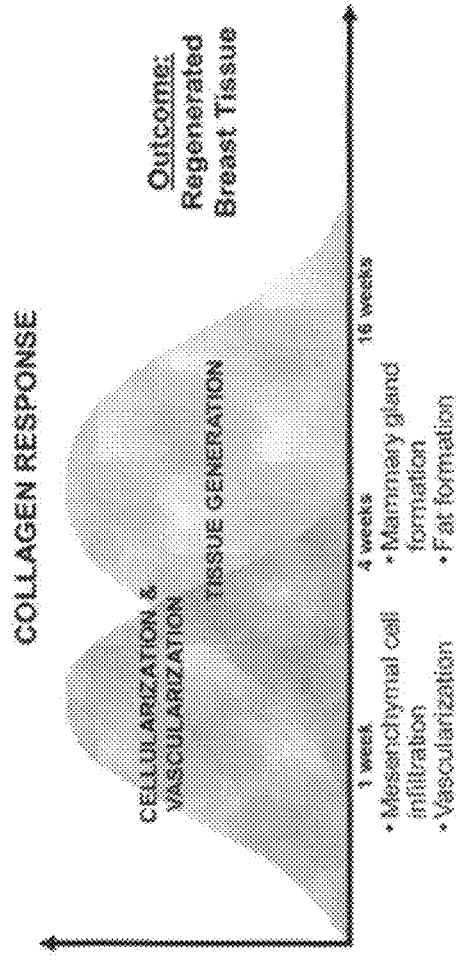
FIG. 8A
FIG. 8B

Gross Breast/Surgical Site Appearance Scoring

Erythema and Eschar
0 = Normal; no erythema
1 = Very slight erythema (barely perceptible)
2 = Well-defined erythema
3 = Moderate erythema
4 = Severe erythema (beet redness) to eschar formation Edema
0 = No edema
1 = Very slight edema (barely perceptible)
2 = Well-defined edema (edges are well-defined by definite raising)
3 = Moderate edema (raised approximately 1 mm)
4 = Severe edema (raised more than 1 mm and extending beyond surgical site)

Breast Uniformity/Consistency Scoring

0 = Normal
1 = Minimal to marginal divot, deformity, or inconsistency (lump, mass)
2 = Moderate divot, deformity, or inconsistency (lump, mass)
3 = Obvious divot, deformity, or protuberance

FIG. 10

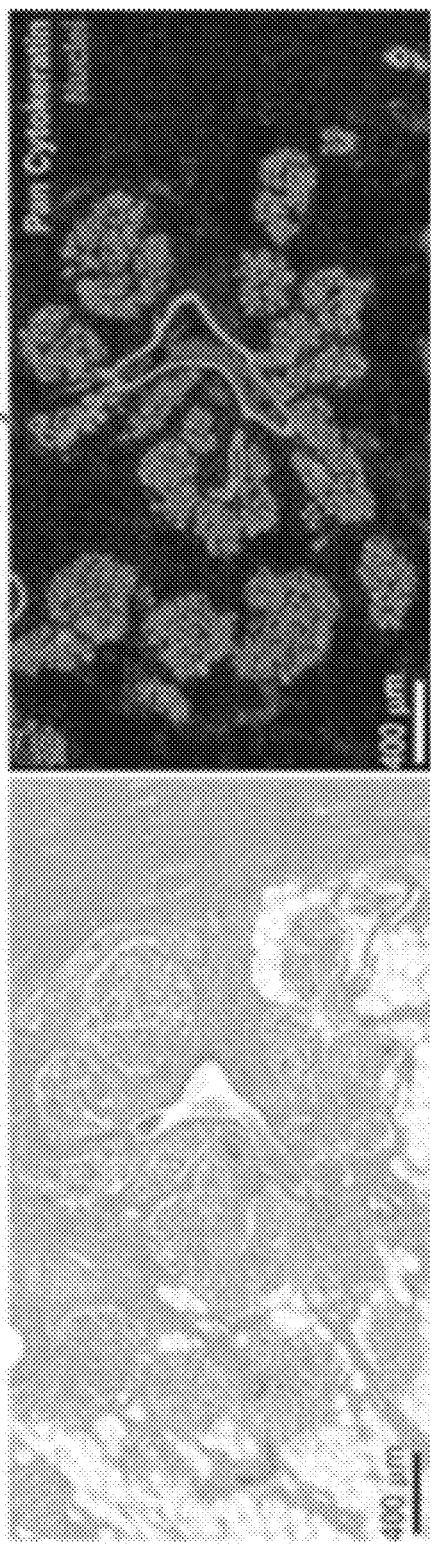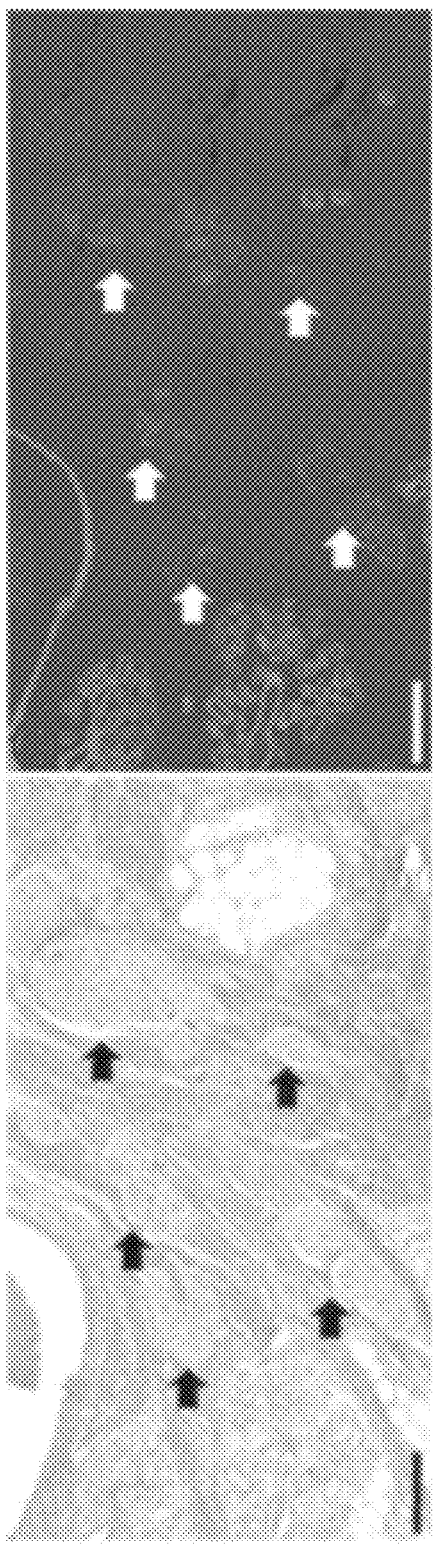
FIG. 11A  FIG. 11B  FIG. 11C  FIG. 11D

Kit Components:
A – Vial of collagen solution
B – Vial of self-assembly reagent
C – Two Syringes
D – Large needle-free vial adapter
E – Small needle-free vial adapter
F – Luer lock connector
G – Applicator tip

BIOLOGIC FILLER FOR RESTORING AND REGENERATING TISSUE

RELATED APPLICATIONS

This application is a U. S. continuation patent application based on PCT/US2021/015277, filed Jan. 27, 2021. PCT/US2021/015277 claims the benefit of U.S. Provisional Application No. 62/966,398, filed Jan. 27, 2020, and U.S. Provisional Application No. 63/015,946, filed Apr. 27, 2020. The entire contents of each of these documents are incorporated herein by reference, except that in the event of any inconsistent disclosure or definition from the present specification, the disclosure or definition herein shall be deemed to prevail.

TECHNICAL FIELD

The present teachings relate generally to methods for treating tissue voids and defects with a tissue filler for restoring and regenerating tissue, and to compositions and kits therefore.

BACKGROUND

Breast cancer is the most commonly diagnosed cancer in women with over 2 million new cases ever year worldwide and approximately 330,000 per year in the US alone. It is estimated that 60-70% (~1.3 million globally) of these cases are treated with breast conserving surgery (BCS; otherwise known as lumpectomy), which represents the standard of care for early-stage breast cancer. Conventional BCS involves removal of the tumor along with a cancer-free margin of healthy tissue (negative margins), through a small, cosmetically placed incision. BCS with adjunct radiation is preferred over full mastectomy (i.e., removal of the whole breast) for eligible patients, because it yields equivalent survival while preserving patients' breasts and reduces surgery time, recovery time, and complications. Since breast cancer survival rates are relatively high (~90%), long-term outcomes and survivorship are especially important for treatment of this disease. Specifically for BCS, complete removal of cancerous tissue (obtaining negative margins) and preservation of breast shape, appearance and consistency (i.e., pleasing breast cosmesis) in a single surgery are paramount to achieving satisfactory outcomes and patient quality of life.

One of the major challenges with BCS is excision of sufficient tissue so to remove all of the cancer while maintaining an acceptable cosmetic outcome. Standard practice guidelines for BCS involve "closing the excision (surgical) defect in layers as cosmetically as possible" following resection of the tumor. Healing of the complex surgical wound then follows, with the tissue void left behind filling with serous fluid and/or blood to initially form a seroma or hematoma followed by scar formation and contraction. For surgeons, it is extremely challenging, if not impossible, to predict the cosmetic outcome of BCS, especially given significant patient variation in breast tumor size, shape, and location, and the unpredictable nature of the tissue repair process, which is compounded by the effects of adjunct radiation therapy. Because of this, there remains a relatively high level of BCS-related breast deformities, with approximately one-third of women experiencing unsatisfactory cosmesis (e.g., dents, distortions, and asymmetry between breasts). Such outcomes have ultimately been shown to decrease overall quality of life for breast cancer survivors, with increased breast pain and discomfort owing to scar formation and contraction, feelings of depression, insecurity, and anxiety, and negative impact on self-esteem, body image, and intimacy. Further, the need for secondary surgical procedures (e.g., re-excisions for tumor left behind and revisions/reconstruction procedures to repair divots/deformities) remain high for BCS, with estimates ranging from 20-40%. This includes re-excisions due to positive margins as well as revision and reconstruction procedures to repair breast deformities. Altogether, due to these poor outcomes and complications, it is estimated that repeat surgeries after initial BCS increase healthcare cost by $16,000 or more, on average, per additional procedure. Based on these challenges and concerns, BCS may not be an option for all women, especially those with tumors that are large in comparison to breast size (>5 cm in diameter; tumor:breast volume percent greater than 1.5%) or those within the lower quadrants of the breast. Therefore, breast surgeons are in need of new therapeutic options to further optimize oncologic and cosmetic outcomes of BCS, enabling them to confidently extend this conservative therapy to more patients with desirable outcomes.

At present, there is no extra tissue products that allow surgeons to predictably restore, reconstruct, or regenerate tissues, such as the breast. Furthermore, it is apparent that surgeons are actively looking for solutions to this problem. Specifically, many surgeons have attempted to use a relatively new, three-dimensional spiral-shaped tumor bed bioresorbable marker called BioZorb, which is primarily intended to mark the surgical cavity or lumpectomy defect for targeted, post-operative adjunct radiation therapy. Breast surgeons have applied this implantable device with hopes that it would not only serve as a marker but also fill the tissue void and improve cosmetic results. However, both surgeons and patients have been uniformly dissatisfied with BioZorb, especially since it gives rise to a hard, palpable implant that lasts for up to 2.8 years and increases patient pain and discomfort. Additionally, surgeons have indicated that it is expensive relative to other radiation markers and does not significantly improve outcomes.

On the other hand, there are two experimental surgical reconstruction options, namely autologous fat grafting (also known as lipofilling or fat transfer) and oncoplastic surgery, which aim to improve BCS cosmetic outcomes and potentially expand BCS-eligible patient populations. Fat grafting involves harvesting fat (adipose tissue) via liposuction from one area of the body and re-injecting the minimally processed fat tissue into another region (e.g., a tissue void). Originally, fat grafting was used for delayed breast reconstruction procedures, but more recently, it has been investigated for use immediately following BCS. Problems with this approach include rapid reabsorption leading to significant volume loss (ranging from 25% to 80%), fat necrosis, oil cyst formation, microcalcifications, and questions around oncologic safety (i.e., cancer recurrence). On the other hand, oncoplastic surgery combines the skills of surgical oncology and plastic surgery to perform breast reconstruction at the time of lumpectomy. Oncoplastic procedures include both volume displacement (rearrangement of remaining healthy breast tissue) and volume replacement (reconstruction with various autologous tissue flaps) techniques. While both surgical reconstruction procedures offer the advantage of using the patient's own tissue and have seen some success, they require specialized training, often multiple surgeon involvement, and longer surgical procedures, thus limiting their availability and increasing costs. At present, these techniques have yet to receive widespread adoption because of the specialized training that is necessary and remaining concerns over sacrificing oncological safety and effectiveness for improved cosmesis.

SUMMARY

In accordance with the present teachings, a restorative and regenerative tissue filler is described that may be applied as a liquid to any type of tissue void or defect-including but not limited to tissue voids resulting from surgical wounds (e.g., including but not limited to surgical wounds stemming from BCS), physical defects (e.g., scars, divots, congenital defects, etc.), injuries, disease progressions, and/or the like-prior to transitioning to a fibrillar collagen matrix with tissue consistency.

As described herein, the inventors have developed a flowable tissue filler comprising in-situ polymerizable oligomeric collagen and a neutralization (self-assembly) buffer. After the liquid collagen and neutralization buffer are mixed, the neutralized collagen solution may be used to fill tissue voids (e.g., surgical wounds) or defects, including those that are deep and/or difficult to access and irregularly-shaped tissue voids. Upon application, the applied solution undergoes rapid (~1 minute at body temperature) fibril formation via molecular self-assembly. The resulting tissue filler matrix restores and maintains tissue shape and tissue consistency over time and elicits a tissue-implant response characterized by cellularization, vascularization, and new tissue formation without evoking an inflammatory response that is typically observed with wound healing or a foreign body reaction that is typically observed with conventional tissue-implant responses.

In some embodiments, a tissue filler in accordance with the present teachings may provide one or more of the following advantages: (1) reduced (i.e., relative to conventional no-fill procedures) or no scar tissue formation; (2) reduced (i.e., relative to conventional no-fill procedures) or no defect contraction; (3) reduced (i.e., relative to conventional no-fill procedures) or no inflammatory mediators or inflammatory response; (4) a tissue consistency that is similar to that of natural tissue (e.g., a compressive modulus or range of compressive moduli that is similar to that of natural tissue); (5) restoration and generation of breast tissue with adipose tissue, mammary gland tissue, etc.; (6) restoration and generation of skeletal muscle; (7) tissue-implant response that does not interfere with routine clinical procedures including re-excision, ultrasonography, or radiography; and/or (8) tissue-implant response that is less (i.e., relative to conventional procedures) or not negatively impacted by adjunct radiation (e.g., reduced or no lipid cysts, microcalcifications, focal masses, and/or areas of increased opacity, any of which may interfere with imaging).

In some embodiments, a method for filling a tissue void or defect in accordance with the present teachings includes (a) introducing into the tissue void or defect a self-assembling biopolymer, and (b) polymerizing the self-assembling biopolymer to form a shape-retaining matrix.

In some embodiments, a method for filling a tissue void or defect generated by a lumpectomy or mastectomy procedure in accordance with the present teachings includes (a) introducing into the tissue void or defect a mixture containing an oligomeric collagen solution and a neutralization solution; and (b) polymerizing the oligomeric collagen solution to form a collagen-fibril matrix. The oligomeric collagen solution may include a lyophilized type I oligomeric collagen and an acid.

In some embodiments, a method for filling a tissue void or defect generated by a lumpectomy or mastectomy procedure includes (a) introducing into the tissue void or defect a mixture containing an oligomeric collagen solution and a neutralization solution; and (b) polymerizing the oligomeric collagen solution to form a collagen-fibril matrix. In some embodiments, the oligomeric collagen solution may include a lyophilized type I oligomeric collagen and 0.01 N hydrochloric acid. In some embodiments, a concentration of the oligomeric collagen solution is about 8 mg/mL based on a dry weight of the lyophilized type I oligomeric collagen. In some embodiments, a ratio of the oligomeric collagen solution to the neutralization solution is about 9:1.

In other embodiments, a collagen matrix prepared according to any of the above-described methods is provided. In further embodiments, a kit containing a collagen composition and a buffer solution is provided. In further embodiments, a kit containing lyophilized type I oligomeric collagen, a hydrochloric acid solution, and a buffer solution is provided. In further embodiments, one or more therapeutic agents-including but not limited to chemotherapeutic agents, anti-inflammatory agents, antibiotic agents, analgesic agents, and/or the like, and combinations thereof-admissible with the collagen matrix are provided, such that the one or more therapeutic agents are configured for delivery within a matrix at the site of a tissue void or defect. In some embodiments, the one or more therapeutic agents are configured for localized delivery within a matrix at the site of a tissue void or defect.

Additional features and advantages of the present teachings may be described by the embodiments set forth in any of the following enumerated clauses. It is to be understood that any of the embodiments described herein may be used in connection with any other embodiments described herein to the extent that the embodiments do not contradict one another. Thus, any applicable combination of the following enumerated clauses is also contemplated.

1. A method for filling a tissue void or defect in a patient, the method comprising: introducing into the tissue void or defect a self-assembling biopolymer; and polymerizing the self-assembling biopolymer to form a shape-retaining matrix.
2. The method of clause 1 wherein the self-assembling biopolymer comprises in situ polymerizable oligomeric collagen.
3. The method of any preceding clause wherein the in-situ polymerizable oligomeric collagen comprises collagen molecules.
4. The method of any preceding clause wherein at least a portion of the collagen molecules are covalently bonded by one or a plurality of intermolecular cross-links.
5. The method of any preceding clause wherein the patient is a mammal.
6. The method of any preceding clause wherein the patient is a human.
7. The method of any preceding clause wherein the introducing is achieved under aseptic conditions.
8. The method of any preceding clause wherein the self-assembling biopolymer comprises in-situ polymerizable collagen, and wherein the shape-retaining matrix comprises a collagen-fibril matrix.
9. The method of any preceding clause wherein the self-assembling biopolymer comprises a liquid type I collagen.

10. The method of any preceding clause wherein the self-assembling biopolymer comprises a type I oligomeric collagen derived from porcine dermis.
11. The method of any preceding clause wherein the self-assembling biopolymer comprises a solution comprising a lyophilized type I oligomeric collagen and an acid.
12. The method of any preceding clause wherein the self-assembling biopolymer comprises a solution comprising a lyophilized type I oligomeric collagen and hydrochloric acid.
13. The method of any preceding clause wherein the self-assembling biopolymer comprises a solution comprising a lyophilized type I oligomeric collagen and hydrochloric acid, and wherein the solution further comprises a buffer solution.
14. The method of any preceding clause wherein the self-assembling biopolymer comprises an oligomeric collagen solution and a buffer solution, wherein the oligomeric collagen solution comprises a lyophilized type I oligomeric collagen and an acid.
15. The method of any preceding clause wherein the self-assembling biopolymer comprises an oligomeric collagen solution and a buffer solution, wherein the oligomeric collagen solution comprises a lyophilized type I oligomeric collagen and an acid, and wherein a ratio of the oligomeric collagen solution to the buffer solution is about 9:1.
16. The method of any preceding clause wherein the self-assembling biopolymer comprises a solution comprising a lyophilized type I oligomeric collagen and 0.01 N hydrochloric acid, wherein a concentration of the solution is about 8 mg/mL based on a dry weight of the lyophilized type I oligomeric collagen.
17. The method of any preceding clause wherein the self-assembling biopolymer comprises a solution comprising a lyophilized type I oligomeric collagen and hydrochloric acid, wherein the solution has been clarified using ultracentrifugation.
18. The method of any preceding clause wherein the self-assembling biopolymer comprises a solution comprising a lyophilized type I oligomeric collagen and hydrochloric acid, wherein the solution has been clarified using ultracentrifugation and then filtered through a sterile membrane filter.
19. The method of any preceding clause wherein the self-assembling biopolymer comprises a solution comprising a lyophilized type I oligomeric collagen and hydrochloric acid, wherein the solution has been clarified using ultracentrifugation, dosed with ultraviolet radiation, and then filtered through a sterile membrane filter.
20. The method of any preceding clause wherein the self-assembling biopolymer comprises a solution comprising a lyophilized type I oligomeric collagen and hydrochloric acid, wherein the solution has been clarified using ultracentrifugation, dosed with 500 mJ/cm$^2$ ultraviolet radiation, and then filtered through a sterile membrane filter.
21. The method of any preceding clause wherein the introducing comprising injecting the self-assembling biopolymer into the tissue void or defect via a syringe.
22. The method of any preceding clause wherein the tissue void or defect is generated by a lumpectomy procedure.
23. The method of any preceding clause wherein the tissue void or defect is generated by a mastectomy procedure.
24. The method of any preceding clause wherein the filling of the tissue void or defect does not result in defect contraction or scar tissue formation.
25. The method of any preceding clause wherein the filling of the tissue void or defect does not result in an inflammatory mediator, an inflammatory response, or a foreign body reaction.
26. The method of any preceding clause wherein the filling of the tissue void or defect results in a compressive modulus or range of compressive moduli substantially identical to that of natural tissue.
27. The method of any preceding clause wherein the filling of the tissue void or defect results in generation of breast tissue with adipose tissue, mammary gland tissue, or a combination thereof.
28. The method of any preceding clause wherein a tissue-implant response to the filling of the tissue void or defect is not negatively impacted by radiation, such that one or more of lipid cysts, microcalcifications, focal masses, and/or areas of increased opacity are not observed.
29. A method for filling a tissue void or defect in a patient, the tissue void or defect generated by a lumpectomy or mastectomy procedure, the method comprising: introducing into the tissue void or defect a mixture comprising an oligomeric collagen solution and a buffer solution; and polymerizing the oligomeric collagen solution to form a collagen-fibril matrix; wherein the oligomeric collagen solution comprises a lyophilized type I oligomeric collagen and an acid.
30. The method of clause 29 wherein a ratio of the oligomeric collagen solution to the buffer solution is about 9:1.
31. The method of clause 29 or clause 30 wherein the acid comprises 0.01 N hydrochloric acid and wherein a concentration of the oligomeric collagen solution is about 8 mg/mL based on a dry weight of the lyophilized type I oligomeric collagen.
32. A method for filling a tissue void or defect in a patient, the tissue void or defect generated by a lumpectomy or mastectomy procedure, the method comprising: introducing into the tissue void or defect a mixture comprising an oligomeric collagen solution and a buffer solution; and polymerizing the oligomeric collagen solution to form a collagen-fibril matrix; wherein the oligomeric collagen solution comprises a lyophilized type I oligomeric collagen and 0.01 N hydrochloric acid; wherein a concentration of the oligomeric collagen solution is about 8 mg/mL based on a dry weight of the lyophilized type I oligomeric collagen; and wherein a ratio of the oligomeric collagen solution to the buffer solution is about 9:1.
33. The method of clause 32 wherein the oligomeric collagen solution has been clarified using ultracentrifugation, filtered through a sterile membrane filter, dosed with ultraviolet radiation, or a combination thereof.
34. The method of any one of clauses 32-33 wherein the tissue void or defect comprises a wound.
35. The method of any one of clauses 32-34 wherein the tissue void or defect comprises a surgical wound.
36. The method of any one of clauses 32-35 wherein the tissue void or defect resulted from removal of a tumor.

37. The method of any one of clauses 32-36 wherein the tissue void or defect resulted from removal of a breast tumor.
38. The method of any one of clauses 32-37 wherein the self-assembling biopolymer comprises a tissue filler.
39. The method of any one of clauses 32-38 wherein the filling of the tissue void or defect does not result in defect contraction or scar tissue formation.
40. The method of any one of clauses 32-39 wherein the filling of the tissue void or defect does not result in an inflammatory mediator, an inflammatory response, or a foreign body reaction.
41. The method of any one of clauses 32-40 wherein the filling of the tissue void or defect results in a compressive modulus or range of compressive moduli substantially identical to that of natural tissue.
42. The method of any one of clauses 32-41 wherein the filling of the tissue void or defect results in generation of breast tissue with adipose tissue, mammary gland tissue, or a combination thereof.
43. The method of any one of clauses 32-42 wherein a tissue-implant response to the filling of the tissue void or defect is not negatively impacted by radiation, such that one or more of lipid cysts, microcalcifications, focal masses, and/or areas of increased opacity are not observed.
44. A method for filling a wound, the method comprising: introducing into the wound a mixture comprising an oligomeric collagen solution and a buffer solution; and polymerizing the oligomeric collagen solution to form a collagen-fibril matrix; wherein the oligomeric collagen solution comprises a lyophilized oligomeric collagen and an acid.
45. The method of clause 44 wherein the lyophilized oligomeric collagen comprises lyophilized type I oligomeric collagen.
46. The method of clause 44 or clause 45 wherein the wound comprises a surgical wound.
47. The method of any one of clauses 44-46 wherein the surgical wound resulted from removal of a tumor.
48. The method of any one of clauses 44-47 wherein the surgical wound resulted from removal of a breast tumor.
49. The method of any one of clauses 44-48 wherein the oligomeric collagen solution comprises a tissue filler.
50. The method of any one of clauses 44-49 wherein the filling of the wound does not result in defect contraction and scar tissue formation.
51. The method of any one of clauses 44-50 wherein the filling of the wound does not result in an inflammatory mediator, an inflammatory response, or a foreign body reaction.
52. The method of any one of clauses 44-51 wherein the filling of the wound results in a compressive modulus or range of compressive moduli substantially identical to that of natural tissue.
53. The method of any one of clauses 44-52 wherein the filling of the wound results in generation of breast tissue with adipose tissue, mammary gland tissue, or a combination thereof.
54. The method of any one of clauses 44-53 wherein a tissue-implant response to the filling of the wound is not negatively impacted by radiation, such that one or more of lipid cysts, microcalcifications, focal masses, and/or areas of increased opacity are not observed.
55. A method for restoring and regenerating skeletal muscle tissue in a tissue void or defect of a patient, the method comprising: introducing into the tissue void or defect a self-assembling biopolymer; and polymerizing the self-assembling biopolymer to form a shape-retaining matrix.
56. The method of clause 55 wherein the tissue void or defect comprises a wound.
57. The method of clause 55 or clause 56 wherein the tissue void or defect comprises a surgical wound.
58. The method of any one of clauses 55-57 wherein the tissue void or defect resulted from removal of a tumor.
59. The method of any one of clauses 55-58 wherein the restoring and regenerating of the skeletal muscle tissue in the tissue void or defect does not result in defect contraction or scar tissue formation.
60. The method of any one of clauses 55-59 wherein the restoring and regenerating of the skeletal muscle tissue in the tissue void or defect does not result in an inflammatory mediator, an inflammatory response, or a foreign body reaction.
61. The method of any one of clauses 55-60 wherein the restoring and regenerating of the skeletal muscle tissue in the tissue void or defect results in a compressive modulus or range of compressive moduli substantially identical to that of natural tissue.
62. The method of any one of clauses 55-61 wherein the restoring and regenerating of the skeletal muscle tissue in the tissue void or defect results in generation of skeletal muscle with adipose tissue.
63. The method of any one of clauses 55-62 wherein a tissue-implant response to the restoring and regenerating of the skeletal muscle tissue is not negatively impacted by radiation, such that one or more of lipid cysts, microcalcifications, focal masses, and/or areas of increased opacity are not observed.
64. A method for restoring and regenerating skeletal muscle tissue in a tissue void or defect, the method comprising: introducing into the tissue void or defect a mixture comprising an oligomeric collagen solution and a buffer solution; and polymerizing the oligomeric collagen solution to form a collagen-fibril matrix; wherein the oligomeric collagen solution comprises a lyophilized type I oligomeric collagen and an acid.
65. The method of clause 64 wherein the tissue void or defect comprises a wound.
66. The method of clause 64 or clause 65 wherein the tissue void or defect comprises a surgical wound.
67. The method of any one of clauses 64-66 wherein the tissue void or defect resulted from removal of a tumor.
68. The method of any one of clauses 64-67 wherein the restoring and regenerating of the skeletal muscle tissue in the tissue void or defect does not result in defect contraction or scar tissue formation.

The method of any one of clauses 64-68 wherein storing and regenerating of the skeletal muscle tissue in the tissue void or defect does not result in an inflammatory mediator, an inflammatory response, or a foreign body reaction.

70. The method of any one of clauses 64-69 wherein the restoring and regenerating of the skeletal muscle tissue in the tissue void or defect results in a compressive modulus or range of compressive moduli substantially identical to that of natural tissue.
71. The method of any one of clauses 64-70 wherein the restoring and regenerating of the skeletal muscle tissue in the tissue void or defect results in generation of skeletal muscle with adipose tissue.
72. The method of any one of clauses 64-71 wherein a tissue-implant response to the restoring and regenerating of the skeletal muscle tissue is not negatively impacted by radiation, such that one or more of lipid cysts, microcalcifications, focal masses, and/or areas of increased opacity are not observed.

73. A method for preparing a matrix in a tissue void or defect, the method comprising polymerizing collagen using a single mixing step, the single mixing step comprising mixing a collagen composition with a buffer solution to form a collagen solution, wherein the collagen in the collagen solution polymerizes to form the matrix.

74. The method of clause 73 further comprising incubating the collagen solution at a temperature of greater than about 25° C. to promote polymerization of the collagen in the collagen solution.

75. The method of clause 73 or clause 74 further comprising incubating the collagen solution at a temperature of about 37° C. to promote polymerization of the collagen in the collagen solution.

76. The method of any one of clauses 73-75 wherein the collagen comprises collagen oligomers.

77. The method of any one of clauses 73-76 wherein the collagen comprises collagen molecules.

78. The method of any one of clauses 73-77 wherein the collagen consists of collagen oligomers.

79. The method of any one of clauses 73-78 wherein the collagen consists of intermolecularly cross-linked collagen molecules.

80. The method of any one of clauses 73-79 wherein the collagen consists essentially of intermolecularly cross-linked collagen molecules.

81. The method of any one of clauses 73-80 wherein the collagen further comprises telocollagen.

82. The method of any one of clauses 73-81 wherein the collagen further comprises atelocollagen.

83. The method of any one of clauses 73-82 wherein the collagen comprising collagen oligomers is obtained from a tissue containing collagen oligomers, from cells producing collagen oligomers, or by chemically cross-linking collagen to obtain the collagen oligomers.

84. The method of any one of clauses 73-83 wherein the collagen is derived from porcine skin tissue.

85. The method of any one of clauses 73-84 wherein the collagen composition further comprises an acid.

86. The method of any one of clauses 73-85 wherein the acid is selected from the group consisting of hydrochloric acid, acetic acid, lactic acid, formic acid, citric acid, sulfuric acid, and phosphoric acid.

87. The method of any one of clauses 73-86 wherein the acid is hydrochloric acid.

88. The method of any one of clauses 73-87 wherein the hydrochloric acid is about 0.005 N to about 0.1 N hydrochloric acid.

89. The method of any one of clauses 73-88 wherein the hydrochloric acid is about 0.01 N hydrochloric acid.

90. The method of any one of clauses 73-89 wherein a concentration of the collagen in the collagen solution is about 0.1 mg/ml to about 40 mg/mL.

91. The method of any one of clauses 73-90 wherein a concentration of the collagen in the collagen solution is about 7 mg/mL to about 8 mg/mL.

92. The method of any one of clauses 73-91 wherein a concentration of the collagen in the mixture of the collagen solution and the buffer solution is about 6.3 to about 7.2 mg/mL.

93. The method of any one of clauses 73-92 wherein the collagen composition is sterilized.

94. The method of any one of clauses 73-93 wherein the collagen composition, the collagen solution, or the collagen matrix is sterilized by a method selected from the group consisting of exposure to chloroform, viral filtration, sterile filtration, gamma irradiation, ultraviolet radiation, E-beam, and combinations thereof.

95. The method of any one of clauses 73-94 wherein the collagen composition is sterilized by filtration.

96. The method of any one of clauses 73-95 wherein the buffer solution comprises about 0.03 mM to about 0.2 mM $MgCl_2$.

97. The method of any one of clauses 73-96 wherein the buffer solution comprises about 0.002 mM to about 0.02 mM $MgCl_2$.

98. The method of any one of clauses 73-97 wherein the buffer solution comprises less than about 0.02 mM $MgCl_2$.

99. The method of any one of clauses 73-98 wherein buffer solution does not comprise $MgCl_2$.

100. The method of any one of clauses 73-99 wherein the buffer solution further comprises about 0.3 mM to about 3 mM $KH_2PO_4$.

101. The method of any one of clauses 73-100 wherein the buffer solution further comprises about 1 mM to about 10 M $Na_2HPQ_4$.

102. The method of any one of clauses 73-101 wherein the buffer solution further comprises about 0.1 mM to about 4 mM KCl.

103. The method of any one of clauses 73-102 wherein the buffer solution further comprises about 0.02 M to about 0.3 M NaCl.

104. The method of any one of clauses 73-103 wherein the buffer solution further comprises about 0.002 N to about 0.02 N NaOH.

105. The method of any one of clauses 73-104 wherein the buffer solution further comprises about 0.5 weight percent to about 5 weight percent of glucose.

106. The method of any one of clauses 73-105 wherein the buffer solution comprises about 0.5 weight percent glucose or less.

107. The method of any one of clauses 73-106 wherein the buffer solution does not comprise glucose.

108. The method of any one of clauses 73-107 further comprising adding cells to the collagen solution.

109. The method of any one of clauses 73-108 wherein the matrix comprises collagen fibrils.

110. The method of any one of clauses 73-109 wherein the collagen is soluble collagen.

111. The method of any one of clauses 73-110 wherein the collagen composition, the collagen solution, and/or the matrix is sterilized using UVC irradiation.

112. The method of any one of clauses 73-111 wherein the collagen composition the collagen solution, and/or the matrix is sterilized using UVC irradiation and sterile filtration.

113. The method of any one of clauses 73-112 wherein the matrix that results from polymerization of the collagen solution maintains a polymerization property relative to a collagen composition this is not irradiated or to lyophilized collagen that is not irradiated, respectively.

114. The method of any one of clauses 73-113 wherein the polymerization property is shear storage modulus.

115. The method of any one of clauses 73-114 wherein a dose of the radiation ranges from about 5 $mJ/cm^2$ to about 800 $mJ/cm^2$.

116. The method of any one of clauses 73-115 wherein a dose of the radiation dose ranges from about 30 mJ/cm$^2$ to about 300 mJ/cm$^2$.

117. The method of any one of clauses 73-116 wherein sterilization inactivates viruses.

118. A method for preparing a matrix in a tissue defect or void site, said method comprising polymerizing collagen by mixing a collagen composition with a buffer solution to form a collagen solution, and polymerizing the collagen in the collagen solution to form the matrix wherein the buffer solution does not contain magnesium ions or manganese ions.

119. The method of clause 118 further comprising incubating the collagen solution at a temperature of greater than about 25° C. to promote polymerization of the collagen in the collagen solution.

120. The method of clause 118 or clause 119 further comprising incubating the collagen solution at a temperature of about 37° C. to promote polymerization of the collagen in the collagen solution.

121. The method of any one of clauses 118-120 wherein the collagen comprises collagen oligomers.

122. The method of any one of clauses 118-121 wherein the collagen comprises collagen molecules.

123. The method of any one of clauses 118-122 wherein the collagen consists of collagen oligomers.

124. The method of any one of clauses 118-123 wherein the collagen consists of intermolecularly cross-linked collagen molecules.

125. The method of any one of clauses 118-124 wherein the collagen consists essentially of intermolecularly cross-linked collagen molecules.

126. The method of any one of clauses 118-125 wherein the collagen further comprises telocollagen.

127. The method of any one of clauses 118-126 wherein the collagen further comprises atelocollagen.

128. The method any one of clauses 118-127 wherein the collagen comprising collagen oligomers is obtained from a tissue containing collagen oligomers, from cells producing collagen oligomers, or by chemically cross-linking collagen to obtain the collagen oligomers.

129. The method of any one of clauses 118-128 wherein the collagen is derived from porcine skin tissue.

130. The method any one of clauses 118-129 wherein the collagen composition further comprises an acid.

131. The method of any one of clauses 118-130 wherein the acid is selected from the group consisting of hydrochloric acid, acetic acid, lactic acid, formic acid, citric acid, sulfuric acid, and phosphoric acid.

132. The method of any one of clauses 118-131 wherein the acid is hydrochloric acid.

133. The method of any one of clauses 118-132 wherein the hydrochloric acid is about 0.005 N to about 0.1 N hydrochloric acid.

134. The method of any one of clauses 118-133 wherein the hydrochloric acid is about 0.01 N hydrochloric acid.

135. The method of any one of clauses 118-134 wherein a concentration of the collagen in the collagen solution is about 0.1 mg/ml to about 40 mg/ml.

136. The method of any one of clauses 118-135 wherein a concentration of the collagen in the collagen solution is about 7 mg/mL to about 8 mg/mL.

137. The method of any one of clauses 118-136 wherein a concentration of the collagen in the mixture of the collagen solution and the buffer solution is about 6.3 to about 7.2 mg/mL.

138. The method of any one of clauses 118-137 wherein the collagen composition is sterilized.

139. The method of any one of clauses 118-138 wherein the collagen composition, the collagen solution, or the collagen matrix is sterilized by a method selected from the group consisting of exposure to chloroform, viral filtration, sterile filtration, gamma irradiation, ultraviolet radiation, E-beam, and combinations thereof.

140. The method of any one of clauses 118-139 wherein collagen composition is sterilized by filtration.

141. The method of any one of clauses 118-140 wherein the buffer solution comprises about 0.03 mM to about 0.2 mM MgCl$_2$.

142. The method of 141 wherein the buffer solution comprises about 0.002 mM to about 0.02 mM MgCl$_2$.

143. The method of any one of clauses 118-142 wherein the buffer solution comprises less than about 0.02 mM MgCl$_2$.

144. The method of any one of clauses 118-143 wherein the buffer solution does not comprise MgCl$_2$.

145. The method of any one of clauses 118-144 wherein the buffer solution further comprises about 0.3 mM to about 3 mM KH$_2$PO$_4$.

146. The method of any one of clauses 118-145 wherein the buffer solution further comprises about 1 mM to about 10 M Na$_2$HPO$_4$.

147. The method of any one of clauses 118-146 wherein the buffer solution further comprises about 0.1 mM to about 4 mM KCl.

148. The method of any one of clauses 118-147 wherein the buffer solution further comprises about 0.02 M to about 0.3 M NaCl.

149. The method of any one of clauses 118-148 wherein the buffer solution further comprises about 0.002 N to about 0.02 N NaOH.

150. The method of any one of clauses 118-149 wherein the buffer solution further comprises about 0.5 weight percent to about 5 weight percent of glucose.

151. The method of any one of clauses 118-150 wherein the buffer solution comprises about 0.5 weight percent glucose or less.

152. The method of any one of clauses 118-151 wherein the buffer solution does not comprise glucose.

153. The method of any one of clauses 118-152 further comprising adding cells to the collagen solution.

154. The method of any one of clauses 118-153 wherein the matrix comprises collagen fibrils.

155. The method of any one of clauses 118-154 wherein the collagen is soluble collagen.

156. The method of any one of clauses 118-155 wherein the collagen composition, the collagen solution, and/or the collagen matrix is sterilized using ultraviolet radiation.

157. The method of any one of clauses 118-156 wherein the collagen composition, the collagen solution, and/or the matrix is sterilized using UVC irradiation and sterile filtration.

158. The method of any one of clauses 118-157 wherein the matrix that results from polymerization of the collagen solution maintains a polymerization property relative to a collagen composition this is not irradiated or to lyophilized collagen that is not irradiated, respectively.

159. The method of any one of clauses 118-158 wherein the polymerization property is shear storage modulus.

160. The method of any one of clauses 118-159 wherein a dose of the radiation ranges from about 5 mJ/cm² to about 800 mJ/cm².
161. The method of any one of clauses 118-160 wherein a dose of the radiation dose ranges from about 30 mJ/cm² to about 300 mJ/cm².
162. The method of any one of clauses 118-161 wherein sterilization inactivates viruses.
163. A collagen matrix prepared according to the method of any one of clauses 1-162.
164. The collagen matrix of clause 163 wherein the collagen matrix is a medical graft.
165. The collagen matrix of clause 163 or clause 164 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.
166. The collagen matrix of any one of clauses 163-165 wherein the collagen matrix is used for research purposes.
167. The collagen matrix of any one of clauses 163-166 wherein the collagen matrix is used for drug toxicity testing or drug development.
168. The collagen matrix of any one of clauses 163-167 wherein the collagen matrix is sterilized using ultraviolet radiation.
169. The collagen matrix of any one of clauses 163-168 wherein the collagen matrix maintains a polymerization property relative to a collagen matrix that is not irradiated.
170. The collagen matrix of any one of clauses 163-169 wherein the polymerization property is shear storage modulus.
171. The collagen matrix of any one of clauses 163-170 wherein the radiation dose ranges from about 5 mJ/cm² to about 800 mJ/cm².
172. The collagen matrix of any one of clauses 163-171 wherein the radiation dose ranges from about 30 mJ/cm² to about 300 mJ/cm².
173. The collagen matrix of any one of clauses 163-172 wherein the sterilization inactivates viruses.
174. The collagen matrix of any one of clauses 163-173 wherein the collagen matrix is sterilized using UVC irradiation.
175. The collagen matrix of any one of clauses 163-174 wherein the collagen matrix is sterilized using UVC irradiation and sterile filtration.
176. A collagen matrix prepared by introducing into a tissue void or defect a self-assembling biopolymer, and polymerizing the self-assembling biopolymer to form a shape-retaining matrix, wherein a pH of the self-assembling biopolymer ranges from about 5.5 to about 8.5, wherein a self-assembly time of the self-assembling biopolymer ranges from about 0.2 minutes to about 1.5 minutes, wherein a shear storage modulus (G') of the collagen matrix ranges from about 2.0 kPa to about 4.0 kPa, wherein a shear loss modulus (G") of the collagen matrix ranges from about 0.1 kPa to about 0.7 kPa, and wherein a compression modulus of the collagen matrix ranges from about 5.0 kPa to about 10.0 kPa.
177. The collagen matrix of clause 176 wherein the pH of the self-assembling biopolymer is about 7.25±about 0.25, wherein the self-assembly time of the self-assembling biopolymer is about 0.8 minutes±about 0.3 minutes, wherein the shear storage modulus (G') of the collagen matrix is about 3.1 kPa±about 0.4 kPa, wherein the shear loss modulus (G") of the collagen matrix is about 0.4 kPa±about 0.1 kPa, and wherein the compression modulus of the collagen matrix is about 7.7 kPa±about 1.9 kPa.
178. The collagen matrix of clause 176 or clause 177 wherein the collagen matrix is a medical graft.
179. The collagen matrix of any one of clauses 176-178 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.
180. The collagen matrix of any one of clauses 176-179 wherein the collagen matrix is used for research purposes.
181. The collagen matrix of any one of clauses 176-180 wherein the collagen matrix is used for drug toxicity testing or drug development.
182. The collagen matrix of any one of clauses 176-181 wherein the collagen matrix is sterilized using ultraviolet radiation.
183. The collagen matrix of any one of clauses 176-182 wherein the collagen matrix maintains a polymerization property relative to a collagen matrix that is not irradiated.
184. The collagen matrix of any one of clauses 176-183 wherein the polymerization property is shear storage modulus.
185. The collagen matrix of any one of clauses 176-184 wherein the radiation dose ranges from about 5 mJ/cm² to about 800 mJ/cm².
186. The collagen matrix of any one of clauses 176-185 wherein the radiation dose ranges from about 30 mJ/cm² to about 300 mJ/cm².
187. The collagen matrix of any one of clauses 176-186 wherein the sterilization inactivates viruses.
188. The collagen matrix of any one of clauses 176-187 wherein the collagen matrix is sterilized using UVC irradiation.
189. The collagen matrix of any one of clauses 176-188 wherein the collagen matrix is sterilized using UVC irradiation and sterile filtration.
190. A kit for restoring and regenerating tissue in a tissue void or defect, the kit comprising an in-situ polymerizable collagen composition and a buffer solution.
191. The kit of clause 190 wherein the in-situ polymerizable collagen composition comprises a liquid type I collagen.
192. The kit of clause 190 or clause 191 wherein the in-situ polymerizable collagen composition comprises a type I oligomeric collagen derived from porcine dermis.
193. The kit of any one of clauses 190-192 wherein the in-situ polymerizable collagen composition comprises a solution comprising a lyophilized oligomeric collagen and an acid.
194. The kit of any one of clauses 190-193 wherein the in-situ polymerizable collagen composition comprises a solution comprising a lyophilized type I oligomeric collagen and an acid.
195. The kit of any one of clauses 190-194 wherein the in-situ polymerizable collagen composition comprises a solution comprising a lyophilized type I oligomeric collagen and hydrochloric acid.

196. The kit of any one of clauses 190-195 wherein a ratio of the in-situ polymerizable collagen composition to the buffer solution is about 9:1.
197. The kit of any one of clauses 190-196 wherein the in-situ polymerizable collagen composition comprises a solution comprising a lyophilized type I oligomeric collagen and 0.01 N hydrochloric acid, and wherein a concentration of the collagen the solution of the in-situ polymerizable collagen composition is about 8 mg/mL based on a dry weight of the lyophilized type I oligomeric collagen.
198. The kit of any one of clauses 190-197 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation.
199. The kit of any one of clauses 190-198 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation and then filtered through a sterile membrane filter.
200. The kit of any one of clauses 190-199 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation, dosed with ultraviolet radiation, and then filtered through a sterile membrane filter.
201. The kit of any one of clauses 190-200 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation, dosed with 500 $mJ/cm^2$ ultraviolet radiation, and then filtered through a sterile membrane filter.
202. The kit of any one of clauses 190-201 further comprising a syringe configured for delivery of a mixture of the in-situ polymerizable collagen composition and the buffer solution to the tissue void or defect.
203. The kit of any one of clauses 190-202 wherein the buffer solution comprises about 0.03 mM to about 0.2 mM $MgCl_2$.
204. The kit of any one of clauses 190-203 wherein the buffer solution comprises about 0.002 mM to about 0.2 mM $MgCl_2$.
205. The kit of any one of clauses 190-204 wherein the buffer solution comprises less than about 0.02 mM $MgCl_2$.
206. The kit of any one of clauses 190-205 wherein the buffer solution does not comprise $MgCl_2$.
207. The kit of any one of clauses 190-206 wherein the buffer solution further comprises about 0.003 M to about 0.03 M $KH_2PO_4$.
208. The kit of any one of clauses 190-207 wherein the buffer solution further comprises about 0.01 M to about 0.1 M $Na_2HPO_4$.
209. The kit of any one of clauses 190-208 wherein the buffer solution further comprises about 0.001 M to about 0.04 M KCl.
210. The kit of any one of clauses 190-209 wherein buffer solution further comprises about 0.2 M to about 3.0 M NaCl.
211. The kit of any one of clauses 190-210 wherein the buffer solution further comprises about 0.02 N to about 0.2 N NaOH.
212. The kit of any one of clauses 190-211 wherein the buffer solution further comprises about 0.2 weight percent to about 5 weight percent of glucose.
213. The kit of any one of clauses 190-212 wherein the buffer solution comprises about 0.5 weight percent glucose or less.
214. The kit of any one of clauses 190-213 wherein the buffer solution does not comprise glucose
215. The kit of any one of clauses 190-214 wherein a concentration of collagen in the in-situ polymerizable collagen composition is about 0.1 mg/ml to about 40 mg/ml.
216. The kit of any one of clauses 190-215 wherein a concentration of collagen in the in-situ polymerizable collagen composition is about 7 mg/mL to about 8 mg/mL.
217. The kit of any one of clauses 190-216 wherein a concentration of collagen in a neutralized collagen filler, the neutralized collagen filler comprising the in-situ polymerizable collagen composition and the buffer solution, is about 6.3 to about 7.2 mg/mL.
218. The kit of any one of clauses 190-217 wherein the collagen solution comprises about 0.005 N hydrochloric acid to about 0.1 N hydrochloric acid.
219. The kit of any one of clauses 190-218 wherein the buffer solution is configured to polymerize the in-situ polymerizable collagen composition in a single mixing step comprising mixing the in-situ polymerizable collagen composition with the buffer solution.
220. The kit of any one of clauses 190-219 wherein the, in-situ polymerizable collagen composition and the buffer solution are in separate containers.
221. The kit of any one of clauses 190-220 wherein the separate containers comprise sterilized vials.
222. The kit of any one of clauses 190-221 wherein the separate containers comprise separate compartments of a dual-barrel syringe.
223. The kit of any one of clauses 190-222 wherein the dual-barrel syringe comprises a mixing element.
224. The kit of any one of clauses 190-223 wherein the dual-barrel syringe is sterilized.
225. The kit of any one of clauses 190-224 further comprising instructions for use of components of the kit.
226. The kit of any one of clauses 190-225 further comprising at least one therapeutic agent configured for local delivery to the tissue void or defect.
227. The kit of any one of clauses 190-226 wherein the at least one therapeutic agent comprises a chemotherapeutic agent, an anti-inflammatory agent, an antibiotic agent, an analgesic agent, or a combination thereof.
228. The kit of any one of clauses 190-227 wherein the tissue void or defect comprises a wound.
229. The kit of any one of clauses 190-228 wherein the tissue void or defect comprises a surgical wound.
230. The kit of any one of clauses 190-229 wherein the tissue void or defect resulted from removal of a tumor.
231. The kit of any one of clauses 190-230 wherein the tissue void or defect resulted from removal of a breast tumor.

232. The kit of any one of clauses 190-231 wherein the kit is for regenerating tissue following breast conserving surgery.

233. The kit of any one of clauses 190-232 wherein the kit is for preparing a matrix in a tissue void or defect.

234. The kit of any one of clauses 190-233 wherein the in-situ polymerizable collagen composition or the lyophilized oligomeric collagen is sterilized using ultraviolet radiation.

235. The kit of any one of clauses 190-234 wherein a collagen matrix that results from polymerization of the in-situ polymerizable collagen composition maintains a polymerization property relative to a collagen composition this is not irradiated or to lyophilized collagen that is not irradiated, respectively.

236. The kit of any one of clauses 190-233 wherein the polymerization proper is shear storage modulus.

237. The kit of any one of clauses 190-236 wherein a dose of the radiation ranges from about 5 mJ/cm$^2$ to about 800 mJ/cm$^2$.

238. The kit of any one of clauses 190-237 wherein a dose of the radiation dose ranges from about 30 mJ/cm$^2$ to about 300 mJ/cm$^2$.

239. The kit of any one of clauses 190-238 wherein sterilization inactivates viruses.

240. The kit of any one of clauses 190-239 wherein the in-situ polymerizable collagen composition or the lyophilized oligomeric collagen is sterilized using UVC irradiation.

241. The kit of any one of clauses 190-240 wherein the collagen composition or the lyophilized oligomeric collagen is sterilized using UVC irradiation and sterile filtration.

BRIEF DESCRIPTION OF THE DRAWINGS

FIGS. 1A-1D show an overview of liquid tissue filler that forms a viscoelastic matrix in-situ with soft tissue-like properties. FIG. 1A shows a kit that includes a syringe containing sterile type I oligomeric collagen solution, a syringe of propriety neutralization (self-assembly) buffer, a luer-lock adapter, and applicator tip. FIG. 1B shows the mixing of the two reagents followed by injection into a plastic mold maintained at body temperature (37° C.), wherein the liquid transitions into a stable, shape-retaining fibrillar collagen matrix. FIG. 1C shows a 4-20% and 6% SDS-PAGE gel documenting purity and characteristic banding pattern of type I oligomeric collagen in which Lane 1 corresponds to molecular weight standard and Lane 2 corresponds to type I oligomeric collagen. FIG. 1D shows a Table summarizing the tissue filler polymerization kinetics and performance specifications (mean±SD; N=4, n=6-8) of the matrix formed by the tissue filler.

FIGS. 2A-2G show an overview of a simulated lumpectomy procedure. FIG. 2A shows a Table summarizing surgically excised mammary tissue volume representing roughly one-fourth total breast tissue volume [Data (mean±SD) compiled from both longitudinal and radiation studies (1 week: collagen filler: n=12, no fill=6; 4 weeks: collagen filler: n=18, no fill: n=9; 16 weeks: collagen filler: n=18, no fill: n=9)]. FIG. 2B shows the surgical void before application of tissue filler. FIG. 2C shows the surgical void after application of the tissue filler. FIG. 2D shows application of the tissue filler. FIG. 2E shows excised porcine mammary tissue. FIG. 2F shows surgical sites immediately following surgery including bandaging. FIG. 2G shows surgical sites 16 weeks following simulated lumpectomy with irradiation.

FIG. 3A shows a graph of breast uniformity/consistency scores (mean±SD; collagen tissue filler: n=12; no fill: n=6) assigned by breast surgeon for collagen tissue filler and no fill (negative control) treated voids at various time points following simulated lumpectomy. All no surgery breasts scored 0. FIG. 3B shows cross-sections of surgical voids following treatment with collagen tissue filler or no fill compared to normal breast tissue. Arrows represent surgical clips placed to mark boundaries of surgical void.

FIG. 4A shows histologic cross-sections (H&E) of collagen filled voids at 1 week, 4 weeks, and 16 weeks following simulated lumpectomy. Low magnification images show the tissue filler within the voids and its interface with the surrounding host tissue (large arrows indicate surgical clip sites). High magnification images feature the central region of the tissue filler and the tissue filler-host tissue interface. Cellular infiltration, vascularization, and breast tissue formation within the matrix implant occur over time with no evidence of an inflammatory response (i.e., infiltration of neutrophils and macrophages) typically seen with healing of an untreated tissue void or foreign body reaction (i.e., activation of macrophages, formation of giant cells, phagocytosis, and fibrous capsule formation) typically observed with tissue-implant responses. By 16 weeks, the tissue filler is completely cellularized and vascularized (small arrows indicated blood vessels) with evidence of mammary gland (RG) and adipose tissue (RF) formation. One: Tissue filler matrix with no cell infiltration; Oc: Tissue filler matrix with cellular infiltrate. FIG. 4B shows cross-sections (H&E) of untreated (no fill) surgical voids at 1 week, 4 weeks, and 16 weeks following simulated lumpectomy. Low magnification images show voids and the surrounding host tissue. High magnification images feature the central region of the voids and the void/host tissue interface. Hematomas (H) were commonplace at 1 week, followed by progressive defect contraction and a healing response that results in scar tissue formation (S).

FIGS. 5A-5B show an overview of how tissue filler does not interfere with radiography or ultrasonography procedures. FIG. 5A shows representative ultrasound images and FIG. 5B shows representative radiographs of surgical voids treated with collagen tissue filler or no fill compared to normal breast tissue at 1-week, 4-week, and 16-week time points. Radiopaque marker clips evident within radiographs indicate boundaries of surgical void and show evidence of decreased wound contraction for voids treated with tissue filler compared to no fill voids.

FIG. 6A shows a graph of breast uniformity/consistency scores (mean±SD; collagen: n=6; no fill: n=3) assigned by breast surgeon for collagen tissue filler and no fill (negative control) treated voids at various time points following simulated lumpectomy and radiation. All no surgery breasts scored 0. FIG. 6B shows cross-sections of surgical voids following treatment with tissue filler or no fill and radiation compared to no surgery normal breast tissue.

Arrows represent surgical clips placed to mark boundaries of surgical void. FIG. 6C shows histologic cross-sections (H&E) of collagen filled voids at 4 weeks and 16 weeks following simulated lumpectomy with adjunct radiation. Low magnification images show the tissue filler within the voids and its interface with the surrounding host tissue. High magnification images feature the central region of the tissue filler and the tissue filler-host tissue interface. Cellular infiltration, vascularization, and breast tissue formation within the matrix implant occur over time, albeit at a slower rate than sites from non-irradiated animals. By 16 weeks, the tissue filler is completely cellularized and vascularized (small arrows indicated blood vessels) with evidence of adipose tissue (RF) formation. One: Tissue filler matrix with no cell infiltration; Oc: Tissue filler matrix with cellular infiltrate. FIG. 6D shows cross-sections (H&E) of untreated (no fill) surgical voids at 4 weeks and 16 weeks following simulated lumpectomy with radiation. Low magnification images show voids and the surrounding host tissue, with scar tissue (S) and a suture-related granuloma (G) evident at 4 weeks (large arrow indicates surgical clip site). High magnification images feature the central region of the inflammatory reaction and scar tissue formed within the void, the scar-host tissue interface.

FIG. 7A shows representative ultrasound images and FIG. 7B shows representative radiographs of surgical voids treated with the tissue filler or no fill and irradiation compared to normal breasts at 4-week and 16-week time points. Radiopaque marker clips evident within radiographs indicate boundaries of surgical void and show decreased wound contraction for voids treated with tissue filler compared to no fill voids.

FIGS. 8A-8B show timelines and processes of healing responses observed in porcine simulated lumpectomy model. FIG. 8A show schematics comparing and contrasting the phases and processes associated with the typical reparative healing response observed with no fill. FIG. 8B show schematics comparing and contrasting the phases and processes associated with the restorative and regenerative healing response observed with the collagen tissue filler.

FIG. 10 shows the semi-quantitative scoring used for post-surgical assessment of pig breasts. Breasts and surgical sites were assessed based on gross appearance, including evidence of erythema and eschar as well as edema. Palpation was used to assess breast uniformity and consistency.

FIGS. 11A-11D show an overview of how collagen tissue filler supports mammary gland formation, while glandular necrosis is evident in no fill treated voids. Corresponding H&E (FIGS. 11A and 11C) and pan cytokeratin stained (FIGS. 11B and 11D) cross-sections are shown of surgical voids 16 weeks following treatment with the collagen tissue filler (FIGS. 11A and 11B) or no fill (FIGS. 11/C and 11D) with selected regions representing the periphery of the collagen tissue filler and formed scar tissue, respectively. Pan cytokeratin highlights epithelial cells lining mammary lobules and ducts within collagen tissue filler and no fill groups. No fill group also shows evidence of necrotic glands (black and white arrows). Immunofluorescence images shows pan cytokeratin (green), with nuclei counterstained with DAPI (blue).

DETAILED DESCRIPTION

Figures 3A, 3B:
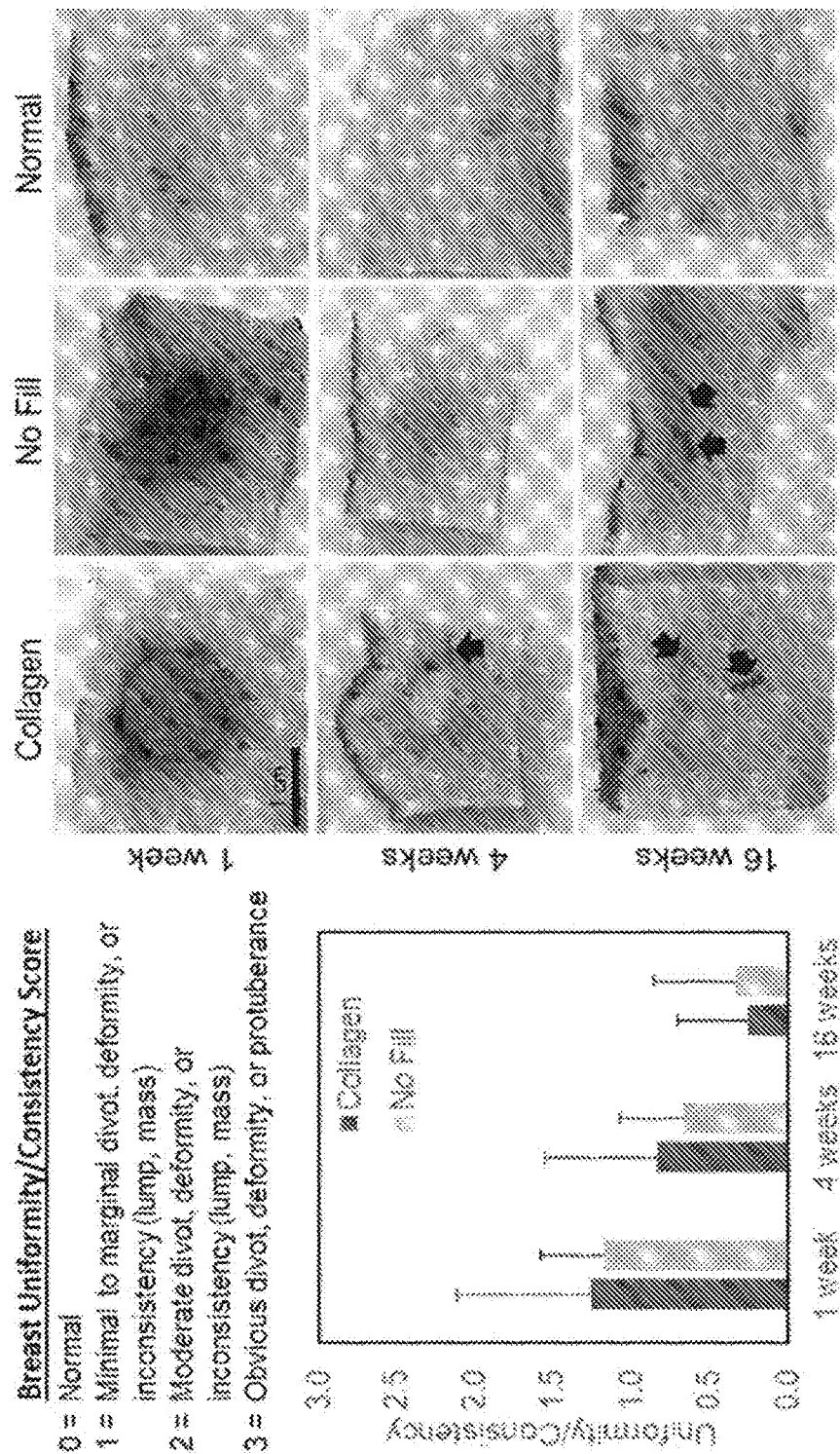
FIGS. 3A-3B show an overview of how tissue filler persists and induces a tissue-implant response that supports breast tissue formation without evoking a typical inflammatory response or foreign body reaction.

In accordance with the present teachings, a restorative and regenerative tissue filler is described that may be applied as a liquid to any type of tissue void or defect-including but not limited to tissue voids resulting from surgical wounds (e.g., including but not limited to surgical wounds stemming from BCS), physical defects (e.g., scars, divots, congenital defects, etc.), injuries, disease progressions, and/or the like-prior to transitioning to a fibrillar collagen matrix with tissue consistency. Using a porcine simulated BCS model, the collagen filler in accordance with the present teachings has been shown to induce a regenerative healing response characterized by rapid cellularization, vascularization, and progressive breast tissue neogenesis, including adipose tissue and mammary glands and ducts. In contrast to conventional biomaterials, no foreign body response or inflammatory-mediated "active" biodegradation were observed for a collagen filler in accordance with the present teachings. Moreover, the collagen filler in accordance with the present teachings also did not compromise simulated surgical re-excision, radiography, or ultrasonography procedures-features that are important for clinical translation. Furthermore, upon application of post-surgical radiation, the tissue response for a collagen filler in accordance with the present teachings was largely similar to that under non-irradiated conditions (although, as expected, healing was modestly slower). The in situ matrix-forming collagen in accordance with the present teachings is easy to apply, conforms to patient-specific defects, and generates complex tissues in the absence of inflammation. As such, the collagen filler in accordance with the present teachings has significant translational potential as the first regenerative tissue filler for BCS as well as other soft tissue restoration and reconstruction needs.

In some embodiments, a regenerative tissue filler in accordance with the present teachings may provide one or more of the following advantages: (1) reduced (i.e., relative to conventional no-fill procedures) or no scar tissue formation; (2) reduced (i.e., relative to conventional no-fill procedures) or no defect contraction; (3) reduced (i.e., relative to conventional no-fill procedures) or no inflammatory mediators or inflammatory response; (4) tissue consistency that is similar to that of natural tissue (e.g., a compressive modulus or range of compressive moduli that is similar to that of natural tissue); (5) restoration and generation of breast tissue with adipose tissue, mammary gland tissue, etc.; (6) restoration and generation of skeletal muscle; (7) tissue-implant response that does not interfere with routine clinical procedures including re-excision, ultrasonography, or radiography; and/or (8) tissue-implant response that is less (i.e., relative to conventional procedures) or not negatively impacted by adjunct radiation (e.g., no lipid cysts, microcalcifications, focal masses, and/or areas of increased opacity, any of which may interfere with imaging).

In accordance with the present teachings, the present inventors have sought a tissue filler that would (i) predictably restore and regenerate damaged tissue and tissue voids, (ii) be easily applied, (iii) conform to patient-specific defects varying broadly in size and geometry, and (iv) not interfere or compromise routine clinical processes and procedures. In some embodiments, the tissue filler is introduced into a tissue void or defect under aseptic conditions. In some embodiments, introduction of the tissue filler to the tissue void or defect may be achieved via injection (e.g., using one or a plurality of single-barrel syringes, a dual-barrel syringe, and/or the like, and combinations thereof). In other embodiments, the tissue filler may initially be applied to an external mold (e.g., in a surgical setting) to form a molded part, which may then be removed from the mold and implanted into a patient. Regenerative medicine approaches, including tunable, in situ forming biomaterials, have the potential to address many of these design considerations. In particular, type I oligomeric collagen (oligomer), a highly-purified molecular form of collagen that is readily soluble in dilute acid, represents a tunable, in situ forming biomaterial with potential to address many of these design considerations. Unlike conventional monomeric collagen preparations, namely telocollagen and atelocollagen, oligomer represents small aggregates of full-length triple-helical collagen molecules (i.e., tropocollagen) with carboxy- and amino-terminal telopeptide intact, held together by a naturally-occurring intermolecular crosslink. The preservation of these key molecular features, including carboxy- and amino-terminal telopeptide regions and associated intermolecular crosslinks, provides this natural polymer and the collagen materials it forms with desirable but uncommon properties. More specifically, oligomer retains its fibril-forming (self-assembly) capacity, which is inherent to fibrillar collagen proteins. Upon neutralization of oligomer to physiologic conditions (e.g., pH and ionic strength), this liquid form may be readily injected to completely fill complex contours and geometries. At body temperature, the liquid rapidly transitions to a fibrillar collagen matrix, recreating structural and biological signaling features of collagen matrices found in the extracellular matrix (ECM) component of tissues. Upon in vivo implantation, these matrices persist, showing slow metabolic turnover and remodeling, resistance to proteolytic degradation, and no active biodegradation or foreign body response. This natural polymer supports creation of materials with broadly tunable physical properties, including geometry, architecture (random or aligned fibrils, continuous fibril density gradients), and mechanical integrity, making it an enabling platform for personalized regenerative medicine. In situ forming collagen matrix shows promise as a regenerative tissue filler for breast conserving surgery and other soft tissue restoration needs.

In some embodiments, a regenerative tissue filler is provided, which may be applied as a liquid to wounds-including but not limited to defects or contours during BCS-prior to transitioning to a fibrillar collagen matrix with tissue consistency. Using a porcine-simulated BCS model, as further described below, the collagen filler was shown to induce a regenerative healing response, characterized by rapid cellularization, vascularization, and progressive breast tissue neogenesis, including adipose tissue and mammary glands and ducts. Unlike conventional biomaterials, no foreign body response or inflammatory-mediated "active" biodegradation was observed. The collagen filler also did not compromise simulated surgical re-excision, radiography, or ultrasonography procedures-features that are important for clinical translation. When post-BCS radiation was applied, the collagen fill and its associated tissue response were largely similar to non-irradiated conditions. However, as expected, the healing rate was modestly slower. This in site matrix-forming collagen is easy to apply, conforms to patient-specific defects/contours, and regenerates complex tissues in the absence of inflammation. It has significant translational potential as the first regenerative tissue filler for BCS as well as other soft tissue and skeletal muscle tissue restoration and reconstruction needs.

The collagen filler described herein is fundamentally different from conventional flowable and injectable collagen products that are or have previously been used for soft tissue augmentation (e.g., cosmetic procedures), management of skin wounds (e.g., ulcers), and tissue hulking (e.g., urinary incontinence). Such products, which include Zyderm®, Zyplast®, Integra Flowable®, and Contigen®, are fashioned from reconstituted, enzymatically-treated collagen (atelocollagen) or granulated tissue particulate derived from bovine, porcine, or human tissue sources. To make these materials injectable, the insoluble fibrous collagen or tissue particulate is suspended in physiologic saline solutions to create dispersions or suspensions. All of these implantable collagens are temporary and exhibit rapid biodegradation (reabsorption; 1-6 months), where they are actively degraded via inflammatory-mediated processes, including phagocytosis by macrophages/giant cells and proteolytic degradation by secreted matrix metalloproteinases. To slow degradation and improve persistence, many of these products are treated with glutaraldehyde or other exogenous crosslinking processes.

By contrast, oligomeric collagen represents a molecular subdomain found within natural tissue collagen fibers (e.g., porcine dermis), which may be extracted and purified so that it is free from cellular and other immunogenic tissue components. The type I collagen protein and crosslink chemistry comprising this subdomain are highly conserved across species, documenting significance of this major structural element within the body. Physiologic conditions induce fibril formation, where oligomer molecules assemble into staggered arrays, giving rise to interconnected networks or matrices of fibrils. Published studies show that formed matrices are largely similar to those found naturally within the extracellular matrix, comprising fibrils with regular D-banding patterns that readily engage in biosignaling. The natural crosslink chemistry present in oligomer, but not found in polymerizable monomeric collagens, is the primary contributor to the rapid matrix-forming reaction as well as the improved mechanical integrity, slow metabolic turnover, and resistance to proteolytic degradation exhibited by oligomer matrices. Collectively, these distinguishing features contribute to the uncommon mechanism of action and regenerative tissue response displayed by oligomer matrices when compared to conventional biodegradable collagen materials.

The ability to restore and regenerate tissue that is diseased, damaged, or dysfunctional has been one of the greatest challenges in medicine. In fact, researchers have been working to identify biomaterials and/or anti-inflammatory agents with the goal of achieving a more desirable healing outcome (i.e., regeneration) or biomaterial/device implant response. For the breast, this challenge is particularly difficult, since it is comprised of multiple tissue types with distinct functions, including secretory (i.e., milk-producing) glands and ducts, supportive collagenous connective tissue, and volume-filling adipose tissue. At present, tissue engineering and regenerative medicine strategies for soft tissue and breast reconstruction remain in their infancy, with only a few strategies evaluated in large animal models to date. The majority of approaches have focused on engineering adipose tissue from biologic or synthetic scaffolds, incorporating lipofilling, patient-derived cell populations, and growth factors to encourage adipogenesis and vascularization. A major drawback to conventional synthetic scaffold approaches is the inability of the materials to signal cells, resulting in foreign body responses and slow cellularization and vascularization.

In some embodiments, the tissue filler may comprise a purified, fibril-forming liquid type I collagen, such as one derived from porcine dermis. In some embodiments, this in-situ forming collagen device may be supplied as a single use kit containing: a sterile glass vial containing the collagen solution (10 mL) in dilute (0.01 N) hydrochloric acid, a sterile glass vial containing the proprietary neutralization (self-assembly) reagent (2 mL), two sterile 10-ml syringes, a sterile luer-lock connector, and a sterile applicator tip. After drawing up 9 mL of liquid collagen in one syringe and 1 mL of neutralization buffer in the other, the user connects the two syringes with a luer-lock connector and mixes the two reagents. After mixing, the neutralized collagen solution may be injected to fill tissue voids or defects, including those that are deep and difficult to access, and irregularly shaped. Upon application, it undergoes rapid (~1 minute at body temperature) fibril formation via molecular self-assembly. The resulting tissue filler matrix restores and maintains tissue shape and soft tissue consistency over time and elicits a tissue-implant response characterized by cellularization, vascularization, and new tissue formation without evoking an inflammatory response that is typically observed with wound healing or a foreign body reaction that is typically observed with conventional tissue-implant responses.

The liquid format of the specially formulated collagen readily fills and conforms to patient-specific defect geometries and contours and is amenable to minimally invasive procedures. Once applied to the site, the collagen solution undergoes a polymerization (molecular self-assembly reaction) to form a physically stable fibrillar collagen matrix that persists and maintains its volume. The matrix provides critical biochemical and biomechanical signaling to cells, supporting cellularization, vascularization, and tissue formation that is site-appropriate, in absence of an inflammatory response or foreign body reaction. This includes complex tissue compositions with distinct functions such as those found in the breast. The material is compatible with a number of standard clinical procedures, including irradiation, radiography, ultrasonography, and surgical re-excision.

Throughout this description and in the appended claims, the following definitions are to be understood:

The phrase "oligomeric collagen" refers to collagen that comprises cross-linked collagen molecules. Collagen molecules are composed of three separate polypeptide chains, which collectively give rise to its triple helical quaternary structure which is flanked by non-helical telopeptide ends. As used herein, the phrase "oligomeric collagen" is to be understood as referring to collagen molecules at least a portion of which are held together covalently through intermolecular cross-linking. Oligomeric collagen may be polymerized, for example, as described herein. Polymerizable oligomeric collagen is oligomeric collagen capable of being polymerized. One example of a cross-linked collagen molecule that may be found in oligomeric collagen is tropocollagen.

The term "sterilized" refers to the removal of contaminants including, but not limited to, infectious agents. For example, contaminants (e.g., bacteria, viruses) may be removed by inactivation, reduction in number or amount, or by inhibition of activity of contaminating agents, whether infectious or not.

The term "purified" refers to removal of contaminants including, but not limited to, cellular contaminants, nucleotide contaminants, and endotoxins.

The phrase "foreign body reaction" refers to a localized inflammatory response elicited by any material that would not normally be found within the body. This reaction may be characterized by protein adsorption and an inflammatory process marked by macrophage activation, giant cell formation and fibrous capsule formation and/or degradation or phagocytosis of foreign materials.

The phrase "tissue implant response" refers to a subset of a "foreign body reaction," which results specifically from the implantation of a material into a patient's body.

The term "patient" refers to any animal to be treated for a tissue void or defect, including but not limited to vertebrate animals. As used herein, the term "patient" includes but is not limited to mammals, reptiles, amphibians, birds, and fish. In some embodiments, the patient refers to a mammal (e.g., a human, dog, cat, horse, rabbit, pig, etc.). In illustrative embodiments, the patient is a human being.

The terms "void" and "defect" refer to all manner of tissue anomalies including but not limited to wounds, surgical wounds including but not limited to surgical wounds stemming from BCS), physical defects (e.g., scars, divots, congenital defects, etc.), injuries, disease progressions (muscle atrophy, etc.), and/or the like, and combinations thereof. As used herein, the term "tissue" includes both hard tissue (e.g., skeletal bone) and soft tissue. As such, the phrase "tissue anomalies" encompasses all manner of anomalies in both hard and soft tissue.

The terms "restore" and "regenerate" as used in reference to tissue refer, respectively, to the reestablishment of a tissue presence in an area of a patient that previously had been characterized by a tissue void or defect and to the regrowth of tissue in this same area. In some embodiments, the restored and/or regenerated tissue may reflect one or more of the appearance, structure, and function of the original tissue that is being replaced.

The term "contraction" as used in reference to tissue refers to a type of scarring that is characterized by a reduction in tissue area and which typically results from a healing response in a body.

The term "matrix" refers to a collagen-fibril scaffold-like structure configured to provide a platform on, around, and within which tissue may originate, develop, and/or grow.

In some embodiments, a method for filling a tissue void or defect in accordance with the present teachings includes (a) introducing into the tissue defect or void a self-assembling biopolymer, and (b) polymerizing the self-assembling biopolymer to form a shape-retaining matrix.

In some embodiments, a method for filling a tissue void or defect generated by a lumpectomy or mastectomy procedure in accordance with the present teachings includes (a) introducing into the surgical wound site a mixture containing an oligomeric collagen solution and a neutralization solution; and (b) polymerizing the oligomeric collagen solution to form a collagen-fibril matrix. The oligomeric collagen solution may include a lyophilized type I oligomeric collagen and an acid.

In some embodiments, a method for filling a tissue void or defect generated by a lumpectomy or mastectomy procedure includes (a) introducing into the surgical wound site a mixture containing an oligomeric collagen solution and a neutralization solution; and (b) polymerizing the oligomeric collagen solution to form a collagen-fibril matrix. In some embodiments, the oligomeric collagen solution may include a lyophilized type I oligomeric collagen and 0.01 N hydrochloric acid. In some embodiments, a concentration of the oligomeric collagen solution is about 8 mg/mL based on a dry weight of the lyophilized type I oligomeric collagen. In some embodiments, a ratio of the oligomeric collagen solution to the neutralization solution is about 9:1.

In other embodiments, a collagen matrix prepared according to any of the above-described methods is provided. In further embodiments, a kit containing a collagen composition and a buffer solution is provided. In further embodiments, a kit containing lyophilized type I oligomeric collagen, a hydrochloric acid solution, and a buffer solution is provided.

Several additional embodiments are described by the following enumerated clauses. Any applicable combination of these embodiments is also contemplated, and any applicable combination of these embodiments with the embodiments described in this DETAILED DESCRIPTION section of the application is also contemplated.

1. A method for filling a tissue void or defect in a patient, the method comprising: introducing into the tissue void or defect a self-assembling biopolymer; and polymerizing the self-assembling biopolymer to form a shape-retaining matrix.
2. The method of clause 1 wherein the self-assembling biopolymer comprises in situ polymerizable oligomeric collagen.
3. The method of any preceding clause wherein the in-situ polymerizable oligomeric collagen comprises collagen molecules.
4. The method of any preceding clause wherein at least a portion of the collagen molecules are covalently bonded by one or a plurality of intermolecular cross-links.
5. The method of any preceding clause wherein the patient is a mammal.
6. The method of any preceding clause wherein the patient is a human.
7. The method of any preceding clause wherein the introducing is achieved under aseptic conditions.
8. The method of any preceding clause wherein the self-assembling biopolymer comprises in-situ polymerizable collagen, and wherein the shape-retaining matrix comprises a collagen-fibril matrix.
9. The method of any preceding clause wherein the self-assembling biopolymer comprises a liquid type I collagen.
10. The method of any preceding clause wherein the self-assembling biopolymer comprises a type I oligomeric collagen derived from porcine dermis.
11. The method of any preceding clause wherein the self-assembling biopolymer comprises a solution comprising a lyophilized type I oligomeric collagen and an acid.
12. The method of any preceding clause wherein the self-assembling biopolymer comprises a solution comprising a lyophilized type I oligomeric collagen and hydrochloric acid.
13. The method of any preceding clause wherein the self-assembling biopolymer comprises a solution comprising a lyophilized type I oligomeric collagen and hydrochloric acid, and wherein the solution further comprises a buffer solution.
14. The method of any preceding clause wherein the self-assembling biopolymer comprises an oligomeric collagen solution and a buffer solution, wherein the oligomeric collagen solution comprises a lyophilized type I oligomeric collagen and an acid.
15. The method of any preceding clause wherein the self-assembling biopolymer comprises an oligomeric collagen solution and a buffer solution, wherein the oligomeric collagen solution comprises a lyophilized type I oligomeric collagen and an acid, and wherein a ratio of the oligomeric collagen solution to the buffer solution is about 9:1.
16. The method of any preceding clause wherein the self-assembling biopolymer comprises a solution comprising a lyophilized type I oligomeric collagen and 0.01 N hydrochloric acid, wherein a concentration of the solution is about 8 mg/mL based on a dry weight of the lyophilized type I oligomeric collagen.
17. The method of any preceding clause wherein the self-assembling biopolymer comprises a solution comprising a lyophilized type I oligomeric collagen and hydrochloric acid, wherein the solution has been clarified using ultracentrifugation.
18. The method of any preceding clause wherein the self-assembling biopolymer comprises a solution comprising a lyophilized type I oligomeric collagen and hydrochloric acid, wherein the solution has been clarified using ultracentrifugation and then filtered through a sterile membrane filter.
19. The method of any preceding clause wherein the self-assembling biopolymer comprises a solution comprising a lyophilized type I oligomeric collagen and hydrochloric acid, wherein the solution has been clarified using ultracentrifugation, dosed with ultraviolet radiation, and then filtered through a sterile membrane filter.
20. The method of any preceding clause wherein the self-assembling biopolymer comprises a solution comprising a lyophilized type I oligomeric collagen and hydrochloric acid, wherein the solution has been clarified using ultracentrifugation, dosed with 500 mJ/cm$^2$ ultraviolet radiation, and then filtered through a sterile membrane filter.
21. The method of any preceding clause wherein the introducing comprising injecting the self-assembling biopolymer into the tissue void or defect via a syringe.
22. The method of any preceding clause wherein the tissue void or defect is generated by a lumpectomy procedure.
23. The method of any preceding clause wherein tissue void or defect is generated by a mastectomy procedure.
24. The method of any preceding clause wherein the filling of the tissue void or defect does not result in defect contraction or scar tissue formation.

25. The method of any preceding clause wherein the filling of the tissue void or defect does not result in an inflammatory mediator, an inflammatory response, or a foreign body reaction.

26. The method of any preceding clause wherein the filling of the tissue void or defect results in a compressive modulus or range of compressive moduli substantially identical to that of natural tissue.

27. The method of any preceding clause wherein the filling of the tissue void or defect results in generation of breast tissue with adipose tissue, mammary gland tissue, or a combination thereof.

28. The method of any preceding clause wherein a tissue-implant response to the filling of the tissue void or defect is not negatively impacted by radiation, such that one or more of lipid cysts, microcalcifications, focal masses, and/or areas of increased opacity are not observed.

29. A method for filling a tissue void or defect in a patient, the tissue void or defect generated by a lumpectomy or mastectomy procedure, the method comprising: introducing into the tissue void or defect a mixture comprising an oligomeric collagen solution and a buffer solution; and polymerizing the oligomeric collagen solution to form a collagen-fibril matrix; wherein the oligomeric collagen solution comprises a lyophilized type I oligomeric collagen and an acid.

30. The method of clause 29 wherein a ratio of the oligomeric collagen solution to the buffer solution about 9:1.

31. The method of clause 29 or clause 30 wherein the acid comprises 0.01 N hydrochloric acid and wherein a concentration of the oligomeric collagen solution is about 8 mg/mL based on a dry weight of the lyophilized type I oligomeric collagen.

32. A method for filling a tissue void or defect in a patient, the tissue void or defect generated by a lumpectomy or mastectomy procedure, the method comprising: introducing into the tissue void or defect a mixture comprising an oligomeric collagen solution and a buffer solution; and polymerizing the oligomeric collagen solution to form a collagen-fibril matrix; wherein the oligomeric collagen solution comprises a lyophilized type I oligomeric collagen and 0.01 N hydrochloric acid; wherein a concentration of the oligomeric collagen solution is about 8 mg/mL based on a dry weight of the lyophilized type I oligomeric collagen; and wherein a ratio of the oligomeric collagen solution to the buffer solution is about 9:1.

33. The method of clause 32 wherein the oligomeric collagen solution has been clarified using ultracentrifugation, filtered through a sterile membrane filter, dosed with ultraviolet radiation, or a combination thereof.

34. The method of any one of clauses 32-33 wherein the tissue void or defect comprises a wound.

35. The method of any one of clauses 32-34 wherein the tissue void or defect comprises a surgical wound.

36. The method of any one of clauses 32-35 wherein the tissue void or defect resulted from removal of a tumor.

37. The method of any one of clauses 32-36 wherein the tissue void or defect resulted from removal of a breast tumor.

38. The method of any one of clauses 32-37 wherein the self-assembling biopolymer comprises a tissue filler.

39. The method of any one of clauses 32-38 wherein the filling of the tissue void or defect does not result in defect contraction or scar tissue formation.

40. The method of any one of clauses 32-39 wherein the filling of the tissue void or defect does not result in an inflammatory mediator, an inflammatory response, or a foreign body reaction.

41. The method of any one of clauses 32-40 wherein the filling of the tissue void or defect results in a compressive modulus or range of compressive moduli substantially identical to that of natural tissue.

42. The method of any one of clauses 32-41 wherein the filling of the tissue void or defect results in generation of breast tissue with adipose tissue, mammary gland tissue, or a combination thereof.

43. The method of any one of clauses 32-42 wherein a tissue-implant response to the filling of the tissue void or defect is not negatively impacted by radiation, such that one or more of lipid cysts, microcalcifications, focal masses, and/or areas of increased opacity are not observed.

44. A method for filling a wound, the method comprising: introducing into the wound a mixture comprising an oligomeric collagen solution and a buffer solution; and polymerizing the oligomeric collagen solution to form a collagen-fibril matrix; wherein the oligomeric collagen solution comprises a lyophilized oligomeric collagen and an acid.

45. The method of clause 44 wherein the lyophilized type oligomeric collagen comprises lyophilized type I oligomeric collagen.

46. The method of clause 44 or clause 45 wherein the wound comprises a surgical wound.

47. The method of any one of clauses 44-46 wherein the surgical wound resulted from removal of a tumor.

48. The method of any one of clauses 44-47 wherein the surgical wound resulted from removal of a breast tumor.

49. The method of any one of clauses 44-48 wherein the oligomeric collagen solution comprises a tissue filler.

50. The method of any one of clauses 44-49 wherein the filling of the wound does not result in defect contraction and scar tissue formation.

51. The method of any one of clauses 44-50 wherein the filling of the wound does not result in an inflammatory mediator, an inflammatory response, or a foreign body reaction.

52. The method of any one of clauses 44-51 wherein the filling of the wound results in a compressive modulus or range of compressive moduli substantially identical to that of natural tissue.

53. The method of any one of clauses 44-52 wherein the filling of the wound results in generation of breast tissue with adipose tissue, mammary gland tissue, or a combination thereof.

54. The method of any one of clauses 44-53 wherein a tissue-implant response to the filling of the wound is not negatively impacted by radiation, such that one or more of lipid cysts, microcalcifications, focal masses, and/or areas of increased opacity are not observed.

55. A method for restoring and regenerating skeletal muscle tissue in a tissue void or defect of a patient, the method comprising: introducing into the tissue void or defect a self-assembling biopolymer; and polymerizing the self-assembling biopolymer to form a shape-retaining matrix.

56. The method of clause 55 wherein the tissue void or defect comprises a wound.

57. The method of clause 55 or clause 56 wherein the tissue void or defect comprises a surgical wound.

58. The method of any one of clauses 55-57 wherein the tissue void or defect resulted from removal of a tumor.
59. The method of any one of clauses 55-58 wherein the restoring and regenerating of the skeletal muscle tissue in the tissue void or defect does not result in defect contraction or scar tissue formation.
60. The method of any one of clauses 55-59 wherein the restoring and regenerating of the skeletal muscle tissue in the tissue void or defect does not result in an inflammatory mediator, an inflammatory response, or a foreign body reaction.
61. The method of any one of clauses 55-60 wherein the restoring and regenerating of the skeletal muscle tissue in the tissue void or defect results in a compressive modulus or range of compressive moduli substantially identical to that of natural tissue.
62. The method of any one of clauses 55-61 wherein the restoring and regenerating of the skeletal muscle tissue in the tissue void or defect results in generation of skeletal muscle with adipose tissue.
63. The method of any one of clauses 55-62 wherein a tissue-implant response to the restoring and regenerating of the skeletal muscle tissue is not negatively impacted by radiation, such that one or more of lipid cysts, microcalcifications, focal masses, and/or areas of increased opacity are, not observed.
64. A method for restoring and regenerating skeletal muscle tissue in a tissue void or defect, the method comprising: introducing into the tissue void or defect a mixture comprising an oligomeric collagen solution and a buffer solution; and polymerizing the oligomeric collagen solution to form a collagen-fibril matrix; wherein the oligomeric collagen solution comprises a lyophilized type I oligomeric collagen and an acid.
65. The method of clause 64 wherein the tissue void or defect comprises a wound.
66. The method of clause 64 or clause 65 wherein the tissue void or defect comprises a surgical wound.
67. The method of any one of clauses 64-66 wherein the tissue void or defect resulted from removal of a tumor.
68. The method of any one of clauses 64-67 wherein the restoring and regenerating of the skeletal muscle tissue in the tissue void or defect does not result in defect contraction or scar tissue formation.
69. The method of any one of clauses 64-68 wherein the restoring and regenerating of the skeletal muscle tissue in the tissue void or defect does not result in an inflammatory mediator, an inflammatory response, or a foreign body reaction.
70. The method of any one of clauses 64-69 wherein the restoring and regenerating of the skeletal muscle tissue in the tissue void or defect results in a compressive modulus or range of compressive moduli substantially identical to that of natural tissue.
71. The method of any one of clauses 64-70 wherein the restoring and regenerating of the skeletal muscle tissue in the tissue void or defect results in generation of skeletal muscle with adipose tissue.
72. The method of any one of clauses 64-71 wherein a tissue-implant response to the restoring and regenerating of the skeletal muscle tissue is not negatively impacted by radiation, such that one or more of lipid cysts, microcalcifications, focal masses, and/or areas of increased opacity are not observed.
73. A method for preparing a matrix in a tissue void or defect, the method comprising polymerizing collagen using a single mixing step, the single mixing step comprising mixing a collagen composition with a buffer solution to form a collagen solution, wherein the collagen in the collagen solution polymerizes to form the matrix.
74. The method of clause 73 further comprising incubating the collagen solution at a temperature of greater than about 25° C. to promote polymerization of the collagen in the collagen solution.
75. The method of clause 73 or clause 74 further comprising incubating the collagen solution at a temperature of about 37° C. to promote polymerization of the collagen in the collagen solution.
76. The method of any one of clauses 73-75 wherein the collagen comprises collagen oligomers.
77. The method of any one of clauses 73-76 wherein the collagen comprises collagen molecules.
78. The method of any one of clauses 73-77 wherein the collagen consists of collagen oligomers.
79. The method of any one of clauses 73-78 wherein the collagen consists of intermolecularly cross-linked collagen molecules.
80. The method of any one of clauses 73-79 wherein the collagen consists essentially intermolecularly cross-linked collagen molecules.
81. The method of any one of clauses 73-80 wherein the collagen further comprises telocollagen.
82. The method of any one of clauses 73-81 wherein the collagen further comprises atelocollagen.
83. The method of any one of clauses 73-82 wherein the collagen comprising collagen oligomers is obtained from a tissue containing collagen oligomers, from cells producing collagen oligomers, or by chemically cross-linking collagen to obtain the collagen oligomers.
84. The method of any one of clauses 73-83 wherein the collagen is derived from porcine skin tissue.
85. The method of any one of clauses 73-84 wherein the collagen composition further comprises an acid.
86. The method of any one of clauses 73-85 wherein the acid is selected from the group consisting of hydrochloric acid, acetic acid, lactic acid, formic acid, citric acid, sulfuric acid, and phosphoric acid.
87. The method of any one of clauses 73-86 wherein the acid is hydrochloric acid.
88. The method of any one of clauses 73-87 wherein the hydrochloric acid is about 0.005 N to about 0.1 N hydrochloric acid.
89. The method of any one of clauses 73-88 wherein the hydrochloric acid is about 0.01 N hydrochloric acid.
90. The method of any one of clauses 73-89 wherein a concentration of the collagen in the collagen solution is about 0.1 mg/ml to about 40 mg/ml.
91. The method of any one of clauses 73-90 wherein a concentration of the collagen in the collagen solution is about 7 mg/ml to about 8 mg/mL.
92. The method of any one of clauses 73-91 wherein a concentration of the collagen in the mixture of the collagen solution and the buffer solution is about 6.3 to about 7.2 mg/mL.
93. The method of any one of clauses 73-92 wherein the collagen composition is sterilized.
94. The method of any one of clauses 73-93 wherein the collagen composition, the collagen solution, or the collagen matrix is sterilized by a method selected from the group consisting of exposure to chloroform, viral filtration, sterile filtration, gamma irradiation, ultraviolet radiation, E-beam, and combinations thereof.

95. The method of any one of clauses 73-94 wherein the collagen composition is sterilized by filtration.

96. The method of any one of clauses 73-95 wherein the buffer solution comprises about 0.03 mM to about 0.2 mM $MgCl_2$.

97. The method of any one of clauses 73-96 wherein the buffer solution comprises about 0.002 mM to about 0.02 mM $MgCl_2$.

98. The method of any one of clauses 73-97 wherein the buffer solution comprises less than about 0.02 mM $MgCl_2$.

99. The method of any one of clauses 73-98 wherein buffer solution does not comprise $MgCl_2$.

100. The method of any one of clauses 73-99 wherein e buffer solution further comprises about 0.3 mM to about 3 mM $KH_2PO_4$.

101. The method of any one of clauses 73-100 wherein the buffer solution further comprises about 1 mM to about 10 M $Na_2HPO_4$.

102. The method of any one of clauses 73-101 wherein the buffer solution further comprises about 0.1 mM to about 4 mM KCl.

103. The method of any one of clauses 73-102 wherein the buffer solution further comprises about 0.02 M to about 0.3 M NaCl.

104. The method of any one of clauses 73-103 wherein the buffer solution further comprises about 0.002 N to about 0.02 N NaOH.

105. The method of any one of clauses 73-104 wherein the buffer solution further comprises about 0.5 weight percent to about 5 weight percent of glucose.

106. The method of any one of clauses 73-105 wherein the buffer solution comprises about 0.5 weight percent glucose or less.

107. The method of any one of clauses 73-106 wherein the buffer solution does not comprise glucose.

108. The method of any one of clauses 73-107 further comprising adding cells to the collagen solution.

109. The method of any one of clauses 73-108 wherein the matrix comprises collagen fibrils.

110. The method of any one of clauses 73-109 wherein the collagen is soluble collagen.

111. The method of any one of clauses 73-110 wherein the collagen composition, the collagen solution, and/or the matrix is sterilized using UVC irradiation.

112. The method of any one of clauses 73-111 wherein the collagen composition, the collagen solution, and/or the matrix is sterilized using UVC irradiation and sterile filtration.

113. The method of any one of clauses 73-112 wherein the matrix that results from polymerization of the collagen solution maintains a polymerization property relative to a collagen composition this is not irradiated or to lyophilized collagen that is not irradiated, respectively.

114. The method of any one of clauses 73-113 wherein the polymerization property is shear storage modulus.

115. The method of any one of clauses 73-114 wherein a dose of the radiation ranges from about 5 $mJ/cm^2$ to about 800 $mJ/cm^2$.

116. The method of any one of clauses 73-115 wherein a dose of the radiation dose ranges from about 30 $mJ/cm^2$ to about 300 $mJ/cm^2$.

117. The method of any one of clauses 73-116 wherein sterilization s viruses.

118. A method for preparing a matrix in a tissue defect or void site, said method comprising polymerizing, collagen by mixing a collagen composition with a buffer solution to form a collagen solution, and polymerizing the collagen in the collagen solution to form the matrix wherein the buffer solution does not contain magnesium ions or manganese ions.

119. The method of clause 118 further comprising incubating the collagen solution at a temperature of greater than about 25° C. to promote polymerization of the collagen in the collagen solution.

120. The method of clause 118 or clause 119 further comprising incubating the collagen solution at a temperature of about 37° C. to promote polymerization of the collagen in the collagen solution.

121. The method of any one of clauses 118-120 wherein the collagen comprises collagen oligomers.

122. The method of any one of clauses 118-121 wherein the collagen comprises collagen molecules.

123. The method of any one of clauses 118-122 wherein the collagen consists of collagen oligomers.

124. The method of any one of clauses 118-123 wherein the collagen consists of intermolecularly cross-linked collagen molecules.

125. The method of any one of clauses 118-124 wherein the collagen consists essentially of intermolecularly cross-linked collagen molecules.

126. The method of any one of clauses 118-125 wherein the collagen further comprises telocollagen.

127. The method of any one of clauses 118-126 wherein the collagen further comprises atelocollagen.

128. The method any one of clauses 118-127 wherein the collagen comprising collagen oligomers is obtained from a tissue containing collagen oligomers, from cells producing collagen oligomers, or by chemically cross-linking collagen to obtain the collagen oligomers.

129. The method of any one of clauses 118-128 wherein the collagen is derived from porcine skin tissue.

130. The method any one of clauses 118-129 wherein the collagen composition further comprises an acid.

131. The method of any one of clauses 118-130 wherein the acid is selected from the group consisting of hydrochloric acid, acetic acid, lactic acid, formic acid, citric acid, sulfuric acid, and phosphoric acid.

132. The method of any one of clauses 118-131 wherein the acid is hydrochloric acid.

133. The method of any one of clauses 118-132 wherein the hydrochloric acid is about 0.005 N to about 0.1 N hydrochloric acid.

134. The method of any one of clauses 118-133 wherein the hydrochloric acid s about 0.01 N hydrochloric acid.

135. The method of any one of clauses 118-134 wherein a concentration of the collagen in the collagen solution is about 0.1 mg/ml to about 40 mg/ml.

136. The method of any one of clauses 118-135 wherein a concentration of the collagen in the collagen solution is about 7 mg/ml, to about 8 mg/mL.

137. The method of any one of clauses 118-136 wherein a concentration of the collagen in the mixture of the collagen solution and the buffer solution is about 6.3 to about 7.2 mg/mL.

138. The method of any one of clauses 118-137 wherein collagen corn position is sterilized.

139. The method of any one of clauses 118-138 wherein the collagen composition, the collagen solution, or the collagen matrix is sterilized by a method selected from the group consisting of exposure to chloroform, viral filtration, sterile filtration, gamma irradiation, ultraviolet radiation, E-beam, and combinations thereof.

140. The method of any one of clauses 118-139 wherein the collagen composition is sterilized by filtration.
141. The method of any one of clauses 118-140 Therein the buffer solution comprises about 0.03 mM to about 0.2 mM $MgCl_2$.
142. The method of 141 wherein the buffer solution comprises about 0.002 mM to about 0.02 mM $MgCl_2$.
143. The method of any one of clauses 118-142 wherein the buffer solution comprises less than about 0.02 mM $MgCl_2$.
144. The method of any one of clauses 118-143 wherein the buffer solution does not comprise $MgCl_2$.
145. The method of any one of clauses 118-144 wherein the buffer solution further comprises about 0.3 mM to about 3 mM $KH_2PO_4$.
146. The method of any one of clauses 118-145 wherein the buffer solution further comprises about 1 mM to about 10 M $Na_2HPQ_4$.
147. The method of any one of clauses 118-146 wherein the buffer solution further comprises about 0.1 mM to about 4 mM KCl.
148. The method of any one of clauses 8-147 wherein the buffer solution further comprises about 0.02 M to about 0.3 M NaCl.
149. The method of any one of clauses 118-148 wherein the buffer solution further comprises about 0.002 N to about 0.02 N NaOH.
150. The method of any one of clauses 118-149 wherein the buffer solution further comprises about 0.5 weight percent to about 5 weight percent of glucose.
151. The method of any one of clauses 118-150 wherein the buffer solution comprises about 0.5 weight percent glucose or less.
152. The method of any one of clauses 118-151 wherein the buffer solution does not comprise glucose.
153. The method of any one of clauses 118-152 further comprising adding cells to the collagen solution.
154. The method of any one of clauses 118-153 wherein the matrix comprises collagen fibrils.
155. The method of any one of clauses 118-154 wherein the collagen is soluble collagen.
156. The method of any one of clauses 118-155 wherein the collagen composition, the collagen solution, and/or the collagen matrix is sterilized using ultraviolet radiation.
157. The method of any one of clauses 118-156 wherein the collagen composition, the collagen solution, and/or the matrix is sterilized using UVC irradiation and sterile filtration.
158. The method of any one of clauses 118-157 wherein the matrix that results from polymerization of the collagen solution maintains a polymerization property relative to a collagen composition this is not irradiated or to lyophilized collagen that is not irradiated, respectively.
159. The method of any one of clauses 118-158 wherein the polymerization property is shear storage modulus.
160. The method of any one of clauses 118-159 wherein a dose of the radiation ranges from about 5 $mJ/cm^2$ to about 800 $mJ/cm^2$.
161. The method of any one of clauses 118-160 wherein a dose of the radiation dose ranges from about 30 $mJ/cm^2$ to about 300 $mJ/cm^2$.
162. The method of any one of clauses 118-161 wherein sterilization inactivates viruses.
163. A collagen matrix prepared according to the method of any one of clauses 1-162.
164. The collagen matrix of clause 163 wherein the collagen matrix medical graft.
165. The collagen matrix of clause 163 or clause 164 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.
166. The collagen matrix of any one of clauses 163-165 wherein the collagen matrix is used for research purposes.
167. The collagen matrix of any one of clauses 163-166 wherein the collagen matrix is used for drug toxicity testing or drug development.
168. The collagen matrix of any one of clauses 163-167 wherein the collagen matrix is sterilized using ultraviolet radiation.
169. The collagen matrix of any one of clauses 163-168 wherein the collagen matrix maintains a polymerization property relative to a collagen matrix that is not irradiated.
170. The collagen matrix of any one of clauses 163-169 wherein the polymerization property is shear storage modulus.
171. The collagen matrix of any one of clauses 163-170 wherein the radiation dose ranges from about 5 $mJ/cm^2$ to about 800 $mJ/cm^2$.
172. The collagen matrix of any one of clauses 163-171 wherein the radiation dose ranges from about 30 $mJ/cm^2$ to about 300 $mJ/cm^2$.
173. The collagen matrix of any one of clauses 163-172 wherein the sterilization inactivates viruses.
174. The collagen matrix of any one of clauses 163-173 wherein the collagen matrix is sterilized using UVC irradiation.
175. The collagen matrix of any one of clauses 163-174 wherein the collagen matrix is sterilized using UVC irradiation and sterile filtration.
176. A collagen matrix prepared by introducing into a tissue void or defect a self-assembling biopolymer, and polymerizing the self-assembling biopolymer to form a shape-retaining matrix, wherein a pH of the self-assembling biopolymer ranges from about 5.5 to about 8.5, wherein a self-assembly time of the self-assembling biopolymer ranges from about 0.2 minutes to about 1.5 minutes, wherein a shear storage modulus (G') of the collagen matrix ranges from about 2.0 kPa to about 4.0 kPa, wherein a shear loss modulus (G") of the collagen matrix ranges from about 0.1 kPa to about 0.7 kPa, and wherein a compression modulus of the collagen matrix ranges from about 5.0 kPa to about 10.0 kPa.
177. The collagen matrix of clause 176 wherein the pH of the self-assembling biopolymer is about 7.25±about 0.25, wherein the self-assembly time of the self-assembling biopolymer is about 0.8 minutes±about 0.3 minutes, wherein the shear storage modulus (G') of the collagen matrix is about 3.1 kPa±about 0.4 kPa, wherein the shear loss modulus (G") of the collagen matrix is about 0.4 kPa±about 0.1 kPa, and wherein the compression modulus of the collagen matrix is about 7.7 kPa±about 1.9 kPa.
178. The collagen matrix of clause 176 or clause 177 wherein the collagen matrix is a medical graft.
179. The collagen matrix of any one of clauses 176-178 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.
180. The collagen matrix of any one of clauses 176-179 wherein the collagen matrix is used for research purposes.
181. The collagen matrix of any one of clauses 176-180 wherein the collagen matrix is used for drug toxicity testing or drug development.
182. The collagen matrix of any one of clauses 176-181 wherein the collagen matrix is sterilized using ultraviolet radiation.
183. The collagen matrix of any one of clauses 176-182 wherein the collagen matrix maintains a polymerization property relative to a collagen matrix that is not irradiated.
184. The collagen matrix of any one of clauses 176-183 wherein the polymerization property is shear storage modulus.
185. The collagen matrix of any one of clauses 176-184 wherein the radiation dose ranges from about 5 mJ/cm$^2$ to about 800 mJ/cm$^2$.
186. The collagen matrix of any one of clauses 176-185 wherein the radiation close ranges from about 30 mJ/cm$^2$ to about 300 mJ/cm$^2$.
187. The collagen matrix of any one of clauses 176-186 wherein the sterilization inactivates viruses.
188. The collagen matrix of any one of clauses 176-187 wherein the collagen matrix is sterilized using UVC irradiation.
189. The collagen matrix of any one of clauses 176-188 wherein the collagen matrix is sterilized using UVC irradiation and sterile filtration.
190. A kit for restoring and regenerating tissue in a tissue void or defect, the kit comprising an in-situ polymerizable collagen composition and a buffer solution.
191. The kit of clause 190 wherein the in-situ polymerizable collagen composition comprises a liquid type I collagen.
192. The kit of clause 190 or clause 191 wherein the in-situ polymerizable collagen composition comprises a type I oligomeric collagen derived from porcine dermis.
193. The kit of any one of clauses 190-192 wherein the in-situ polymerizable collagen composition comprises a solution comprising a lyophilized oligomeric collagen and an acid.
194. The kit of any one of clauses 190-193 wherein the in-situ polymerizable collagen composition comprises a solution comprising a lyophilized type I oligomeric collagen and an acid.
195. The kit of any one of clauses 190-194 wherein the polymerizable collagen composition comprises a solution comprising a lyophilized type I oligomeric collagen and hydrochloric acid.
196. The kit of any one of clauses 190-195 wherein a ratio of the in-situ polymerizable collagen composition to the buffer solution is about 9:1.
197. The kit of any one of clauses 190-196 wherein the in-situ polymerizable collagen composition comprises a solution comprising a lyophilized type I oligomeric collagen and 0.01 N hydrochloric acid, and wherein a concentration of the collagen the solution of the in-situ polymerizable collagen composition is about 8 mg/mL based on a dry weight of the lyophilized type I oligomeric collagen.
198. The kit of any one of clauses 190-197 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation.
199. The kit of any one of clauses 190-198 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation and then filtered through a sterile membrane filter.
200. The kit of any one of clauses 190-199 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation, dosed with ultraviolet radiation, and then filtered through a sterile membrane filter.
201. The kit of any one of clauses 190-200 wherein the in-situ polymerizable collagen composition comprises a solution comprising a lyophilized type I oligomeric collagen and hydrochloric acid, and wherein the solution of the in-situ polymerizable collagen composition has been clarified using ultracentrifugation, dosed with 500 mJ/cm$^2$ ultraviolet radiation, and then filtered through a sterile membrane filter.
202. The kit of any one of clauses 190-201 further comprising a syringe configured for delivery of a mixture of the in-situ polymerizable collagen composition and the buffer solution to the tissue void or defect.
203. The kit of any one of clauses 190-202 wherein the buffer solution comprises about 0.03 mM to about 0.2 mM MgCl$_2$.
204. The kit of any one of clauses 190-203 wherein the buffer solution comprises about 0.002 mM to about 0.02 mM MgCl$_2$.
205. The kit of any one of clauses 190-204 wherein the buffer solution comprises less than about 0.02 mM MgCl$_2$.
206. The kit of any one of clauses 190-205 wherein the buffer solution does not comprise MgCl$_2$.
207. The kit of any one of clauses 190-206 wherein the buffer solution further comprises about 0.003 M to about 0.03 M KH$_2$PO$_4$.
208. The kit of any one of clauses 190-207 wherein the buffer solution further comprises about 0.01 M to about 0.1 M Na2HPQ4.
209. The kit of any one of clauses 190-208 wherein the buffer solution further comprises about 0.001 M to about 0.04 M KCl.
210. The kit of any one of clauses 190-209 wherein the buffer solution further comprises about 0.2 M to about 3.0 M NaCl.
211. The kit of any one of clauses 190-210 wherein the buffer solution further comprises about 0.02 N to about 0.2 N
212. The kit of any one of clauses 190-211 wherein the buffer solution further comprises about 0.2 weight percent to about 5 weight percent of glucose.
213. The kit of any one of clauses 190-212 wherein the buffer solution comprises about 0.5 weight percent glucose or less.

214. The kit of any one of clauses 190-213 wherein the buffer solution does not comprise glucose
215. The kit of any one of clauses 190-214 wherein a concentration of collagen in the in-situ polymerizable collagen composition is about 0.1 mg/ml to about 40 mg/ml.
216. The kit of any one of clauses 190-215 wherein a concentration of collagen in the in-situ polymerizable collagen composition is about 7 mg/mL to about 8 mg/mL.
217. The kit of any one of clauses 190-216 wherein a concentration of collagen in a neutralized collagen filler, the neutralized collagen filler comprising the in-situ polymerizable collagen composition and the buffer solution, is about 6.3 to about 7.2 mg/mL.
218. The kit of any one of clauses 190-217 wherein the collagen solution comprises about 0.005 N hydrochloric acid to about 0.1 N hydrochloric acid.
219. The kit of any one of clauses 190-218 wherein the buffer solution is configured to polymerize the in-situ polymerizable collagen composition in a single mixing step comprising mixing the in-situ polymerizable collagen composition with the buffer solution.
220. The kit of any one of clauses 190-219 wherein the in-situ polymerizable collagen composition and the buffer solution are in separate containers.
221. The kit of any one of clauses 190-220 wherein the separate containers comprise sterilized
222. The kit of any one of clauses 190-221 wherein the separate containers comprise separate compartments of a dual-barrel syringe.
223. The kit of any one of clauses 190-222 wherein the dual-barrel syringe comprises a mixing element.
224. The kit of any one of clauses 190-223 wherein the dual-barrel syringe is sterilized.
775. The kit of any one of clauses 190-224 further comprising instructions for use of components of the kit.
226. The kit of any one of clauses 190-225 further comprising at least one therapeutic agent configured for local delivery to the tissue void or defect.
227. The kit of any one of clauses 190-226 wherein the at least one therapeutic agent comprises a chemotherapeutic agent, an anti-inflammatory agent, an antibiotic agent, an analgesic agent, or a combination thereof.
228. The kit of any one of clauses 190-227 wherein the tissue void or defect comprises a wound.
229. The kit of any one of clauses 190-228 wherein the tissue void or defect comprises a surgical wound.
230. The kit of any one of clauses 190-229 wherein the tissue void car defect resulted from removal of a tumor.
231. The kit of any one of clauses 190-230 wherein the tissue void or defect resulted from removal of a breast tumor.
232. The kit of any one of clauses 190-231 wherein the kit is for regenerating tissue following breast conserving surgery.
233. The kit of any one of clauses 190-232 wherein the kit is for preparing a matrix in a tissue void or defect.
234. The kit of any one of clauses 190-233 wherein the in-situ polymerizable collagen composition or the lyophilized oligomeric collagen is sterilized using ultraviolet radiation.
235. The kit of any one of clauses 190-234 wherein a collagen matrix that results from polymerization of the in-situ polymerizable collagen composition maintains a polymerization property relative to a collagen composition this is not irradiated or to lyophilized collagen that is not irradiated, respectively.
236. The kit of any one of clauses 190-235 wherein the polymerization property is shear storage modulus.
237. The kit of any one of clauses 190-236 wherein a dose of the radiation ranges from about 5 mJ/cm$^2$ to about 800 mJ/cm$^2$.
238. The kit of any one of clauses 190-237 wherein a dose of the radiation dose ranges from about 30 mJ/cm$^2$ to about 300 mJ/cm$^2$.
239. The kit of any one of clauses 190-238 wherein sterilization inactivates viruses.
240. The kit of any one of clauses 190-239 wherein the in-situ polymerizable collagen composition or the lyophilized oligomeric collagen is sterilized using UVC irradiation.
241. The kit of any one of clauses 190-240 wherein the collagen composition or the lyophilized oligomeric collagen is sterilized using UVC irradiation and sterile filtration.

Purified, fibril-forming liquid type I collagen derived from porcine dermis for use in accordance with the present teachings is described in Applicant's co-pending U.S. patent application Ser. No. 16/482,465, filed Jul. 31, 2019 and in International Publication No. WO 2018/144496 A1. The entire contents of both documents are incorporated herein by reference in their entireties.

For preparation of the collagen for use in the methods and compositions described herein, any method known in the art for preparing collagen may be used. In illustrative embodiments, the collagen may be prepared by methods described in Bailey J L, Critser P J, Whittington C, Kuske J L, Yoder M C, Voytik-Harbin S L; Collagen oligomers modulate physical and biological properties of three-dimensional self-assembled matrices, *Biopolymers* (2011) 95(2):77-93, Kreger S T, Bell B J, Bailey J, Stites E, Kuske J, Waisner B, Voytik-Harbin S L; Polymerization and matrix physical properties as important design considerations for soluble collagen formulations, *Biopolymers* (2010) 93(8):690-707 U.S. Patent Application Publication Number 20080268052, or U.S. Patent Application Publication Number 20120027732, each of which is incorporated herein by reference.

In various illustrative embodiments, the collagen for use in the methods and compositions described herein may be obtained from any suitable source of collagen known in the art provided at least a portion of the collagen includes polymerizable oligomeric collagen. Exemplary collagen sources include submucosa tissues (U.S. Pat. Nos. 4,902,508, 5,281,422, and 5,275,826), pericardia! tissue, urinary bladder submucosa tissue, stomach submucosa tissue, liver basement membrane tissue, placental tissue, ovarian tissue, animal tail tissue, skin tissue (e.g., Gallop, et al., Preparation and Properties of Soluble Collagens, *Meth. Enzymol.* 6: 635-641 (1963), incorporated herein by reference), and tissues containing extracellular matrix generally. In various embodiments, the type of collagen for use in the methods and compositions described herein may be any suitable type of collagen, including, but not limited to, Type I collagen, Type II collagen, Type III collagen, or Type IV collagen, or combinations thereof.

In some embodiments, a tissue enriched in collagen oligomers (e.g., pig skin tissue) may also be used to obtain the collagen for use in the methods and compositions described herein, or the collagen may be obtained from cells producing collagen oligomers (e.g., cells altered by recombinant techniques to express collagen oligomers) or by chemically crosslinking the collagen to obtain collagen oligomers (e.g., using a cross-linking agent known in the art). In some embodiments, the collagen for use in the methods and compositions described herein may comprise oligomers or may consist of oligomers. In some embodiments, the collagen may comprise oligomers, and other forms of collagen such as monomers, telocollagen, and/or atelocollagen.

In another embodiment, the collagen may be soluble collagen or solubilized collagen. In the embodiments where the collagen is soluble collagen or solubilized collagen, the collagen is substantially free of insoluble collagen, but may contain some insoluble collagen. In another embodiment, the collagen consists of soluble collagen or solubilized collagen.

In various illustrative embodiments, the collagen, the collagen composition, the collagen matrix, the collagen solution, the lyophilized collagen, and/or the buffer solution (also referred to herein as a neutralization buffer or a self-assembly reagent) may be sterilized using sterilization techniques known in the art, including but not limited to, propylene oxide or ethylene oxide treatment, gas plasma sterilization, gamma radiation (e.g., 0.1-10 Mrad), ultraviolet radiation (e.g., UVC irradiation), electron beam, viral filtration, sterile filtration (e.g., with a 0.22 µm filter), chloroform exposure, and/or peracetic acid sterilization, and combinations thereof. In this embodiment, the sterilization procedure should not adversely affect the structure of collagen, the polymerization properties of the collagen, or the biological properties of the collagen that is sterilized. In various embodiments, the collagen may be sterilized before or after lyophilization (lyophilization procedures are described below).

In embodiments that include ultraviolet radiation (e.g., UVC irradiation), the collagen matrix that results from collagen polymerization may maintain a polymerization property relative to collagen that is not irradiated, a collagen composition this is not irradiated, a collagen matrix that is not irradiated, a collagen solution that is not irradiated, or lyophilized collagen that is not irradiated, respectively. In such embodiments, the polymerization property may be selected from shear storage modulus, elastic modulus (Young's modulus), tensile modulus, compressive modulus, fibril architecture, proteolytic degradation, cellular signaling, and combinations thereof. In various embodiments, the ultraviolet radiation dose (e.g., UVC irradiation) may range from about 5 mJ/cm$^2$ to about 800 mJ/cm$^2$, about 5 mJ/cm$^2$ to about 700 mJ/cm$^2$, about 5 mJ/cm$^2$ to about 600 mJ/cm$^2$, about 5 mJ/cm$^2$ to about 500 mJ/cm$^2$, about 5 mJ/cm$^2$ to about 400 mJ/cm$^2$, about 5 mJ/cm$^2$ to about 300 mJ/cm$^2$, 5 mJ/cm$^2$ to about 200 mJ/cm$^2$, 5 mJ/cm$^2$ to about 100 mJ/cm$^2$, 5 mJ/cm$^2$ to about 50 mJ/cm$^2$, about 30 mJ/cm$^2$ to about 800 mJ/cm$^2$, about 30 mJ/cm$^2$ to about 700 mJ/cm$^2$, about 30 mJ/cm$^2$ to about 600 mJ/cm$^2$, about 30 mJ/cm$^2$ to about 500 mJ/cm$^2$, about 30 mJ/cm$^2$ to about 400 mJ/cm$^2$, about 30 mJ/cm$^2$ to about 300 mJ/cm$^2$, about 30 mJ/cm$^2$ to about 200 mJ/cm$^2$, about 30 mJ/cm$^2$ to about 100 mJ/cm$^2$, about 30 mJ/cm$^2$ to about 50 mJ/cm$^2$, about 200 mJ/cm$^2$ to about 800 mJ/cm$^2$, about 300 mJ/cm$^2$ to about 800 mJ/cm$^2$ about 400 mJ/cm$^2$ to about 800 mJ/cm$^2$, about 500 mJ/cm$^2$ to about 800 mJ/cm$^2$, about 600 mJ/cm$^2$ to about 800 mJ/cm$^2$, about 50 mJ/cm$^2$ to about, 300 mJ/cm$^2$, about 100 mJ/cm$^2$ to about 300 mJ/cm$^2$, or about 200 mJ/cm$^2$ to about 300 mJ/cm$^2$. In all of the ultraviolet radiation embodiments (e.g., UVC irradiation) described herein, the sterilization inactivates viruses. In this embodiment, "inactivates viruses" means inactivating all viruses, whether infectious or not, reducing the number of infectious viruses, or inhibiting the activity of viruses, whether infectious or not.

In one aspect, the collagen for use in the methods and compositions described herein may be purified by methods known in the art for purifying collagen. As used herein, "purified" means removing contaminants including, but not limited to, cellular contaminants, nucleotide contaminants, and endotoxins. In various embodiments, the collagen may be purified by removing contaminants so that it is at least about 90%, at least about 91%, at least about 92%, at least about 93%, at least about 94%, at least about 95%, at least about 96%, at least about 97%, at least about 98%, at least about 99%, or at least about 99.5% pure. In other embodiments, the collagen may be isolated. As used herein "isolated" means substantially free of contaminants including, but not limited to, cellular contaminants, nucleotide contaminants, and endotoxins.

In some embodiments, the collagen for use in the methods and compositions described herein may be lyophilized and then reconstituted to form the collagen composition for mixing with the buffer solution as described herein. In such embodiments, the reconstitution of the lyophilized collagen is not a mixing step for polymerization of the collagen. As used herein, the term "lyophilized" means that water is removed from the protein, compound, or composition, by, for example, freeze-drying under a vacuum. Any lyophilization method known to the skilled artisan may be used. In some embodiments, the collagen may be lyophilized in an acid, for example, acetic acid, hydrochloric acid, formic acid, lactic acid, citric acid, sulfuric acid, or phosphoric acid. In other embodiments, the collagen may be lyophilized in water. In further embodiments, cryoprotectants or lyoprotectants, or combinations thereof, may be used during the lyophilization.

In some embodiments, the lyophilized collagen may be reconstituted to form the collagen composition described herein for mixing with the buffer solution to polymerize the collagen. In some embodiments, the collagen may be reconstituted in an acidic solution or in water. In some embodiments, the acidic solution may comprise acetic acid, hydrochloric acid, formic acid, lactic acid, citric acid, sulfuric acid, or phosphoric acid. In some embodiments, the acidic solution for reconstitution may have a concentration of the acid of from about 0.005 N to about 0.1 N, from about 0.005 N to about 0.08 N, from about 0.005 N to about 0.06 N, from about 0.005 N to about 0.04 N, from about 0.005 N to about 0.02 N, from about 0.005 N to about 0.01 N, or about 0.01 N. In some embodiments, the acid may be hydrochloric acid and the hydrochloric acid may be about 0.005 N to about 0.1 N hydrochloric acid. In other embodiments, the acid may be hydrochloric acid and the hydrochloric acid may be about 0.01 N hydrochloric acid.

In some embodiments, the collagen concentration in the collagen composition or in the collagen solution may be from about 0.1 mg/ml to about 40 mg/ml, from about 0.1 mg/ml to about 5 mg/ml, or from about 0.5 mg/ml to about 4 mg/ml. In other embodiments, the collagen concentration in the collagen composition or in the collagen solution may be from about 0.05 to about 5.0 mg/ml, about 1.0 mg/ml to about 3.0 mg/ml, about 0.05 mg/ml to about 10 mg/ml, about 0.05 to about 20 mg/ml, about 0.05 to about 30 mg/ml, about 0.05 to about 40 mg/ml, about 0.05 to about 50 mg/ml, about 0.05 to about 60 mg/ml, about 0.05 to about 80 mg/ml, about 5 mg/ml to 10 mg/ml, about 5 mg/ml to 20 mg/ml, about 5 mg/ml to about 40 mg/ml, about 5 mg/ml to 60 mg/ml, about 5 mg/ml to about 100 mg/ml, about 20 mg/ml to about 40 mg/ml, about 20 mg/ml to 60 mg/ml, or about 20 mg/ml to about 100 mg/ml.

In some embodiments, the collagen composition is mixed in a single step with the buffer solution to polymerize the collagen. In other embodiments, the collagen composition is mixed with the buffer solution in the absence of magnesium or manganese ions to polymerize the collagen. In some embodiments, the collagen composition is mixed with the buffer solution to form the collagen solution and the collagen solution is incubated at a temperature greater than about 25° C. to promote polymerization of the collagen in the collagen solution. In other embodiments, the collagen solution may be incubated at about 37° C. to promote polymerization of the collagen in the collagen solution. In some embodiments, the collagen solution may be incubated at about 25° C., 26° C., 27° C., 28° C., 29° C., 30° C., 31° C., 32° C., 33° C., 34° C., 35° C., 36° C., 38° C., 39° C., or 40° C., to promote polymerization of the collagen in the collagen solution. In other embodiments, the collagen solution may be incubated at from about 25° C. to about 40° C. to promote polymerization of the collagen in the collagen solution. In other embodiments, the polymerization may be conducted at temperatures above 20° C., or at a temperature selected from the range of about 20° C. to about 40° C. In such embodiments, the collagen may be polymerized to form fibrils similar to those found in the body.

In some embodiments, the buffer solution to be mixed with the collagen composition to form the collagen solution may comprise about 0.03 mM to about 0.2 mM $MgCl_2$, about 0.002 mM to about 0.02 mM MgCl2, less than about 0.02 mM MgCl2, or no MgCl2. In other embodiments, the buffer solution to be mixed with the collagen composition to form the collagen solution may comprise about 0.3 mM to about 3 mM KH2PO4, about 1 mM to about 10 M Na2HPO$_4$, about 0.1 mM to about 4 mM KCl, about 0.02 M to about 0.3 M NaCl, and about 0.002 N to about 0.02 N NaOH. In other embodiments, the buffer solution to be mixed with the collagen composition to form the collagen solution may comprise about 0.5 weight percent to about 5 weight percent of glucose, about 0.5 weight percent glucose or less, or no glucose.

In some embodiments, the buffer solution may be diluted from a 10×, 5×, 2×, or any suitable starting concentration, to make a 1× buffer solution having any of the component concentrations in the preceding paragraph. In some embodiments, a kit in accordance with the present teachings may contain a buffer solution with a concentration of 10×, 5×, or 2×, or any suitable starting concentration, for dilution to make a 1× buffer solution. In some embodiments, the 10× buffer solution may comprise the following ingredients at the following concentrations:

1.37 M NaCl
0.027 M KCl
0.081 M $Na_2HPO_4$
0.015 M $KH_2PO_4$
0.1 NNaOH
and, optionally, 55.5 mM glucose In other embodiments, a 1× buffer solution may comprise the following ingredients at the following concentrations:

0.137 M NaCl
0.0027 M KCl
0.0081 M $Na_2HPO_4$
0.0015 M $KH_2PO_4$
0.01 NNaOH
and, optionally, 5.55 mM glucose In these embodiments, NaOH is present in the buffer solution. In conventional previously known methods for polymerizing collagen, the NaOH was added separately as an additional mixing step in the methods for polymerization of collagen. In some embodiments, calcium chloride may be present in the buffer solution at a concentration of about 0.4 mM to about 2.0 mM.

In some embodiments, the buffer in the buffer solution may be selected from the group consisting of phosphate buffer saline (PBS), Tris (hydroxymethyl) aminomethane Hydrochloride (Tris-HCl), 3-(N-Morpholino) Propanesulfonic Acid (MOPS), piperazine-n,n'-bis (2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES), and 1,3-bis[tris(Hydroxymethyl) methylamino]propane (Bis Tris Propane). In some embodiments, the buffer is PBS.

In some embodiments, the pH of the collagen solution for the polymerization of collagen is selected from the range of about 5.0 to about 11, about 6.0 to about 9.0, about 6.5 to about 8.5, and in some embodiments, the pH is about 7.3 to about 7.4.

In some embodiments, nutrients, including minerals, amino acids, sugars, peptides, proteins, vitamins, or glycoproteins that facilitate cellular proliferation, such as laminin and fibronectin, hyaluronic acid, or growth factors such as epidermal growth factor, platelet-derived growth factor, transforming growth factor beta, or fibroblast growth factor, and glucocorticoids such as dexamethasone, may be added to the collagen solution before or after collagen polymerization is complete or during collagen polymerization. In other embodiments, cells may be added to the collagen solution before or after collagen polymerization is complete or during collagen polymerization. In some embodiments, the cells may be selected from the group consisting of epithelial cells, endothelial cells, mesodermally-derived cells, mesothelial cells, synoviocytes, neural cells, glial cells, osteoblasts, fibroblasts, chondrocytes, tenocytes, smooth muscle cells, skeletal muscle cells, cardiac muscle cells, multi-potential progenitor cells (e.g., stem cells, including bone marrow progenitor cells, induced pluripotent stem cells), adipocytes, osteogenic cells, and specific cell derivatives from pluripotent stem cells.

In some embodiments, a collagen matrix prepared according to the any of the methods described herein is provided. In some embodiments, the collagen matrix may be a medical graft. In some embodiments, the medical graft has a use selected from the group consisting of a tissue graft material, an injectable graft material, a wound dressing, a hemostatic dressing, a delivery vehicle for therapeutic cells, and a delivery vehicle for a therapeutic agent. In other embodiments, the methods described herein may be used to make a bioink formulation for printing tissues or organs. In other embodiments, the collagen matrix is used for research purposes, such as drug toxicity testing or drug development. In some embodiments, the matrices prepared by the methods described herein may serve as substrates for the regrowth of endogenous tissues at the implantation site (e.g., remodeling), and the matrices may have the characteristics of the damaged or diseased tissues that they replace at the site of implantation or injection.

In some embodiments, the matrices described herein may contain fibrils with a fibril area fraction (defined as the percent area of the total area occupied by fibrils in a cross-sectional surface of the matrix) or a fibril volume fraction (the percent area of the total area occupied by fibrils in 3 dimensions) of about 0.1% to about 100%, about 0.5% to about 100%, about 0.5% to about 26%, about 1% to about 100%, about 1% to about 26%, about 1% to about 7%, about 1% to about 15%, of about 7% to about 26%, about 20% to about 30%, about 20% to about 50%, about 20% to about 70%, about 20% to about 100%, about 30% to about 50%, about 30% to about 70%, or about 30% to about 100%, and/or a modulus (e.g., an elastic or linear modulus defined by the slope of the linear region of the stress-strain curve obtained using conventional mechanical testing protocols; i.e., stiffness), a compressive modulus, or a shear storage modulus) of about 0.5 kPa to about 40 kPa, about 30 kPa to 100 kPa, about 30 kPa to about 1000 kPa, about 30 kPa to about 10000 kPa, about 30 kPa to about 70000 kPa, about 100 kPa to 1000 kPa, about 100 kPa to about 10000 kPa, or about 100 kPa to about 70000 kPa.

In some embodiments, a kit comprising lyophilized collagen, a hydrochloric acid solution, and a buffer solution is provided. In other embodiments, a kit comprising a collagen composition and a buffer solution is provided. In these kit embodiments, the buffer solution may comprise about 0.03 mM to about 0.2 mM $MgCl_2$, about 0.002 mM to about 0.02 mM $MgCl_2$, less than about 0.02 mM MgCl2, or the buffer solution does not comprise MgCl2. In various embodiments, the buffer solution further comprises about 0.003 M to about 0.03 M $KH_2PO_4$, about 0.01 M to about 0.1 M $Na_2HPO4$, about 0.001 M to about 0.04 M KCl, about 0.2 M to about 3.0 M NaCl, and about 0.02 N to about 0.2 N NaOH. In other embodiments, the buffer solution may comprise about 0.2 weight percent to about 5 weight percent of glucose, about 0.5 weight percent glucose or less, or no glucose.

In some embodiments of a kit that contain a hydrochloric acid solution, the hydrochloric acid solution may comprise about 0.005 N hydrochloric acid to about 0.1 N hydrochloric acid. In embodiments of a kit that contain lyophilized collagen, a hydrochloric acid solution, and a buffer solution, the lyophilized collagen, the hydrochloric acid solution, and the buffer solution may be provided in separate containers. In embodiments of a kit that contain the collagen composition and the buffer solution, the collagen in the collagen composition may be at a concentration of about 0.1 mg/ml to about 40 mg/ml or about 0.1 mg/ml to about 10 mg/ml. In some embodiments, the collagen composition has a concentration of between about 7 mg/mL and about 8 mg/mL. In some embodiments, a concentration of the collagen in the mixture of the collagen solution and the buffer solution is about 6.3 to about 7.2 mg/mL. In some embodiments, upon neutralization, the formulation yields a polymerizable collagen with one or more of the following features: final collagen concentration: 6.3-7.2 mg/mL; polymerization time: 0.5-1.1 minutes; shear storage modulus: 2.7-3.5 kPa; shear loss modulus: 0.3-0.5 kPa; and/or compression modulus: 5.8-9.6 kPa. In such embodiments, the collagen composition and the buffer solution may be provided in separate containers, such as sterilized vials or separate compartments of a dual syringe comprising a mixing element. In any of the kit embodiments described herein, the kit may further comprise instructions for use of components of the kit. In any of the kit embodiments described herein, the buffer solution may be capable of polymerizing collagen using a single mixing step comprising mixing the buffer solution with the lyophilized collagen reconstituted in the hydrochloric acid solution or with the collagen composition.

In some embodiments, a kit is provided with collagen in a lyophilized form and the kit further comprises a buffer solution as described herein and a solution of an acid, such as acetic acid, or another dilute acid including for example, hydrochloric acid, formic acid, lactic acid, citric acid, sulfuric acid, or phosphoric acid for reconstituting the lyophilized collagen.

The following examples illustrate specific embodiments in further detail. These examples are provided for illustrative purposes only and should not be construed as limiting the invention in any way.

EXAMPLES

Example 1

Methods and Materials

Two collagen tissue filler formulations that differed by a single, proprietary manufacturing step were prepared by GeniPhys and evaluated; however, since no difference in performance was observed, results were combined and presented as a single formulation. For both formulations, lyophilized type I oligomeric collagen was dissolved in 0.01 N hydrochloric acid to obtain an estimated 8 mg/ml solution (based on lyophilized material dry weight). After solubilization, the solutions were clarified using ultracentrifugation (142,400×g). Formulation 1 was then filtered through a sterile 0.2 μm membrane filter (SterliTech, Kent, WA) and subjected to the quality control testing described below. Formulation 2 was dosed with 500 mJ/$cm^2$ ultraviolet (UV) radiation using a 254-nm wavelength collimated beam before filtration through the same type of membrane filter and quality control testing. The proprietary neutralization solution was prepared according to GeniPhys standard procedures and sterile filtered through a 0.2 μm filter. To prepare the kits used in surgery, syringes were aseptically filled with formulation 1, formulation 2, and the neutralization solution. The volume ratio of oligomeric collagen solution to neutralization solution used was 9:1.

Material properties of the collagen formulations were defined and quality controlled based on assessment of molecular purity, self-assembly kinetics, and viscoelastic mechanical properties. Self-assembly kinetics and viscoelastic properties were measured in replicates of 6 to 8 (n=6-8) for four independent collagen prototype batches (N=4). To evaluate collagen purity, sodium dodecyl sulfate polyacrylamide gel electrophoresis (SDS-PAGE) was performed on collagen samples and molecular weight standards (Novex SeeBlue Plus2, Invitrogen, Carlsbad, CA) using 4-20% and 6% gels (Invitrogen) and stained with Coomassie Blue (Sigma-Aldrich, St. Louis, MO) according to established methods. Collagen concentration was determined using a Sirius Red (Direct Red 80, Sigma-Aldrich) assay. Time-dependent oscillatory shear rheometry was performed to determine self-assembly kinetics and shear storage (G') and loss (G") moduli. Briefly, neutralized oligomeric collagen samples were tested on an AR2000 rheometer (TA instruments, New Castle, DE), with a 40-mm parallel plate geometry and solvent trap. Prior to sample loading and during the first 2 minutes of testing, the Peltier plate was maintained at 4° C. Oscillatory shear measurements were: taken at 1% strain for this initial 2 minutes and continued for 10 minutes after the temperature was increased to 37° C. Following oscillatory shear testing, the sample was subjected to unconfined compression testing at a strain rate of 20 μmis. To define the kinetics of matrix formation, a plot of shear storage modulus over time was created, and the time at which the collagen reached its maximum stiffness (G') was defined as the polymerization time. This point was also used to define matrix G' and G" values. To obtain the compression modulus, stress-strain curves were created from the unconfined compression data and the slope was calculated in a specified low strain region (20-40% strain), corresponding to the low stress/strain moduli that are reported in literature for soft tissue (e.g., human breast). Four independent batches of prototype collagens were tested with 6 to 8 replicates per batch (N=4 batches; n=6-8 replicates per batch).

Example 2

Porcine Simulated Lumpectomy Model

The mammary glands of miniature swine are routinely used for testing new strategies to improve functional and cosmetic outcomes following breast surgical procedures, including lumpectomy and mastectomy. Simulated lumpectomies were performed on female Yucatan mini-pigs weighing between 45-65 kg using a protocol that was approved by the Purdue Animal Care and Use Committee was used. A total of 8 pigs were used in two studies-6 for a longitudinal study and 2 for a radiation study. For both studies, breasts were randomly assigned to experimental and control groups, with no fill and no surgery serving as negative and positive controls respectively. Post-surgical assessments for the longitudinal study were performed at 1-, 4-, and 16-week time points (2 animals per time point) to achieve twelve replicates (n=12; n=6 for each collagen filler formulation) for the collagen filler group and six replicates (n=6) for each no fill and no surgery groups. For the radiation study, post-surgical assessments were performed 4 and 16 weeks following surgery with six replicates (n=6) for the collagen filler group, three replicates (n=3) for the no fill group, and one (n=1) replicate for the no surgery group. The most caudal pair of mammary glands served as non-irradiated no surgery controls. Outcomes from irradiated animals were compared to non-irradiated animals from the longitudinal study. Post-surgical assessments at each time point included: semi-quantitative scoring of breast/surgical site gross appearance and uniformity/consistency, ultrasonography, radiography, gross explant evaluation and histopathological analysis. Both semi-quantitative scoring and histopathological analysis were performed in a blinded fashion.

Animals were anesthetized, intubated, and placed in dorsal recumbency. For each simulated lumpectomy, a 3-cm skin incision was made using a scalpel, with incisions oriented transversely and placed immediately lateral to the nipple-areolar complex of each breast. Approximately one quarter of the mammary tissue was excised using electrocautery and its volume measured using a standard volume displacement method. A subset of excised normal mammary tissue was subjected to unconfined compression testing (strain rate: 1 mm/min, compression modulus determined in linear region of 20-40% strain) for characterization of mechanical properties. Titanium marker clips (Ethicon Small LigaClips, West CMR, Clearwater, FL) were placed in a subset of animals to facilitate margin identification of collagen and no fill treated surgical sites. For collagen filler-treated sites, neutralized liquid collagen was used to fill the surgical void. Negative control sites received no fill (untreated). A subset of pig breasts that were not subjected to surgery served as positive controls. All surgical sites were closed using resorbable sutures and bandaged with a non-adherent pad (McKesson, San Francisco, CA) and Tegaderm (3M, St. Paul, MN) dressing. The animals' health status was monitored daily based on appetite, attitude, movement, and elimination.

Example 3

Adjunct, Post-Lumpectomy Radiation

To address the question of how radiation therapy affects the tissue response to collagen tissue fillers, two animals were treated with radiation following simulated lumpectomy and treatment. Pig breasts were again randomly assigned to treatment groups, with no fill treatment and breasts on which no surgery was performed serving as negative and positive controls, respectively. Two weeks following surgery, a 6 MV Varian EX clinical linear accelerator with a 120-leaf multi-leaf collimator (Varian, Palo Alto, CA) was used to deliver a total dose of 20 Gy to the cranial 5 pairs of mammary glands in 5 consecutive-day fractions using a CT-based 3D-CRT technique. The caudal pair of mammary glands were excluded as non-irradiated controls.

Example 4

Post-Surgical Procedures and Assessment

At designated time points, the animals were anesthetized, and each breast evaluated using a semi-quantitative scoring system for gross breast/surgical site appearance, including erythema/eschar formation and edema formation, and breast uniformity/consistency scoring as shown in FIG. 10. Additionally, ultrasound imaging of each mammary gland was performed with a Mindray M7 ultrasound machine (Mindray North America, Mahwah, NJ) and a linear 4-7 MHz transducer. Following euthanasia, a mastectomy was performed on each breast, maintaining all surgical sites, any implant, and the surrounding tissue. Each breast was placed in 10% buffered formalin and radiographed using an InnoVet Select Radiograph unit (Summit, Niles, IL) with a Genesis Vet DR plate installed using Genesis VxVue acquisition software (Genesis Digital Imaging, Los Angeles, CA), prior to processing for histopathological analysis.

Example 5

Histopathology

Formalin-fixed explanted tissues were bisected and imaged prior to paraffin embedding and sectioning. Sections were stained with hematoxylin and eosin (H&E). To detect epithelial cells, sections were stained for pan cytokeratin (ab9377, Abeam, Cambridge, MA) at a dilution of 1:100 and then treated with secondary DyLight 488 goat anti-rabbit (DI-1488, Vector Labs. Burlingame, CA) at 6 µg/mL Nuclei were counterstained with DAPI (4',6-diamidino-2'-phenylindole, dihydrochloride; EN62248, Pierce Biotechnology, Rockford, IL). Images were acquired using a Aperio VERSA 8 whole-slide scanner (Leica Biosystems, Buffalo Grove, IL).

Example 6

Liquid Collagen Conforms to Geometry and Transitions to Stable, Fibrillar Matrix with Properties Similar to Soft Tissues Collagen tissue filler formulations specifically designed to serve as a restorative and regenerative filler for damaged or defective tissues, such as the tissue void created by BCS, were evaluated. Collagen tissue filler formulations were defined based on their material compositional and mechanical properties including molecular purity, collagen content, polymerization (self-assembly) time, and viscoelastic properties when subjected to oscillatory shear and unconfined compressive loading. To evaluate biocompatibility and effectiveness of the tissue filler, simulated lumpectomy procedures were performed by a fellowship-trained breast surgeon on the breasts (mammary glands) of pigs. Prototype formulations were then used to fill a subset of the breast voids, and surgical outcomes were compared to untreated defects (no fill; negative control), which represents standard of care for BCS. Normal breasts on which no surgery was performed served as positive controls. To define the tissue response timeline and gain insight into tissue filler mechanism of action (tissue-implant response), a longitudinal study was performed with 1-, 4-, and 16-week time points. At the 1-week time point, a small number of sites was used to determine if the material compromised or interfered with surgical re-excision procedures. A second study was then conducted to assess how the tissue filler and its associated tissue response was affected by irradiation, which is often used as post-operative therapy to prevent local cancer recurrence. Outcome measures included visual examination and palpation of all breasts and surgical sites, with semi-quantitative assessments of erythema, eschar, edema, and breast uniformity/consistency. Additionally, whole breasts were imaged using ultrasonography and radiography. Finally, following euthanasia, breast explants were collected for gross and histological analyses. Combined, these data provide support for improved healing outcomes following use of the tissue filler during breast conserving surgery.

Collagen tissue filler formulations were obtained as kits from GeniPhys (Zionsville, Indiana). As shown in FIG. 1A, the kit consisted of a syringe containing sterile type I oligomeric collagen in dilute acid (0.01 N hydrochloric acid), a syringe containing the sterile neutralization solution (buffer), a sterile luer-lock adapter, and a sterile applicator tip. The oligomeric collagen component of these kits was manufactured and quality-controlled from hides of closed herd pigs in accordance with ASTM F3089-14 guidelines for polymerizable collagens. Immediately prior to use, the two syringes were joined with the luer-lock adapter (FIG. 1B) and the collagen and neutralization reagent mixed at a ratio of 9:1, bringing the collagen solution to physiologic pH and ionic strength. After mixing, the viscous liquid could be injected into various geometries, where it conformed to the shape prior to transitioning into a physically stable, fibrillar collagen matrix (FIG. 1B). To demonstrate collagen purity, sodium dodecyl sulfate polyacrylamide gel electrophoresis (SDS-PAGE) was performed using 4-20% and 6% gels. Gels revealed a banding pattern characteristic of oligomeric collagen with no detectable contaminating non-collagenous proteins or other types of collagens (FIG. 1C). Other functional performance parameters, including polymerization time of the neutralized collagen tissue filler solution and viscoelastic properties of the matrix formed by the tissue filler, were measured, with a summary provided in FIG. 1D. Specifically, the concentration of oligomeric collagen prior to neutralization was roughly 7.7 mg/mL. Upon neutralization, the matrix-forming reaction took, on average, just under 1 minute, as measured rheometrically at 37° C. When analyzed in oscillatory shear and unconfined compression, the formed matrix exhibited solid-like behavior with shear storage (G') and loss (G") moduli of 3.16±0.16 kPa and 0.40±0.02 kPa, respectively, and a compressive modulus of 7.67±0.42 kPa. Although oligomeric collagen may be used to create a broad variety of polymeric materials with tunable combinations of compositional and mechanical properties (i.e., elastic modulus and strength values), the specific tissue filler formulation developed and tested here, was designed with a specific combination of material properties so to exhibit viscoelastic mechanical properties similar to soft tissues.

Example 7

Collagen Tissue Filler Matrix Maintains Volume and Induces Vascularization and Breast Tissue Formation without Evoking an Inflammatory Response Typically Observed During Healing or a Foreign Body Reaction Typically Observed with Tissue-Implant Responses To evaluate the effectiveness of the tissue filler to improve restoration of the appearance, structure, and function of soft tissue defects, a longitudinal study was performed involving simulated lumpectomy procedures on breasts of normal, healthy Yucatan mini-pigs (FIG. 2). Female mini-pigs represent the preferred large animal model for such translational studies based on their size and anatomical and physiological similarities to humans. Additionally, pigs generally have twelve mammary glands (breasts), which reduced the total number of animals required for the studies since each breast could serve as an experimental or control group. Prior to surgery, pig breasts were randomly assigned to a treatment group, with no fill and breasts receiving no surgery serving as negative and positive controls, respectively. All surgical procedures and breast evaluations were performed by a fellowship-trained breast surgeon. Roughly one quarter of breast tissue volume was excised (FIG. 2E), which ranged from 2 to 5.5 mL of tissue (average ~3 mL) depending upon individual breast size (FIG. 2A). For tissue filler-treated breasts, the liquid collagen was mixed and immediately injected into the tissue void, where it conformed to the complex geometry prior to transitioning to a fibrillar collagen matrix in less than 5 minutes under these circumstances (FIG. 2B-D). The breast surgeon used her discretion when filling each defect, with applied collagen volumes varying with defect size and geometry. Surgical voids were filled with at least the same volume of collagen as tissue removed, with the majority receiving 1-2 mL more collagen volume. Negative control sites were left untreated (no fill), which is consistent with standard-of-care BCS procedures. All incisions were closed using resorbable sutures and bandaged (FIG. 2F). All animals maintained weight (±5 kg), surgical sites remained closed, and no procedural complications occurred throughout the duration of the study (FIG. 2G).

Consistent with what is observed amongst women and men, pig breasts were found to vary in volume, consistency, and composition both within and between individual animals. At the microscopic level (FIG. 9), mammary glands consisted of multiple lobes, composed of smaller secretory lobules organized as clusters and a system of ducts (channels) that eventually exited the skin via the nipple. The lobules and ducts were supported by an intralobular stroma, composed predominantly of fibrous type I collagen. Additionally, collagenous connective tissue was found between lobes (interlobular stroma), providing support to the breast and determining its shape. Adipose tissue, which primarily determines breast size, filled the space between the glandular and fibrous connective tissue. When evaluated in unconfined compression, breasts located cranially (toward the head) were relatively stiff, with an average compression modulus of 19.0±12.9 kPa. Progressing caudally (toward the tail), breasts increased in fat composition and were softer, with an average compression modulus of 6.56±2.51 kPa for the most caudal breasts.

To assess biocompatibility and tissue response of the collagen filler, animals were anesthetized at designated time points of 1, 4, and 16 weeks. All breasts were examined visually, palpated, and semi-quantitatively scored in a blinded fashion according to criteria in FIG. 10. Collagen-treated and no fill control breasts showed no evidence of erythema (redness) or eschar (sloughing, dead tissue) at any time point. Mild edema was evident at 1 week in breasts on which surgery was performed; however, the extent of swelling was similar for both collagen and no fill groups and subsided shortly thereafter. Uniformity/consistency scores for collagen-treated breasts were similar to no fill controls at all three time points, decreasing from roughly 1.2 at 1 week to 0.25 by 16 weeks (FIG. 3A). Such findings are important because they indicate that the collagen filler does not create breast inconsistencies that could be interpreted clinically as residual disease or a source of patient discomfort. All normal breasts received a score of zero. Additionally, when the breast surgeon performed simulated surgical re-excision on collagen-treated breasts, the fill material did not compromise or interfere with the procedure.

Figure 4A:
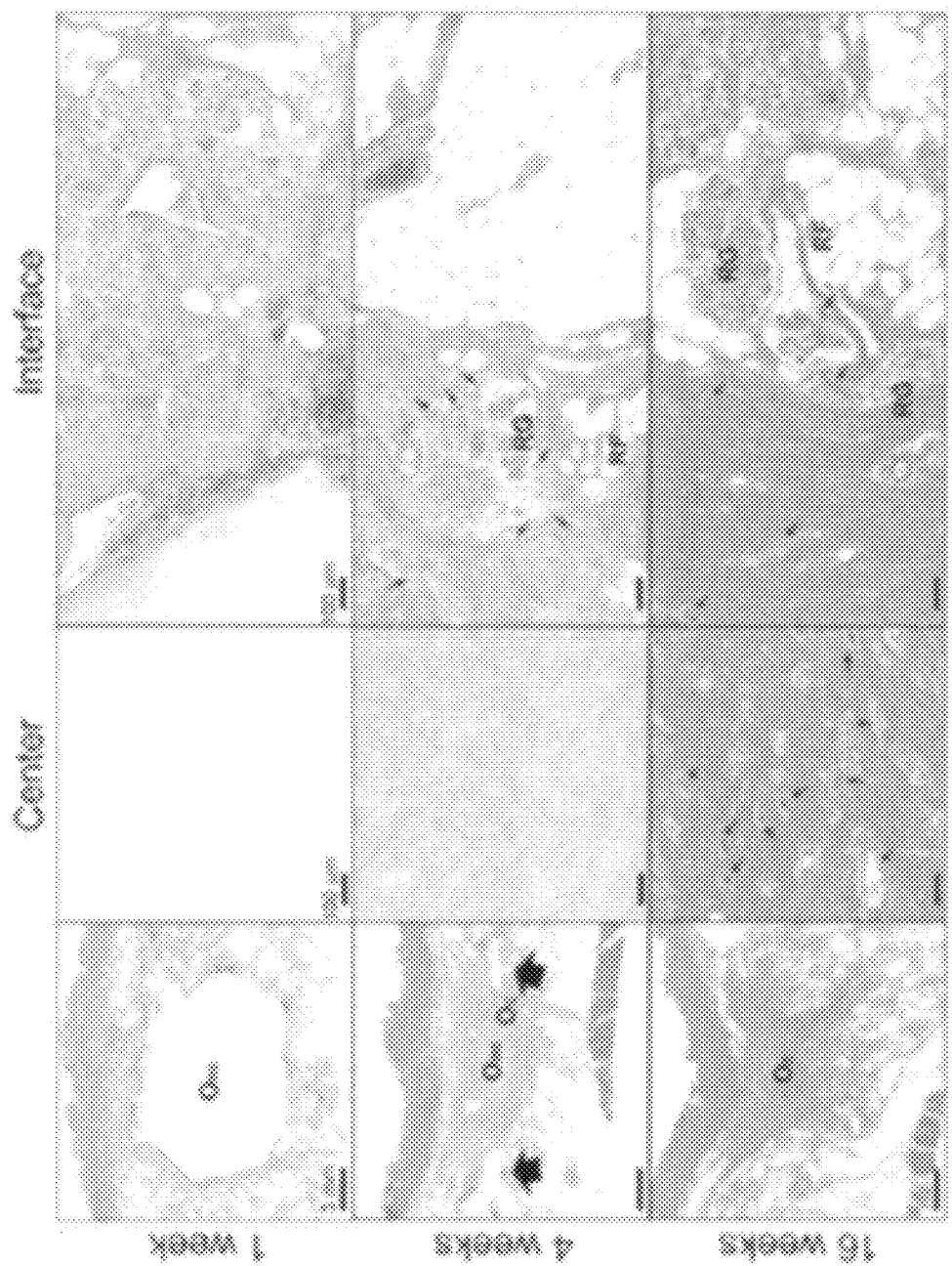
FIGS. 4A-4B show an overview of how tissue filler supports formation of breast tissue without evoking an inflammatory response or foreign body reaction.
Figure 4B:
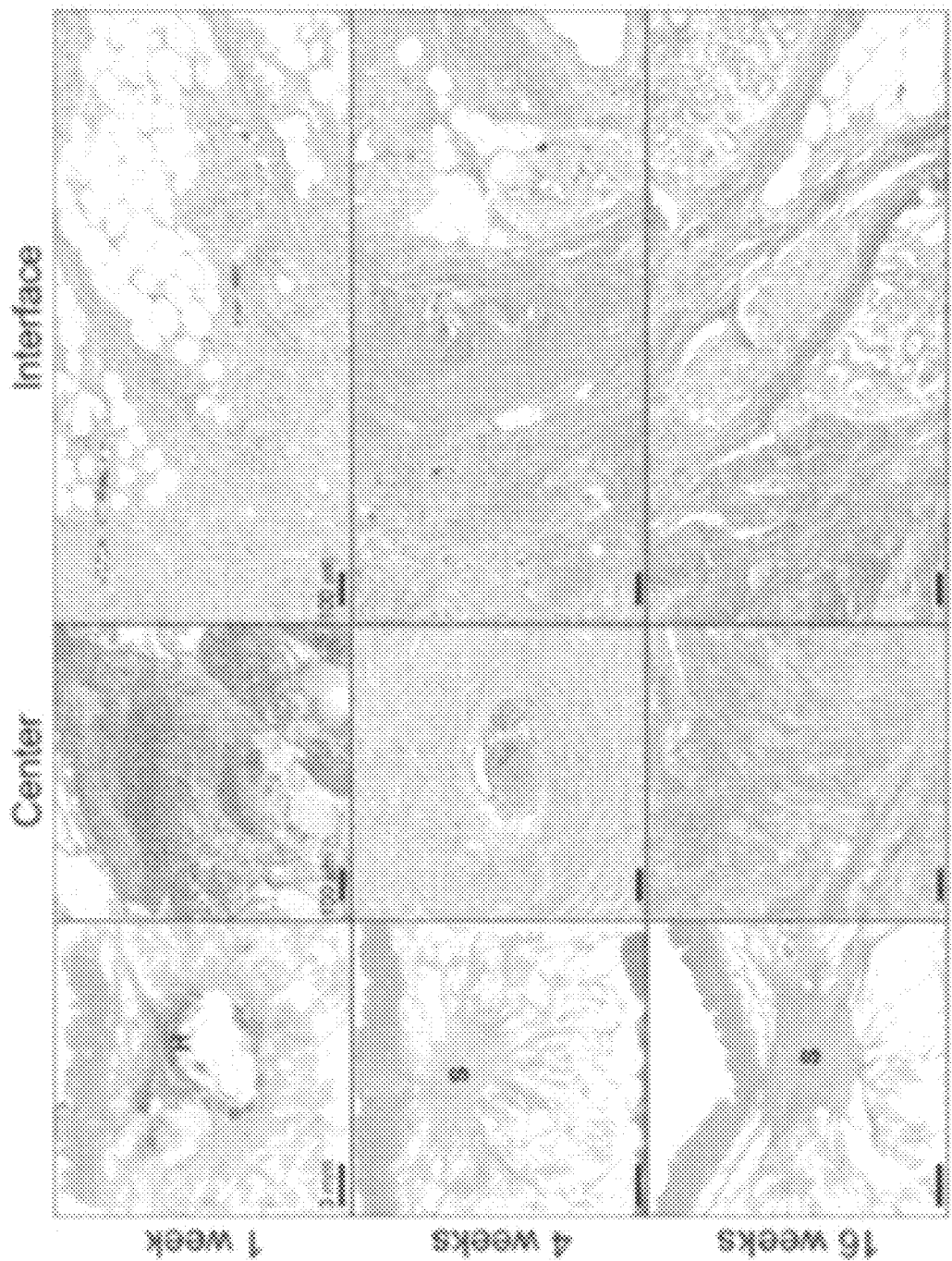

Biocompatibility and tissue response of the collagen filler were further defined based on gross and histological examination of transverse sections of breast explants, with comparisons to no fill and normal breast controls. From these analyses, it was apparent that the collagen filler maintained its volume (minimized defect contraction), was highly biocompatible, and exhibited a tissue response in absence of an inflammatory reaction typically seen with healing of an untreated tissue void or foreign body reaction typically observed with tissue-implant responses. As cells infiltrated the tissue filler matrix and new breast tissue was generated, it took on a tissue-like appearance that was difficult to discern grossly from surrounding normal tissue (FIG. 3B). In this case, the surgical clips were useful as markers of the original defect margins (FIGS. 3B, 4B). Upon histological analysis at 1 week, the collagen filler was evident within the tissue void, where it appeared as a homogenous, light pink (eosinophilic) staining material (FIG. 4A). Often surrounding the filler was a band of hemorrhage, fibrin, and a few leukocytes, which was attributable to the surgical manipulation of the tissue (FIG. 4A). At the filler-host tissue interface, there were focally extensive areas of proliferating fibroblasts (mesenchymal cells) with few small-caliber vessels infiltrating the matrix edges. The surrounding breast tissue appeared largely normal, with remodeling areas adjacent to the surgical site. These regions contained aggregates of remodeling epithelial cells, some of which appeared to be ductules while others were more irregularly shaped, suggestive of rudimentary lobules (FIG. 4A). It is noteworthy that there was no evidence of an inflammatory-mediated foreign body reaction or active biodegradation that is characteristic of conventional implantable materials. At the 4-week time point, fibroblasts, along with newly formed vasculature, extended into deeper portions of the collagen filler matrix, with infiltrating cells most abundant at the periphery and dwindling further into the center (FIG. 4A). Multifocal aggregates of epithelial cells were observed, which were again consistent with precursors of glandular structures (FIG. 4A). By 16 weeks, the matrix was completely cellularized, appearing as mature, remodeled collagen fibers and bundles, with some sites displaying small discernible regions of acellular eosinophilic filler material. Small caliber vessels were present diffusely and evenly distributed throughout the matrix (FIG. 4A). Within the vascularized collagen matrix, newly formed lobules and ducts, which stained positively for cytokeratin, and adipose tissue were present, especially at the periphery (FIGS. 11A, 11B, 4A). The glandular morphology was well developed and mature with no remarkable pathology.

By contrast, at 1 week, hematoma formation was evident upon both gross and histological evaluation of no fill breast explants (FIGS. 3B, 4B). Hemorrhage, fibrin clot, and leukocytes, including neutrophils and macrophages, were evident within the lumpectomy site. Intermixed within areas of hemorrhage were proliferating fibroblasts with few small caliber vessels, consistent with fibrovascular scar tissue associated with reparative wound healing. Scattered necrotic regions with active inflammation were also apparent surrounding the defect area. By 4 weeks, these tissue defects contracted as evidenced by significant clip displacement grossly and a star-like, constricted appearance histologically (FIG. 4B). Fibrovascular scar tissue was prominent within the defect area, with multiple, small regions of necrosis and inflammation noted throughout and near the defect border (FIG. 4B). Active remodeling of glandular and adipose tissue was observed in tissue regions surrounding the defect (FIG. 4B). By 16 weeks, the fibrous scar tissue increased in density, appearing as differentially oriented swirls of parallel-aligned fibrous tissue densely populated by myofibroblasts. While lobules, ducts, and adipose tissue were identified surrounding the defect, multiple necrotic glands with poorly developed morphological features were found within the scar tissue periphery, as evidenced by the presence of inflammatory mediators and residual low-level, diffuse cytokeratin staining. (FIGS. 4B, 11C, 11D).

Example 8

Tissue Filler Matrix Does Not Compromise Interpretation of Sonograms and Radiographs Mammography and ultrasonography are routinely used as follow-up diagnostic procedures to BCS to monitor for cancer recurrence. To ensure that the collagen filler did not compromise or interfere with image interpretation, ultrasound was performed on all pig breasts prior to euthanasia and radiographs were taken of each individual whole breast following mastectomy. Sonograms obtained over the 16-week study showed that the tissue filler matrix did not obscure or prevent interrogation of breast tissue and did not produce any regions of unexpected echogenicity (FIG. 5A). At 1 week, a large, irregularly shaped hypoechoic region was observed within collagen-treated breasts containing varying degrees of heterogeneous echoes (FIG. 5A). Such signals were not surprising given that the filler microstructure represents a randomly-oriented meshwork of collagen fibrils measuring roughly 400 μm in diameter. While these regions appeared to maintain their volume over time, they gradually took on the appearance of normal tissue, which corroborated the cellularization and vascularization observed within gross explants and histologically (FIG. 5A). No fill treated voids also showed an irregular-shaped hypoechoic region consistent with seroma and hemorrhage at 1 week (FIG. 5A). By 4- and 16-week time points, these regions diminished in size, producing a heterogeneous signal consistent with contraction and scar formation (FIG. 5A).

Figure 5B:
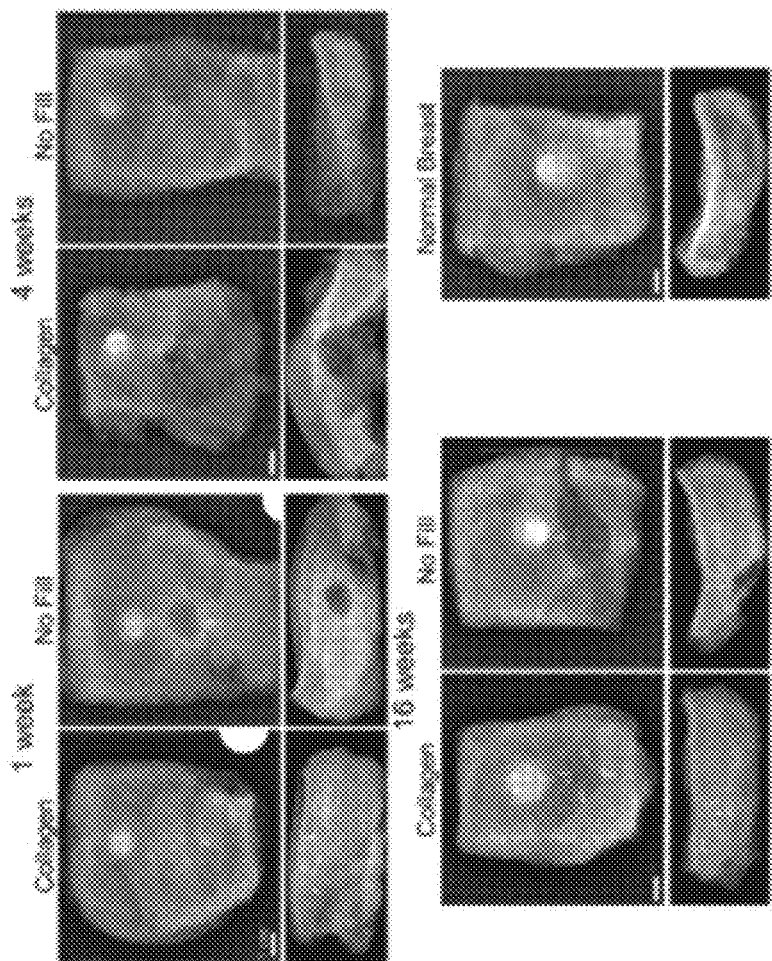

The tissue filler matrix also did not interfere with radiograph interpretation, but rather displayed an opacity consistent with normal tissue throughout the duration of the study (FIG. 5B). Additionally, radiographs provided further evidence that the collagen matrix maintained the void volume with limited clip displacement over time (FIG. 5B). The majority of untreated (no fill) surgical voids also produced radiographs that appeared consistent with normal tissue at 1 week, with a small number of sites displaying obvious darkened regions consistent with an air pocket, seroma, or hematoma (FIG. 5B). The progressive displacement of surgical clips observed at 4- and 16-week time points provided further evidence of defect contraction and scarring over time (FIG. 5B).

Example 9

Figure 9:
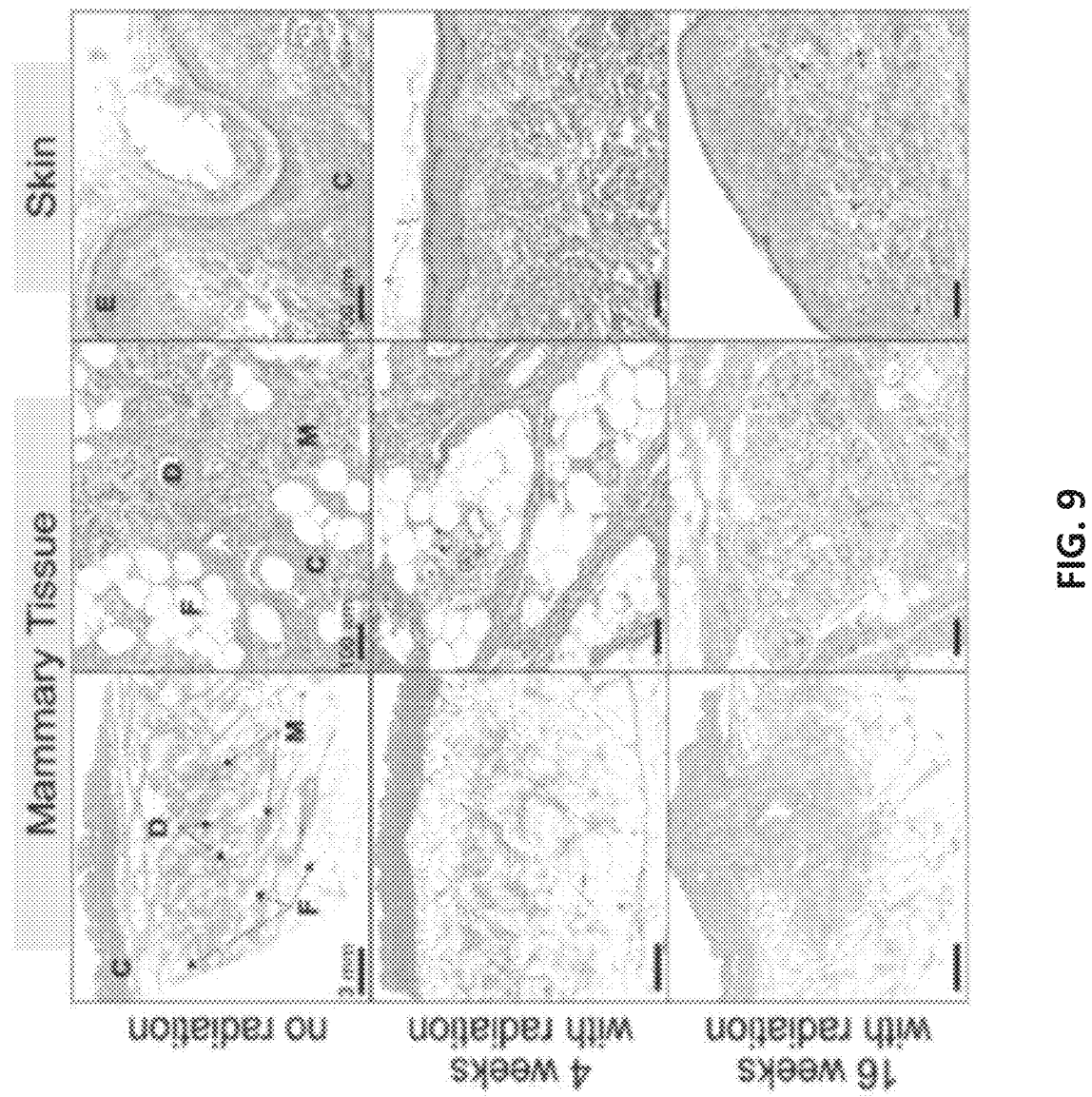
FIG. 9 shows multiple tissue type composition of normal breast tissue and overlying skin and effects of irradiation. Cross-sections (H&E) are shown of normal breast tissue and associated skin from pigs receiving no irradiation and 4 weeks and 16 weeks after lumpectomy with radiation. Mammary tissue is composed of collagenous connective tissue (C), mammary gland lobules (M), mammary ducts (D), and adipose (fatty) tissue (F). Skin contains a multicellular epidermal layer (E) with an underlying collagenous dermis (C).
Figure 12A:
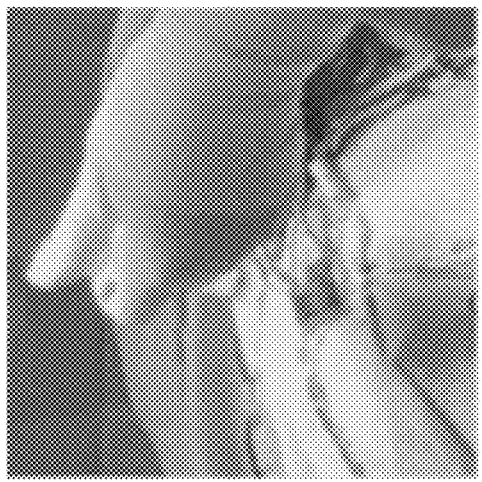
FIGS. 12A-12D show an overview of the creation of skeletal muscle and adipose tissue defects within the dorsal neck of a pig. The defect was filled with liquid collagen, which conformed to the void geometry. Within approximately 1 minute after application, the liquid collagen polymerized in situ, forming a collagen matrix that restored tissue form and continuity.
Figure 12B:
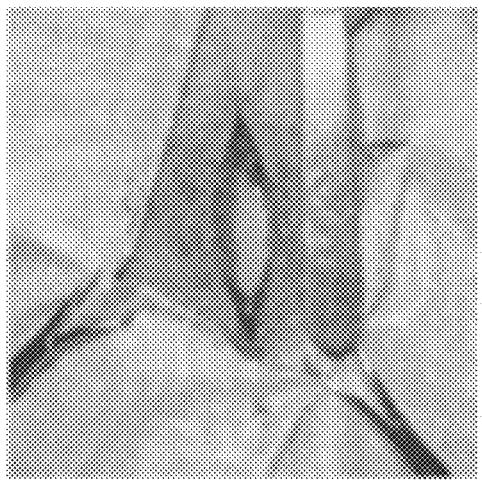
Figure 12C:
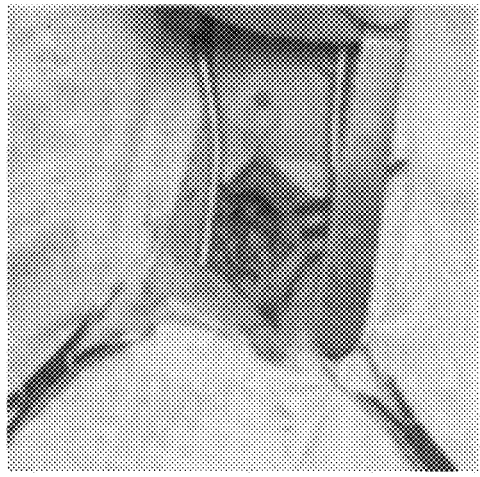
Figure 12D:
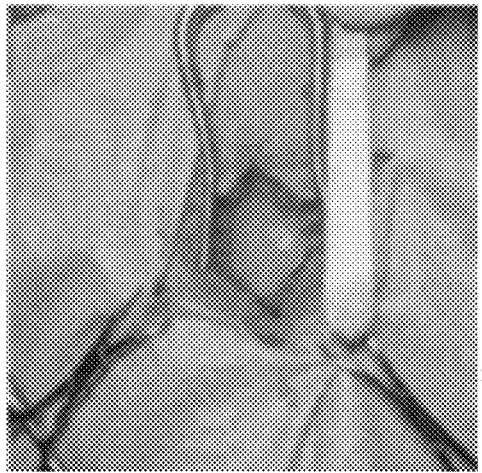

Irradiation Does Not Adversely Affect Collagen Filler or Tissue-Implant Response To determine if the collagen filler was compatible with radiation therapy, a cohort of animals was subjected to ventral irradiation two weeks following the simulated lumpectomy procedure. Computed tomography (CT) based, three-dimensional conformal treatment (3D-CRT) plans were generated for each animal to deliver a total dose of 20 Gy to the cranial 5 pairs of mammary glands in 5 consecutive-day fractions using 6 MV X-rays from a Varian EX clinical linear accelerator. The caudal pair of mammary glands were excluded as non-irradiated controls. Irradiated animals displayed an increase in skin pigmentation over time as evidenced by a darkening of skin color (FIG. 2G), which would be expected in humans undergoing therapeutic irradiation as well. At the microscopic level, moderate hyperplasia or thickening of the epidermis was evident with increased melanin deposition especially within the basal epidermis (FIG. 9). At 16 weeks, breast tissue was noticeably stiffer, again a common change observed with radiation therapy. Additionally, signs of fat necrosis and atypical hyperplasia of ducts and glands were evident (FIG. 9).

Figure 6B:
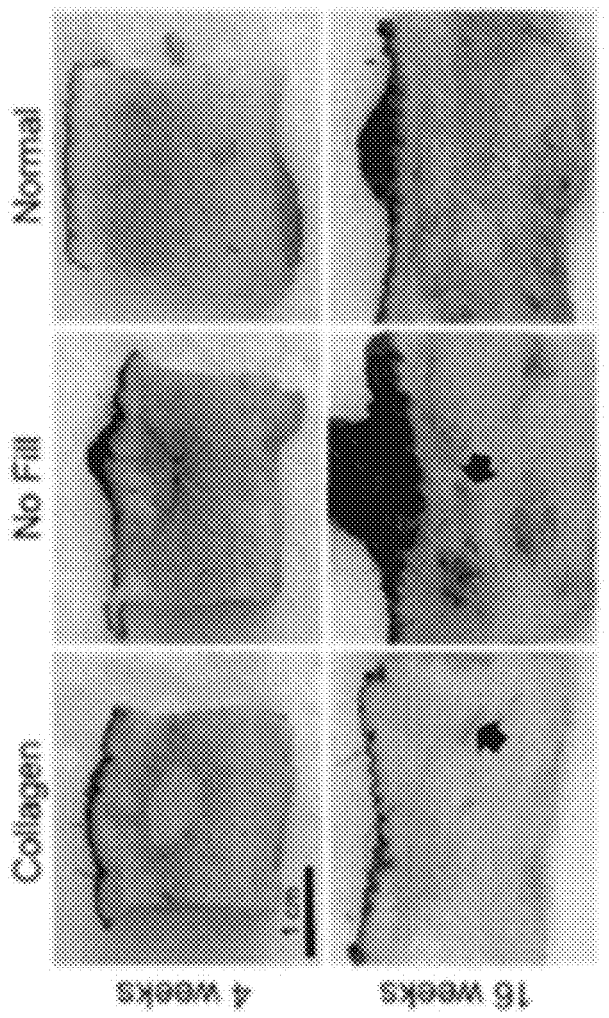
FIGS. 6A-6D show an overview of how radiation has little to no effect on tissue filler and associated tissue-implant response.
Figure 6A:
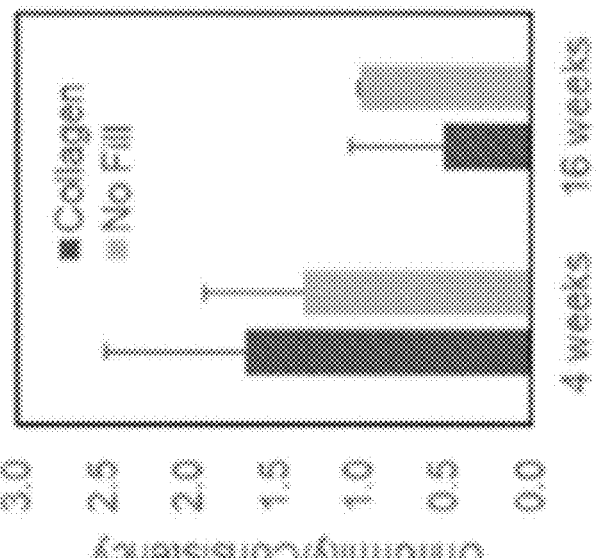
Figure 6C:
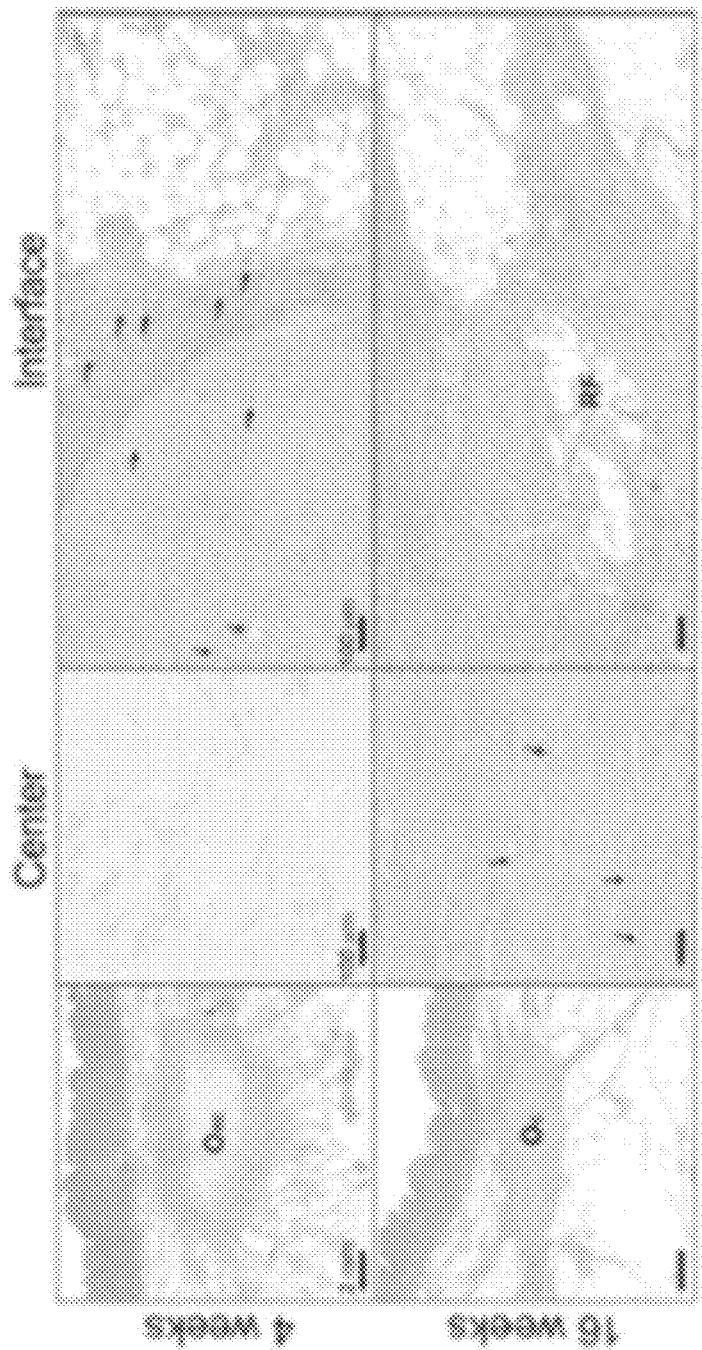
Figure 6D:
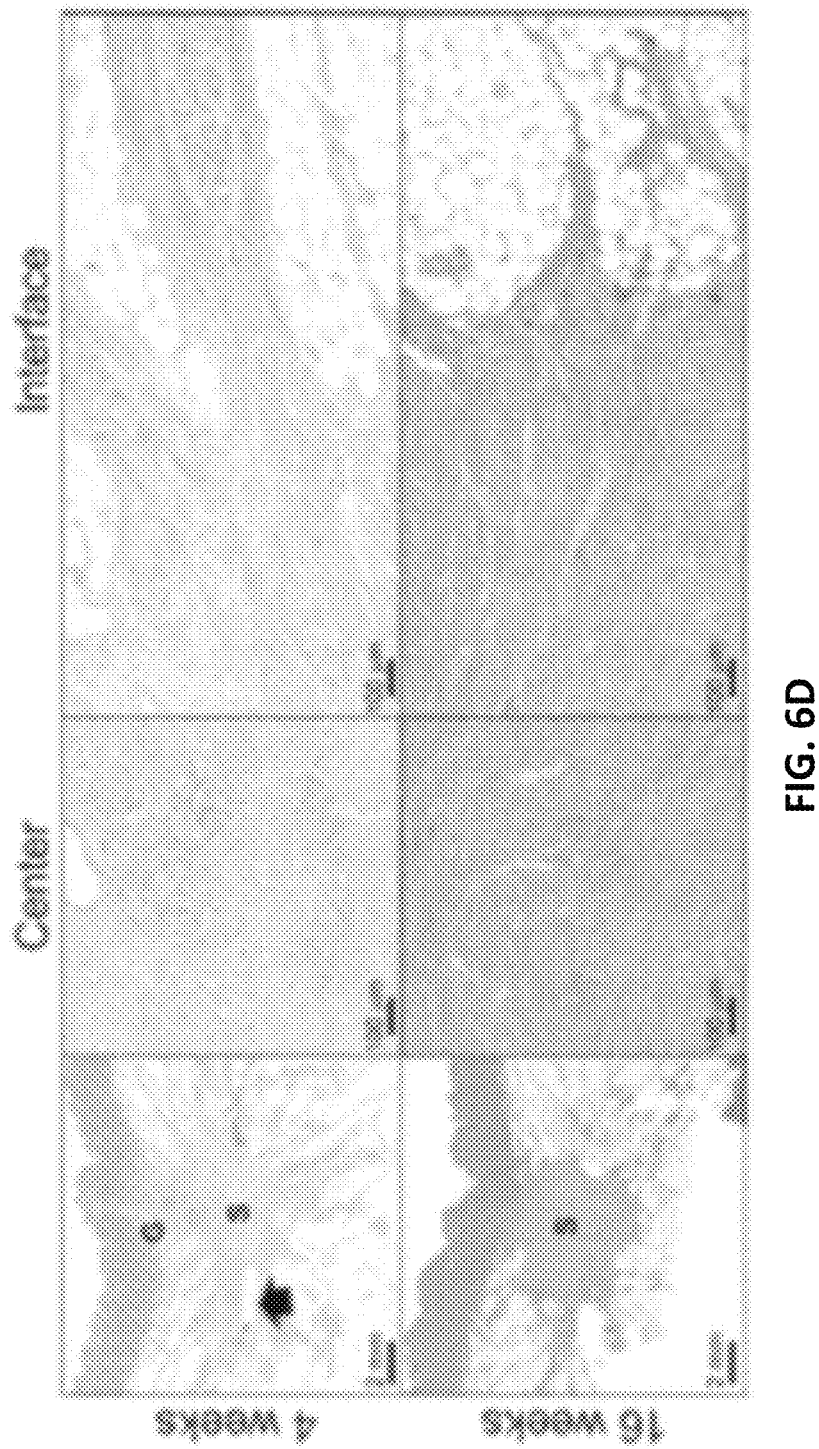
Figure 7A:
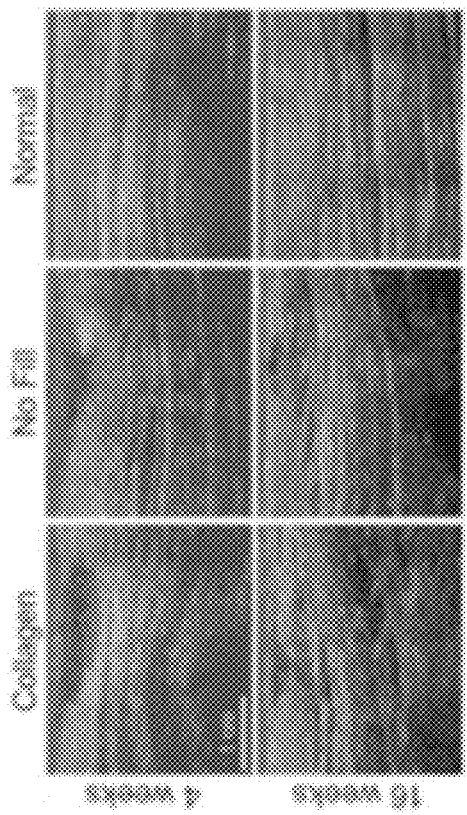
FIGS. 7A-7B show an overview of how the tissue filler does not compromise interpretation of diagnostic images of breast tissue even after adjunct radiation.
Figure 7B:
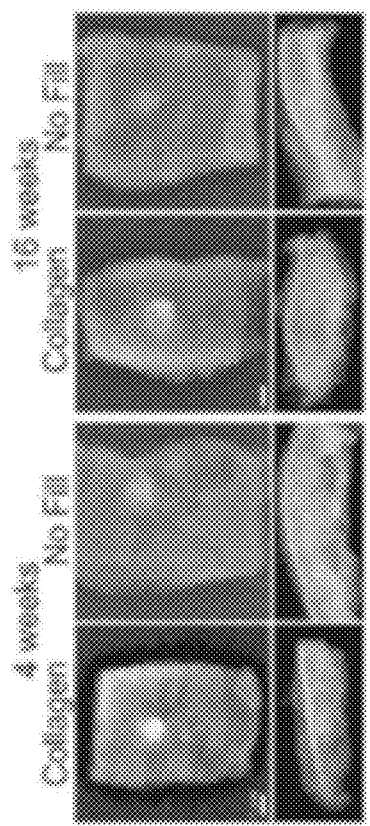

With the exception of differences in skin pigmentation, all breasts and surgical sites healed well, appearing similar to those of non-irradiated animals. Average breast uniformity/consistency scores for collagen filler-treated and no fill groups were, somewhat higher in irradiated versus non-irradiated animals at the respective time points, with the only exception being the 16-week collagen filler-treated group, where scores were similar (FIGS. 6A, 3A). Examination of gross explants and histological cross-sections revealed no obvious adverse effect of irradiation on the tissue filler matrix or its associated tissue response; however, subjectively, the overall healing timeline of irradiated sites appeared modestly delayed (FIGS. 6B, 6C). Over the 16-week study period, the collagen filler persisted within the surgical site, supporting progressive cellularization, vascularization, and breast tissue generation, which proceeded inward from the filler-host tissue interface. As expected, the no fill group showed contraction and the development of fibrous scar tissue (FIGS. 6B, 6D). Sonograms (FIG. 7A) and radiographs (FIG. 7B) were largely similar for irradiated and non-irradiated animals, again confirming that the collagen filler was not negatively affected by irradiation and did not produce any suspicious imaging anomalies.

Example 10

Discussion of Results

In the present work, porcine breasts varied in size and tissue composition, giving rise to consistency differences that were apparent both qualitatively and quantitatively. The measured compressive modulus range (approximately 6-19 kPa) encompassed breast consistencies observed in women, which reportedly ranges from (17-66 kPa depending on breast composition (e.g., fibroglandular versus fatty) and testing parameters (e.g., strain rate, preconditioning). The healing response of untreated breast defects was similar to that observed in women following BCS, yielding scar tissue that was structurally and functionally distinct from normal breast tissue. The 16-week longitudinal study showed progression through the classic overlapping phases of reparative wound healing that results in scarring, including hemostasis and inflammation, proliferation, and remodeling as shown in FIG. 8A. Substantial contraction of the defect, as evidenced by clip displacement and star-like scar tissue morphology, was facilitated by the initial fibrin clot and provisional matrix which are mechanically weak compared to normal breast ECM. The process of scar formation and remodeling over time is perhaps the most unpredictable and troubling aspect of BCS, since it is known to contribute to pain, distortions in the breast contour and consistency, and loss of sensation, all of which negatively affect women emotionally and psychologically.

Filling the defect volume with a long-lasting fibrillar collagen matrix, that is naturally metabolized and remodeled rather than actively degraded, resulted in a healing response where immune mediators were largely absent, and the outcome was more regenerative rather than reparative (FIG. 8B). Based on these results, the proposed regenerative healing response for the collagen filler is depicted in FIG. 8B. Since the injectable, in-situ forming matrix filled and conformed to defects and effectively integrated with surrounding host tissue, it re-established a structural and mechanical continuum across the tissue, which is known to be important to scar-free healing and tissue morphogenesis. Notably, the compression modulus (7.67±0.42 kPa) of the collagen filler fell within the range of both pig and human breast mechanical properties. The dense microstructure and compression properties of the collagen filler effectively resisted contraction forces exerted by the surrounding normal tissue as well as infiltrating cells. Additionally, since matrix mechanical properties were similar to soft tissues, they did not yield any concerning palpable breast inconsistencies. From a translational perspective, this is important for patient satisfaction and comfort, as well as for maintaining the ability to detect recurrent cancer through palpation.

Because collagen fibrils formed by the tissue filler contain multiple functional cellular and molecular binding domains, the matrix could effectively participate in both biochemical and mechanochemical signaling, as is performed by tissue ECMs. Unlike conventional implantable materials, the matrix was initially populated by fibroblast-like mesenchymal cells, along with vessel-forming cells, rather than inflammatory mediators. The rapid and robust neovascularization response was consistent with other in vivo studies where oligomer has been implanted into other microenvironments and used for in vitro investigations of underlying mechanisms of vessel formation. As these front-line cells progressed deeper toward the matrix center with time, tissue neogenesis followed, with formation of adipose tissue and mammary glands, including secretory lobules and ducts. Interestingly, newly formed lobules, which were especially apparent at 4- and 16-week time points, were reminiscent of those found in nulliparous (pre-pregnancy) breasts since they were largely lacking in macrophage infiltration. Collectively, the regenerative tissue response observed with the collagen fill has many similarities to processes associated with tissue development and morphogenesis, including mammary glands, highlighting the importance of maintaining stromal collagen and its associated mechanobiological continuum.

As part of this study, it was also demonstrated that the collagen filler was not negatively impacted by radiation therapy and did not compromise interpretation of diagnostic imaging procedures. In the present study, irradiation was applied 2 weeks following simulated lumpectomy, which is within the range of adjunct radiation administration following BCS. Tumors and tissues with rapid cell turnover, such as the epidermal layer of the skin, are most sensitive to irradiation effects, with the extent of damage depending on the total radiation dose and time over which the radiation is delivered. Irradiation resulted in hyperpigmentation of skin, an expected side effect that is analogous to sunburn or tanning responses displayed in humans, as well as moderate levels of fat necrosis and hyperplasia of glands and ducts. For both collagen filler and no fill treated groups, the healing progressed similarly to respective non-irradiated groups; however, the healing rate appeared modestly slower based on breast consistency scores and histopathological analysis. Such results were not surprising since irradiation is known to cause delays in wound healing. Based on combined histopathology, x-ray and ultrasound analyses, the collagen filler and its associated signaling capacity were determined to be largely unaffected by irradiation. Radiographs and ultrasonograms also indicated that the collagen filler yielded no suspicious artifacts. This has been a major drawback with fat grafting, where a wide spectrum of alterations in breast tissue have been detected via these diagnostic imaging techniques, ranging from benign-looking lipid cysts to findings suspicious for malignancy such as micro-calcification, focal masses, and speculated areas of increased opacity.

Given that this work represents an early proof-of-principle evaluation, these studies are not without limitations. First, owing to breast size differences between pig and human, a quadrantectomy was performed with removal of roughly 25% pig breast volume. Defect volumes ranged from 2-5.5 mL, with an average defect volume of about 3 mL. While quadrantectomies are rarely, if ever, performed on women, these absolute defect volumes fell within the range of human clinical procedures. Specifically, published human clinical reports indicate that 67% and 82% of breast tumors are ::::;1.9 cm (:S3.6 mL) and ::::;2.9 cm (:S12.8 mL) in diameter (volume), respectively. While additional studies are needed to determine how defect size affects material performance, no detrimental outcomes are anticipated based on observed material mode of action and tissue-implant response. However, it is anticipated that time to complete cellularization and healing would vary directly with defect volume. Second, since the longest timepoint evaluated was 16 weeks, additional animal and human clinical studies are needed to define long-term (i.e., 6 months or greater) collagen filler outcomes. A third limitation of these large-animal studies was that pigs were cancer free. Since the pigs used in this large-animal study were cancer free, the effect of collagen filler on tumor promotion and recurrence cannot be fully evaluated. For a number of reasons, it is not anticipated that the collagen filler would pose a risk to oncologic safety. First, since breast surgeons would be able to more predictably maintain breast contour and consistency, they would have increased confidence about excising more tissue to achieve negative margins. In addition, the present inventors have shown that the collagen filler induces no inflammatory or foreign body response, which is especially important since macrophage infiltration and other processes (e.g., cytokine release) associated with inflammation have been implicated in tumor promotion. Additionally, when tested with various cancer cell types in vitro, high fibril density/stiffness of oligomeric collagen matrices was found to limit tumor cell proliferation and migration. Finally, to further combat tumor recurrence, a chemotherapeutic or other anti-cancer agents could be readily added to the matrix-forming reaction to achieve targeted and localized delivery. This would dramatically decrease the amount of drug administered and minimize side effects associated with systemic administration.

In conclusion, a restorative and regenerative tissue filler that forms in situ and is fashioned from a collagen polymer is described which appears to address surgeon needs and overcome major limitations associated with conventional implantable materials. This is the first report of a breast filler that persists, maintains its volume, and induces progressive breast tissue generation, including mammary glands, ducts, and adipose tissue. Additionally, study findings have important implications to regenerative medicine, suggesting that decreased inflammation and maintenance of a collagen structural and mechanical continuum tilts the healing balance from repair (scar formation) towards regeneration. This work sets the stage for future pre-clinical and clinical studies where the translation potential of this tissue filler may be further validated for BCS and other tissue restoration and reconstruction needs.

Example 11

Skeletal Muscle Restoration and Regeneration

Figure 13:
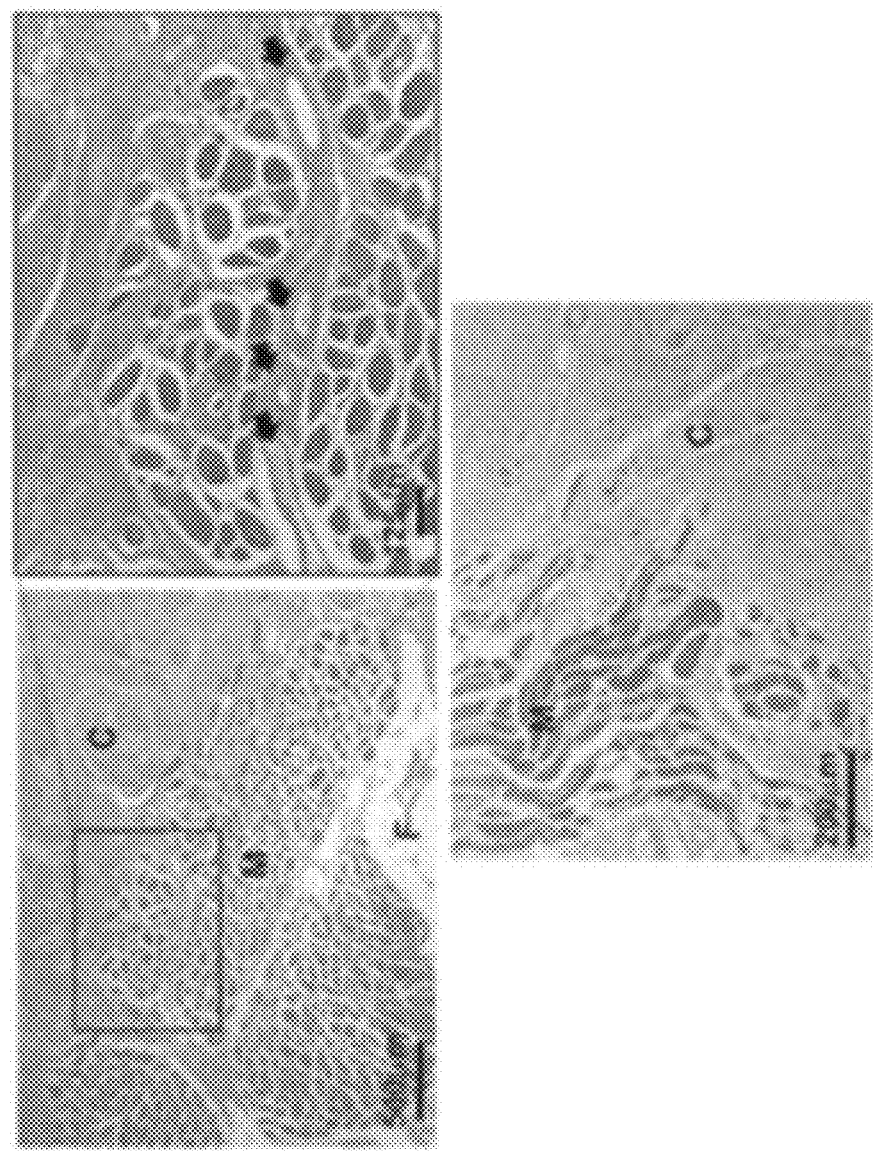
FIG. 13 shows an overview of newly formed skeletal muscle and adipose (fat) tissue within collagen matrix 11 weeks following implantation with no evidence of an inflammatory response (i.e., infiltration of neutrophils and macrophages) typically seen with healing of an untreated tissue void or foreign body reaction (i.e., activation of macrophages, formation of giant cells, phagocytosis, and fibrous capsule formation) typically observed with tissue-implant responses. C: collagen tissue filler matrix; F: fat; M: skeletal muscle; arrows: associated microvasculature.
Figure 14A:
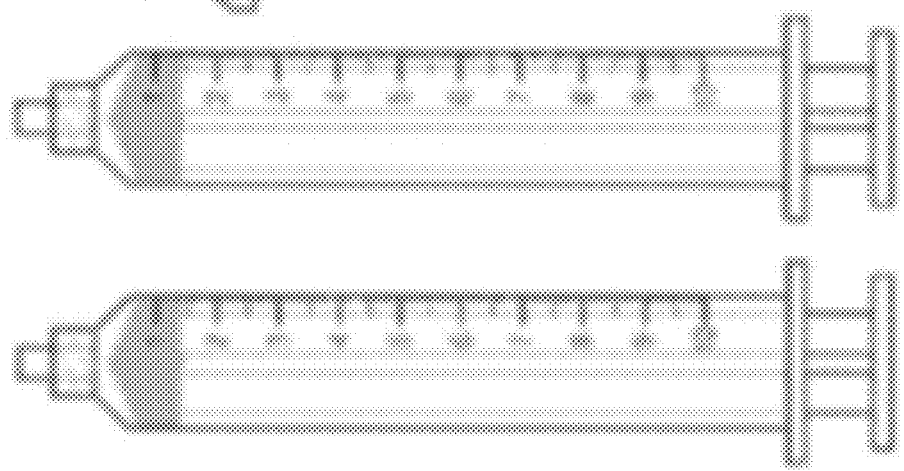
FIGS. 14A-14G show a schematic of representative components of a collagen tissue filler kit.
Figure 14B:
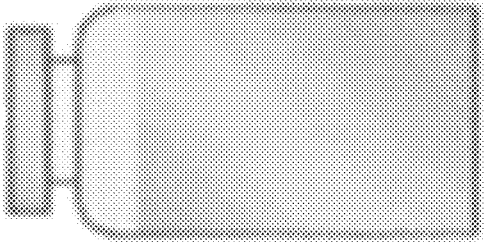
Figure 14C:
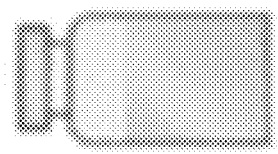
Figure 14D:
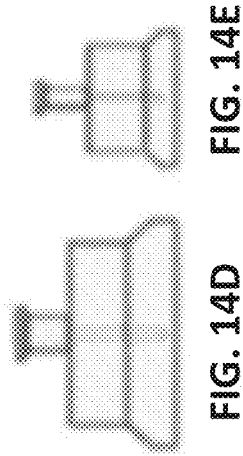
Figure 14E:
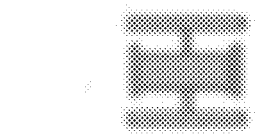
Figure 14F:
Figure 14G:

Yucatan mini-pigs were placed under general anesthesia. A defect (approximately 2 cm×2 cm) was created within skeletal muscle and adipose regions of the dorsal neck, as shown in FIGS. 12A-12D. The tissue void was filled with the liquid collagen filler, which conformed to the void geometry. Within approximately 1 minute after application, the liquid collagen self-assembled (polymerized) in situ, forming a fibrillar collagen matrix that restored tissue continuity and form. The site was then sutured closed. Eleven weeks following creation of the tissue defect, the defect site, along with surrounding normal tissue, was harvested and placed in 10% buffered formalin. Formalin-fixed explanted tissues were bisected, embedded in paraffin, and sectioned. Sections were stained with hematoxylin and eosin (H&E) and Masson's trichrome. FIG. 13 shows newly formed skeletal muscle and adipose (fat) tissue within collagen matrix 11 weeks following implantation. In FIG. 13 indicates collagen matrix, F indicates fat, M indicates skeletal muscle, and the arrows indicate associated microvasculature.

Example 12

Tissue Filler Kit and Associated Performance Characteristics

The tissue filler comprises oligomeric collagen derived from porcine dermis and a neutralization buffer. In some embodiments, this in-situ forming collagen device may be supplied as a single-use kit containing the following, as shown in FIG. 14: a sterile glass vial containing the collagen solution (10 mL) in dilute (0.01 N) hydrochloric acid, a sterile glass vial containing the neutralization buffer (self-assembly reagent; 2 mL), two sterile 10-mL syringes, two sterile needle-free vial adapters, a sterile luer-lock connector, and a sterile applicator tip. In other embodiments, a pre-filled dual-barrel syringe with a static mixing tip may be provided. This dual-barrel product format may be used to support mixing of the collagen solution and neutralization buffer during administration.

Table 1 provides a summary of neutralization buffer components and their role in bringing the collagen solution to physiologic pH, ionic strength, and osmolarity to induce the matrix-forming reaction.

TABLE 1

Summary of Neutralization Buffer (Self-Assembly Reagent) Components.

| Component | Concentration 10× (Prior to mixing) | Concentration 1× (After mixing) | Role |
|---|---|---|---|
| Sodium chloride (NaCl) | 1.37M | 0.137M | Provide physiologic ionic strength and osmolarity |
| Potassium chloride (KCl) | 27 mM | 2.7 mM | Provide physiologic ionic strength and osmolarity |
| Disodium phosphate (Na2HPO4) | 81 mM | 8.1 mM | Provide physiologically relevant buffer to control and maintain pH |
| Monopotassium phosphate ($KH_2PO_4$) | 15 mM | 1.5 mM | |
| Sodium hydroxide (NaOH) | 0.1N | 0.01N | Assist in controlling pH of the collagen solution |
| Glucose ($C_{12}H_{12}O_6$) | 55.5 mM | 5.5 mM | Non-essential for matrix-forming reaction; represents physiologically relevant nutrient for cells |

As shown in Table 1, the neutralization buffer represents a 1ox phosphate buffered saline which, when mixed with the collagen solution, brings it to physiologic conditions, including pH, osmolarity, and ionic strength. After drawing up 9 mL of collagen solution in one syringe and 1 mL of neutralization buffer in the other using the needle-free vial adapters, the user connects the two syringes with the luer-lock connector and mixes the two reagents thoroughly. After mixing, the neutralized collagen solution may be injected to fill and conform to tissue voids and defects, including those that are difficult to access and/or that are irregularly shaped. Upon application, the collagen undergoes an in-situ matrix-forming reaction via molecular self-assembly. The tissue filler device achieves its intended use by providing a solid, fibrillar collagen matrix that is suitable for cellularization and vascularization, maintaining a supportive environment for tissue restoration. In some embodiments, the neutralization buffer components include glucose, as shown in Table 1. In other embodiments, the neutralization buffer components do not contain glucose.

Table 2 summarizes technological and performance characteristics of neutralization buffer (self-assembly reagent) components in accordance with the present teachings.

TABLE 2

Technological and Performance Characteristics of Tissue Filler

TECHNOLOGICAL CHARACTERISTICS

| Characteristic | Specification |
|---|---|
| Material composition | Purified, soluble type I collagen |
| Collagen source | Porcine dermis |
| Neutralization Buffer (Self-assembly reagent) | 10× phosphate buffered saline: 1.37M sodium chloride, 27 mM potassium chloride, 81 mM disodium phosphate, 15 mM monopotassium phosphate, 0.1N sodium hydroxide, 55.5 mM glucose |
| Form | Collagen solution that when mixed with self-assembly reagent (10× phosphate buffered saline) forms a solid, fibrillar collagen matrix in situ; device is mixed using a dual syringe/luer connector system |
| Storage | 2-8° C.; avoid excess heat; avoid freezing |

PERFORMANCE CHARACTERISTICS

| Characteristic | Test Method | Acceptance Criteria |
|---|---|---|
| Appearance of collagen solution | Visual Inspection | Colorless viscous liquid |
| Concentration of collagen solution | Sirius Red Assay | 7.5 ± 0.5 mg/mL |
| Purity of collagen solution | SDS-PAGE | Characteristic banding pattern (refer to ~~Figure~~ FIG. 3B) |
| Impurities analysis of collagen solution and formed matrix | FTIR Analysis | Characteristic spectra for collagen before and after matrix formation |
| pH of collagen solution | USP <791> | 2.25 ± 0.25 |
| Appearance of neutralization buffer | Visual inspection | Colorless liquid |
| pH of neutralization buffer | USP <791> | 11.25 ± 0.25 |
| Conductivity of neutralization buffer | USP <644> | 106 ± 5 mS/cm |
| In-situ matrix formation (self-assembly) time | Oscillatory Shear Matrix Formation Kinetics Test | 0.8 ± 0.3 minutes |
| Shear storage modulus (G') of collagen matrix | Oscillatory Shear Rheometry Test | 3.1 ± 0.4 kPa |
| Shear loss modulus (G") of collagen matrix | | 0.4 ± 0.1 kPa |
| Compression modulus of collagen matrix | Unconfined Compression Test | 7.7 ± 1.9 kPa |
| Sterility | Test of Sterility; USP <71> | No Growth |
| Endotoxin level | LAL Assay; USP <85> | <20 EU/device |
| Elemental impurities | Elemental Impurities Test; USP<232>; USP <233> | Does not exceed limits |

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for filling a tissue void formed by the surgical removal of soft tissue from a patient, the method comprising: introducing into the tissue void a polymerizable collagen composition comprising a solution of oligomeric collagen in an amount to fill the void; and polymerizing the polymerizable collagen composition in situ to form a shape-retaining collagen scaffold having viscoelastic properties similar to soft tissues.

2. The method of claim 1 wherein the tissue void is formed in breast tissue, optionally where the void is generated by a lumpectomy procedure or a mastectomy procedure.

3. The method of claim 1 wherein the solution of oligomeric collagen comprises type I oligomeric collagen and an acid.

4. The method of claim 1 wherein said oligomeric collagen solution is mixed with a buffer solution prior to, or during, introduction into said void.

5. The method of claim 4 wherein the polymerizable collagen composition has a pH of about 5.5 to about 8.5, and said oligomeric collagen solution comprises about 8 mg/mL oligomeric collagen based on a dry weight of the oligomeric collagen.

6. The method of claim 4 wherein the polymerizable collagen composition has a self-assembly time of from about 0.2 minutes to about 1.5 minutes.

7. The method of claim 1 wherein the shape-retaining collagen scaffold has a shear storage modulus (G') of from about 2.0 kPa to about 4.0 kPa.

8. The method of claim 1 wherein the shape-retaining collagen scaffold has a shear loss modulus (G") of from about 0.1 kPa to about 0.7 kPa.

9. The method of claim 1 wherein the shape-retaining collagen scaffold has a compression modulus of from about 5.0 kPa to about 10.0 kPa.

10. The method of claim 1 wherein said polymerizable collagen composition has a pH of about 5.5 to about 8.5, wherein the oligomeric collagen has a self-assembly time of about 0.2 minutes to about 1.5, and wherein the shape-retaining collagen scaffold has a shear storage modulus (G') of from about 2.0 kPa to about 4.0 kPa, a shear loss modulus (G") of from about 0.1 kPa to about 0.7 kPa, and a compression modulus of from about 5.0 kPa to about 10.0 kPa.

11. The method of claim 1 wherein said polymerizable collagen composition is injected into the void via a syringe.

12. The method of claim 4 wherein said oligomeric collagen solution and said buffer solution are in separate containers, and are mixed prior to, or during, injection of said polymerizable collagen composition into the void via a syringe.

13. The method of claim 1 wherein the oligomeric collagen solution has been clarified using ultracentrifugation, filtered through a sterile membrane filter, dosed with ultraviolet radiation, or a combination thereof.

14. A method for filling a tissue void in the breast tissue of a patient, wherein the tissue void is generated by a lumpectomy or mastectomy procedure, said method comprising the steps of
introducing into the tissue void a polymerizable collagen composition in an amount to fill the void, said polymerizable collagen composition comprising
a solution of oligomeric collagen comprising about 7 mg/mL to about 8 mg/mL oligomeric collagen, based on a dry weight of the oligomeric collagen; and
a buffer solution,
polymerizing the polymerizable collagen composition in situ to form a shape-retaining collagen scaffold having viscoelastic properties similar to soft tissues.

15. The method of claim 4 wherein the oligomeric collagen solution is mixed with a buffer solution at a ratio of 9:1, oligomeric collagen solution to the buffer solution.

16. The method claim 4 wherein the buffer solution comprises about 0.002 N to about 0.02 N NaOH.

17. The method of claim 16 wherein the buffer solution further comprises about 1 mM to about 10 M $Na_2HPO_4$.

18. The method of claim 17 wherein the buffer solution further comprises about 0.1 mM to about 4 mM KCl, about 0.02 M to about 0.3 M NaCl, about 0.3 mM to about 3 mM $KH_2PO_4$, and less than about 0.02 mM $MgCl_2$.

19. The method of claim 1, further comprising adding cells to the oligomeric collagen solution.

* * * * *